United States Patent
Boehm et al.

(10) Patent No.: US 12,071,634 B2
(45) Date of Patent: Aug. 27, 2024

(54) HUMAN iPSC-DERIVED VASCULAR-RELATED AND HEMATOPOETIC CELLS FOR THERAPIES AND TOXICOLOGY/DRUG SCREENINGS

(71) Applicant: The USA, as represented by the Secretary, Department of Health and Human Services, Bethesda, MD (US)

(72) Inventors: Manfred Boehm, Bethesda, MD (US); Guibin Chen, Ellicott City, MD (US); Mahendra Rao, Timonium, MD (US); Andre Larochelle, Bethesda, MD (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 414 days.

(21) Appl. No.: 17/337,978

(22) Filed: Jun. 3, 2021

(65) Prior Publication Data
US 2021/0348123 A1 Nov. 11, 2021

Related U.S. Application Data

(60) Continuation of application No. 16/544,381, filed on Aug. 19, 2019, now Pat. No. 11,072,778, which is a division of application No. 15/026,313, filed as application No. PCT/US2014/058583 on Oct. 1, 2014, now Pat. No. 10,385,313.

(60) Provisional application No. 61/885,209, filed on Oct. 1, 2013.

(51) Int. Cl.
| | |
|---|---|
| C12N 5/074 | (2010.01) |
| C12N 5/00 | (2006.01) |
| C12N 5/077 | (2010.01) |
| C12N 5/0775 | (2010.01) |
| C12N 5/0789 | (2010.01) |

(52) U.S. Cl.
CPC ......... *C12N 5/0607* (2013.01); *C12N 5/0018* (2013.01); *C12N 5/0647* (2013.01); *C12N 5/0661* (2013.01); *C12N 5/0662* (2013.01); *C12N 5/0696* (2013.01); *C12N 2500/05* (2013.01); *C12N 2500/30* (2013.01); *C12N 2500/36* (2013.01); *C12N 2500/42* (2013.01); *C12N 2500/44* (2013.01); *C12N 2500/90* (2013.01); *C12N 2501/115* (2013.01); *C12N 2501/155* (2013.01); *C12N 2501/165* (2013.01); *C12N 2501/26* (2013.01); *C12N 2506/03* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 10,385,313 B2 * | 8/2019 | Boehm | C12N 5/0018 |
| 11,072,778 B2 * | 7/2021 | Boehm | C12N 5/0607 |
| 2010/0317104 A1 | 12/2010 | Elefanty et al. | |

FOREIGN PATENT DOCUMENTS

| | | |
|---|---|---|
| WO | WO 2010/099539 | 9/2010 |
| WO | WO 2014/100779 | 6/2014 |

OTHER PUBLICATIONS

Medvedev et al. Acta Naturae vol. 2(5) pp. 18-27 (Year: 2010).*
Yamanaka. Cell Stem Cell 27. pp. 523-531 (Year: 2020).*
Marks et al NEJM 376; 11 . pp. 1007-1009 (Year: 2017).*
Bai et al., "The Balance of Positive and Negative Effects of TGF-II Signaling Regulates the Development of2 Hematopoietic and Endothelial Progenitors in Human Pluripotent Stem Cells" Stem Cells and Development 22 (20):2765-2776 (Jun. 2013).
Descamps et al., "Vascular differentiation from embryonic stem cells: Novel technologies and therapeutic promises" Vascular Pharmacology 56:267-79 (2012).
Smith et al. "The aryl hydrocarbon receptor directs hematopoietic progenitor cell expansion and differentiation," Blood, May 30, 2013, vol. 122, No. 3, pp. 376-385.
Wagey et al. "Isolation, Enumeration, and Expansion of Human Mesenchymal Stem Cells in Culture," Basic Cell Culture Protocols, Methods in Molecular Biology, 2013, vol. 946, Chapter 20, pp. 315-334.
Wang et al. "Derivation of Smooth Muscle Cells with Neural Crest Origin from Human Induced Pluripotent Stem Cells," Cells Tissues Organs, 2012, vol. 195, pp. 5-14.

(Continued)

*Primary Examiner* — Blaine Lankford
(74) *Attorney, Agent, or Firm* — McDonnell Boehnen Hulbert & Berghoff LLP

(57) ABSTRACT

Described herein are cells, cell culture methods, and cell culture media compositions useful for producing and maintaining iPSC-derided cell lines that are of higher purity and maintain cell type integrity better than current iPSC-derived cell lines. Also disclosed are methods of using the described cells and media, such as therapeutic methods of use for the described cells. The described cells include iPSC-derived mesodermal precursor cells (MPC), which itself may differentiate into at least four different cell types. When cultured under appropriate conditions, the mesodermal precursor cells can be used to produce hematopoietic stem cells (HSC), mesenchymal stem cells (MSC), smooth muscle cells (SMC), or unlimited functional endothelial cells (UFEC). One characteristic that makes the described cells desirable is that they can be maintained in culture for a number of days, or passages, without changing phenotype through differentiation.

5 Claims, 19 Drawing Sheets

(56) References Cited

OTHER PUBLICATIONS

Zanetta et al. "Expression of von Willebrand factor, an endothelial cell marker, is up-regulated by angiogenesis factors: A potential method for objective assessment of tumor angiogenesis," International Journal of Cancer, Jan. 2000, vol. 85, No. 2, pp. 281-288.
International Search Report and Written Opinion prepared by the European Patent Office on Nov. 27, 2014, for International Application No. PCT/US2014/058583.
Official Action for Canada Patent Application No. 2,925,774, dated Jan. 24, 2017 5 pages.
Official Action for Canada Patent Application No. 2,925,774, dated Dec. 6, 2017 7 pages.
Official Action for Canada Patent Application No. 2,925,774, dated Aug. 20, 2018 6 pages.
Official Action for European Patent Application No. 14790863.6, dated Jan. 23, 2017 5 pages.
Official Action for European Patent Application No. 14790863.6, dated Nov. 16, 2017 4 pages.
Official Action for European Patent Application No. 14790863.6, dated Sep. 13, 2018 4 pages.
Official Action for U.S. Appl. No. 15/026,313, mailed Jul. 28, 2017 8 pages Restriction Requirement.
Official Action for U.S. Appl. No. 15/026,313, dated Dec. 22, 2017 8 pages.
Official Action for U.S. Appl. No. 15/026,313, dated Aug. 10, 2018 8 pages.
Notice of Allowance for U.S. Appl. No. 15/026,313, dated Apr. 4, 2019 7 pages.
Official Action for European Patent Application No. 14 790863.6, dated Oct. 7, 2019 6 pages.
Official Action for European Patent Application No. 14790863.6, dated Apr. 21, 2020 7 pages.
Office Action for Canadian Application No. 2,925,774 mailed Jun. 4, 2020.
Office Action from Canadian counterpart application CA 2,925, 77 4; dated Feb. 22, 2021, pp. 1-4.
Gao et al., "Mesenchymal stem cells: ideal seeds for treating diseases," Hum Cell. Nov. 2021;34(6):1585-1600.
Undale et al., "Mesenchymal stem cells for bone repair and metabolic bone diseases," Mayo Clin Proc. Oct. 2009;84(10):893-902.

* cited by examiner

SSEA-4

TRA-1-60

Oct 4

Nanog

HiPSC1 hiPSC2

Endoderm

Mesoderm

Ectoderm

Adhering

Suspension

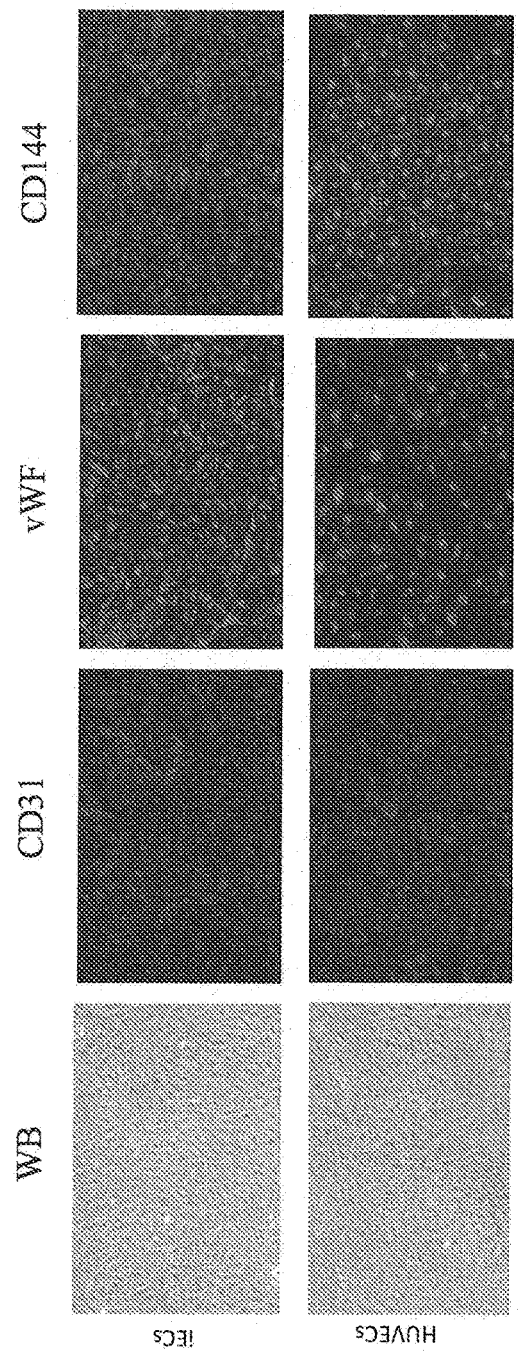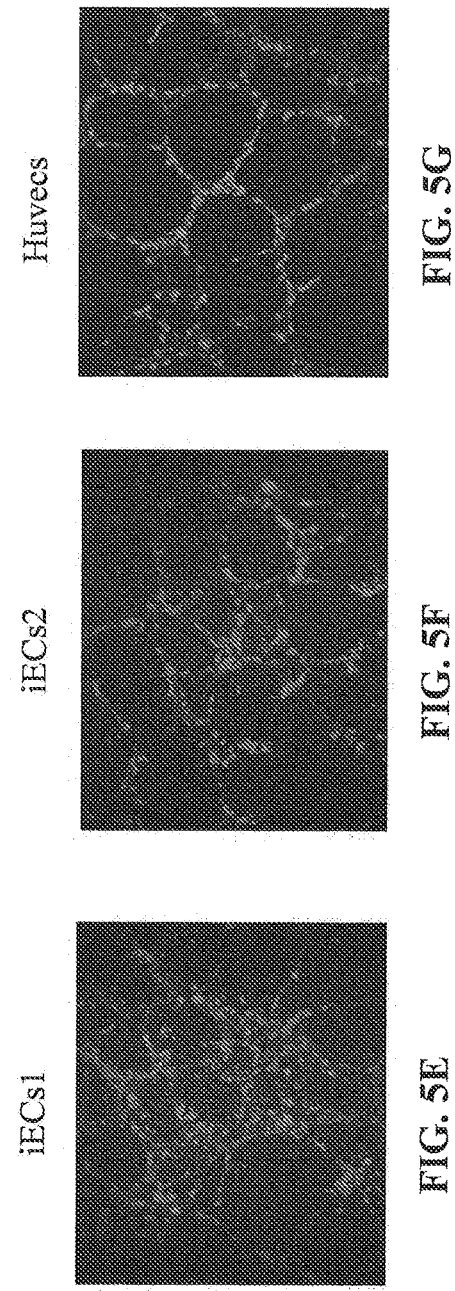

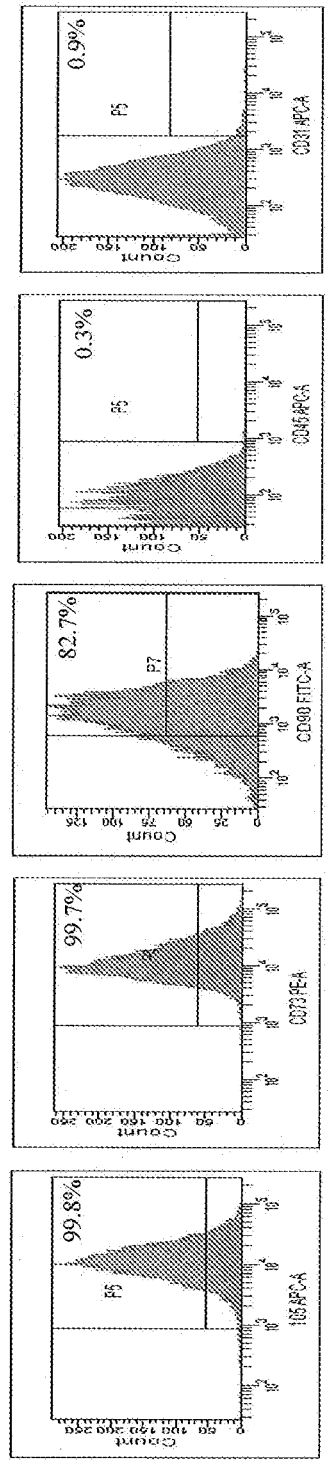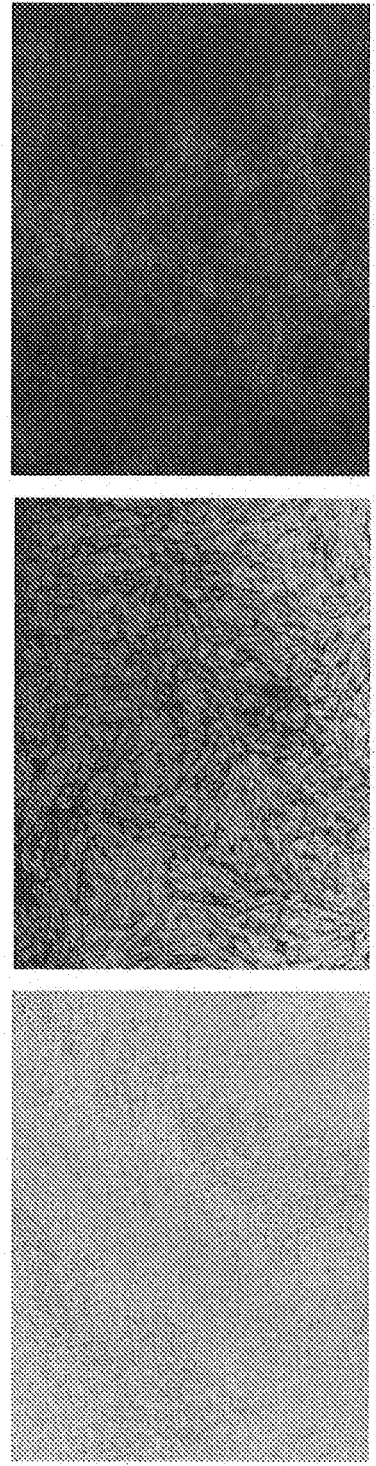
FIG. 6A  FIG. 6B  FIG. 6C  FIG. 6D  FIG. 6E
FIG. 6F  FIG. 6G  FIG. 6H

HUMAN iPSC-DERIVED VASCULAR-RELATED AND HEMATOPOETIC CELLS FOR THERAPIES AND TOXICOLOGY/DRUG SCREENINGS

CROSS-REFERENCE TO RELATED APPLICATIONS

This application is a continuation of U.S. application Ser. No. 16/544,381, filed on Aug. 19, 2019 and issued as the U.S. Pat. No. 11,072,778 on Jul. 27, 2021, which is a divisional of U.S. patent application Ser. No. 15/026,313, filed on Mar. 31, 2016, and issued as the U.S. Pat. No. 10,385,313 on Aug. 20, 2019, which is a U.S. national phase of International Application No.: PCT/US2014/058583 filed on Oct. 1, 2014, which claims priority to and benefit of the U.S. Provisional Appl. No. 61/885,209, filed on Oct. 1, 2013. The entire disclosure contents of these applications are herewith incorporated by reference in their entirety into the present application.

BACKGROUND

The use of human stem cells for clinical purposes has become a subject of increasing interest in recent years. This interest has only intensified in the wake of the more recent discoveries that human somatic cells can be induced to form pluripotent stem cells when certain transcription factors are overexpressed. Human induced pluripotent stem cells (hiPSCs) can be generated in a variety of ways, such as reprogramming somatic cells by the expression of four transcription factors. The hiPSCs exhibit similar properties to human embryonic stem cells (hESCs), including the ability to self-renew and differentiate into all three embryonic germ layers: ectoderm, endoderm, or mesoderm. Additionally, hiPSCs overcome ethical concerns, relative to generating hESCs from human embryos, because no embryonic cells are needed to form hiPSCs. Human iPSCs can be induced into any cell type and, since they can be maintained over many passages, they can serve as an almost unlimited source to generate cells from any given person. These properties make iPSC-derived cells a valuable product for cell therapies and toxicology or pharmaceutical high throughput screens. However, therapeutic and commercial uses of iPSC-derived cell products are hampered by low quantities and cell culture impurity due to limitations with current methods for producing and maintaining these cells.

SUMMARY

Described herein are cells, cell culture methods, and cell culture media compositions useful for producing and maintaining iPSC-derived cell lines that are of higher purity and maintain cell type integrity better than current iPSC-derived cell lines. Also disclosed are methods of using the described cells and media.

One aspect of the present disclosure is an iPSC-derived mesodermal precursor cell (MPC) line, positive for CD34 and CD31 expression, that may be used to produce at least four different cell types. When cultured under appropriate conditions, these mesodermal precursor cells can be used to produce hematopoietic stem cells (HSC), mesenchymal stem cells (MSC), smooth muscle cells (SMC), or unlimited functional endothelial cells (UFEC). One characteristic that makes the mesodermal precursor cells described herein desirable is that these cells can be maintained in culture for a number of days, or passages, without changing phenotype through differentiation.

The HSCs described herein can be produced by culturing the described MPCs in medium and under conditions known to cause cells to differentiate into HSCs. The described HSCs may be characterized by the expression of CD34, CD31, and CD45. Another characteristic of the described HSCs is that they have the ability to reconstitute the hematopoietic system of an irradiated subject, such as a mouse. The described HSCs also have the ability to maintain their phenotype for extended periods without differentiating, when maintained under appropriate conditions.

The described MPCs are also capable of giving rise to UFECs when cultured under conditions known to allow for differentiation into cells of an endothelial lineage. The described UFECs can be characterized by the expression of CD31, vWF, and CD144. In addition, these cells can mediate the uptake of acetylated low density lipoproteins (LDL). Furthermore, the UFECs produced using the methods and cells described herein have the ability to form vascular-like structures in vitro, a hallmark of endothelial cell progenitors.

Another cell type capable of being produced by the MPCs described herein are MSCs. The MSCs described herein can be characterized by the expression of CD90, CD73, and CD105 in the absence of CD31 and CD45. These cells can also differentiate in vivo or in vitro into a number of different cell types, including adipocytes, osteoblasts, myocytes, or chondrocytes, when cultured under conditions known to cause progenitor cells to differentiate into the respective cell type. The described MSCs also have the ability to maintain their phenotype for extended periods without differentiating, when maintained under appropriate conditions.

The described MPCs may also be used to generate smooth muscle cells according to the methods described herein. For example, the described MPCs can differentiate into smooth muscle cells when cultured under conditions known to cause progenitor cells to differentiate into SMCs. The described SMCs are characterized by the expression of α-SMA, calponin, and SM22. The described SMCs also have the ability to maintain their phenotype for extended periods without differentiating, when maintained under appropriate conditions.

In some embodiments the cell types described herein may be generated using the cells of a subject to produce autologous cells using the cell production methods described herein. The differentiated autologous cells can then be administered to the subject for therapeutic purposes.

Described herein are various tissue culture media that may be used to produce the cells characterized in the present disclosure. In some embodiments the medium formulation includes a mixture of Iscove's modified Dulbecco's medium (IMDM), Ham's F-12 Nutrient Mix, with L-alanyl-L-glutamine additive, albumin, α-monothioglycerol, protein-free hybridoma mixture II, L-ascorbic acid 2-phosphate, L-alanyl-L-glutamine, antibiotic, cholesterol lipids, insulin-transferrin-selenium-ethanolamine supplement, bone morphogenic protein 4, vascular endothelial growth factor, and basic fibroblast growth factor. In some embodiments the medium formulation includes a mixture of Iscove's modified Dulbecco's medium (IMDM), Ham's F-12 Nutrient Mix, with L-alanyl-L-glutamine additive, albumin, α-monothioglycerol, protein-free hybridoma mixture II, L-ascorbic acid 2-phosphate, L-alanyl-L-glutamine, antibiotic, insulin-transferrin-selenium-ethanolamine supplement, bone morphogenic protein 4, vascular endothelial growth factor, and basic fibroblast growth factor. Where the described components are, or include, proteins, such as albumin, bone morphogenic protein 4, vascular endothelial growth factor, or basic fibroblast growth factor, the additive may have an amino acid sequence corresponding to the human form of the protein. The media described herein may further include additives such as stem cell factor, Flt-3 ligand, or thrombopoietin, any of which may be derived from, or correspond to, the human form of the protein. While any of the media additives described herein may be derived from, or correspond to, the human form, this is not necessarily required and additives that are derived from, or correspond to, those of other mammals may also be acceptable.

The cells, media, methods of producing the described cells, and related methods of use are more fully discussed herein.

BRIEF DESCRIPTION OF THE DRAWINGS

FIGS. 1A-1D show analysis of pluripotency markers (SSEA-4, Tra-1-60, Oct4, and Nanog) on iPSCs derived from fibroblasts by immunofluorescence staining. FIGS. 1E-1G show analysis of pluripotency markers (Oct3/4, Nanog, and Sox2) on iPSCs derived from fibroblasts by real time RT-PCR. FIGS. 1H-1I illustrate a karyotyping assay on hiPSCs by G-band. FIG. 1J illustrates bisulfite sequencing analysis of methylation in Nanog and Oct4 promoter. FIG. 1K-1M illustrate histologic detection in teratoma formation by Hematoxylin and eosin staining showing that hiPSCs are able to successfully differentiate into all three germ layers in vitro.

FIGS. 4A-4C provide a representative FACS diagrams of CD34 and CD31 expression in cells differentiated from normal hiPSCs. FIGS. 4D and 4E illustrate the timing of appearance of mesoderm precursors.

FIGS. 5A-5G. Validation of hiPSC-derived endothelial cells (UFECs) through mesoderm precursors. FIGS. 5A-5D demonstrate that hiPSC-derived UFECs generated through mesoderm precursors show typical endothelial cell morphology and express multiple EC markers (CD31, vWF, and CD144). FIGS. 5E-5G illustrate an in vitro functional angiogenesis assay for hiPSC-derived UFECs. hiPSC-derived UFECs formed vascular tube-like structures on Matrigel™.

FIGS. 6A-6K. Generation of Mesenchymal stem cells (iMSC) and smooth muscle cells (iSMCs) from hiPSCs through mesoderm precursor cells. FIG. 6A-6E. The representative phenotype of iMSC analyzed by FACS. FIG. 6F-6H. iMSC derived from hiPSCs through mesoderm precursor cells after osteogenic differentiation in vitro. FIG. 6I-K. Differentiation of hiPSC-derived mesoderm precursors into smooth muscle cells. The expression of SMC markers α-SMA, calponin, and SM22 was analyzed by FACS (FIG. 6I) and immunofluorescence staining (the cell nuclei were stained with DAPI (blue)).

FIG. 8A. The maximum number of CD45−CD34+CD31+ cells generated from iPSCs peaks at day 12 of culture (left); FIG. 8B. Timing of appearance of human CD34 and CD45. Cumulative number of CD45+CD34+CD31+ cells generated from the differentiation of iPSCs (right). FIGS. 8C and 8D. Generation of colony-forming units (CFU) 14 days after the incubation of day 12 hiPSC-derived suspension cells in semisolid clonogenic culture. Left: FIG. 8C. Number of CFU per $1\times10^3$ cells plated.

FIG. 8D. Representative erythroid (BFU-E), myeloid (CFU-GM) and mixed (CFU-GEMM) colonies.

DETAILED DESCRIPTION OF ILLUSTRATIVE EMBODIMENTS

Figure 1A:
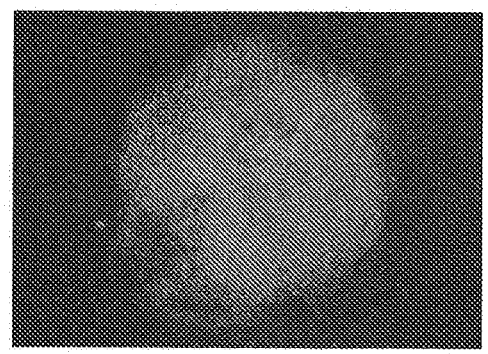
FIGS. 1A-1M. Characterization of hiPSC. Cells were derived and expanded in feeder free and defined medium.
Figure 1B:
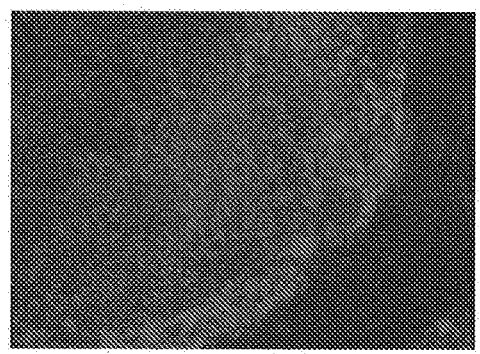
Figure 1C:
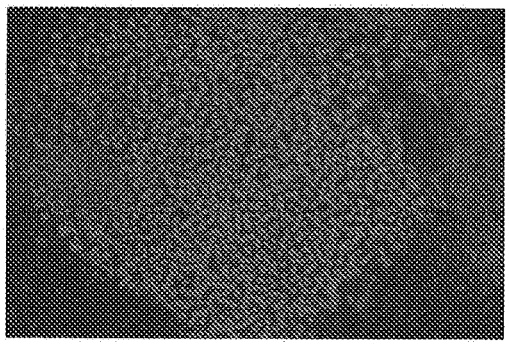
Figure 1D:
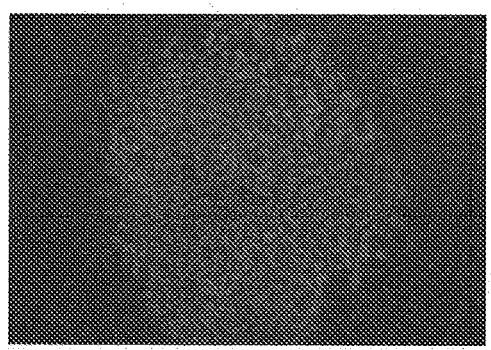
Figure 1E:
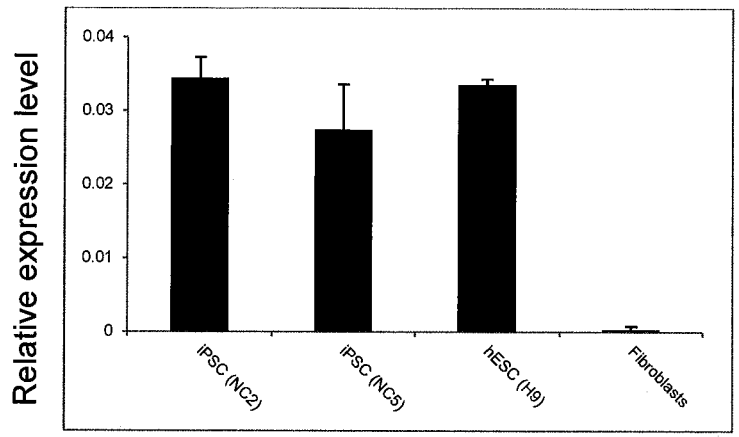
Figure 1F:
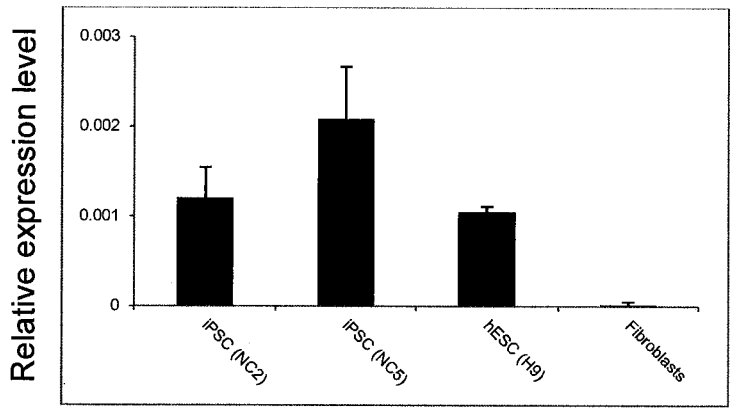
Figure 1G:
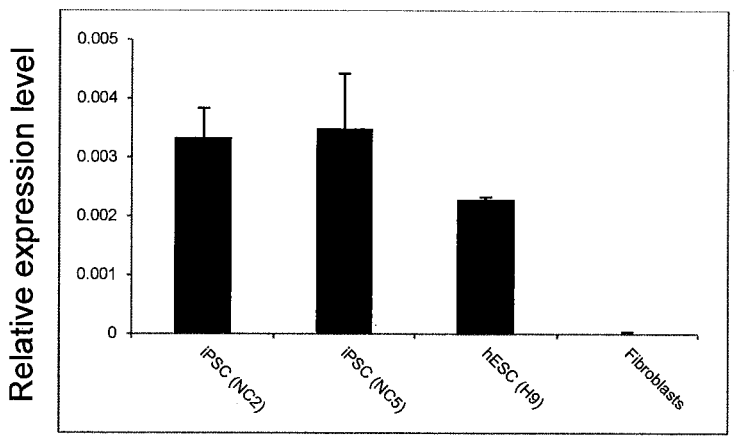
Figure 1H:
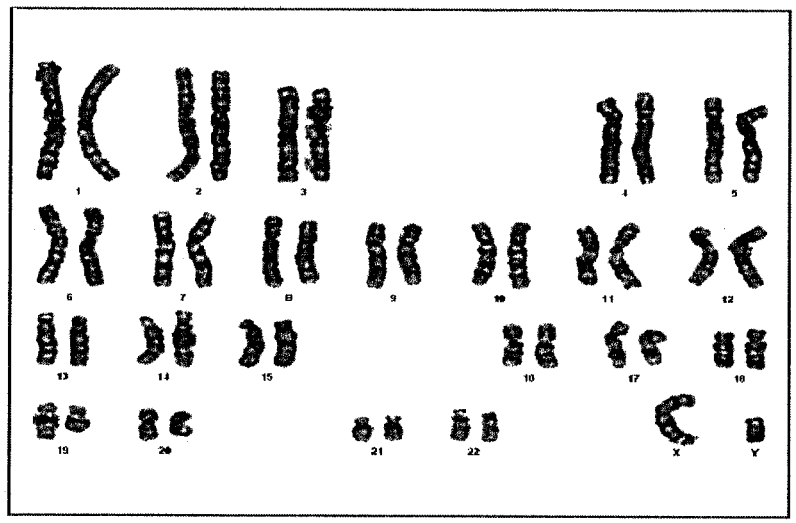
Figure 1I:
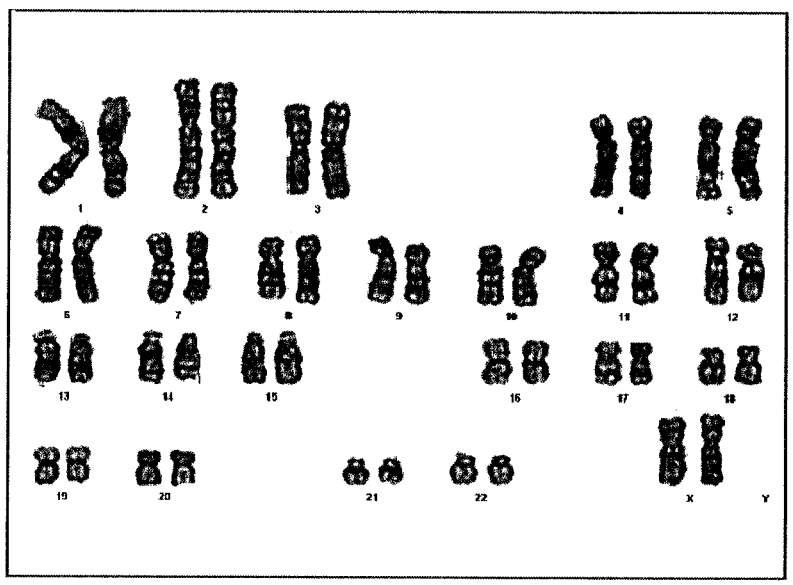
Figure 1J:
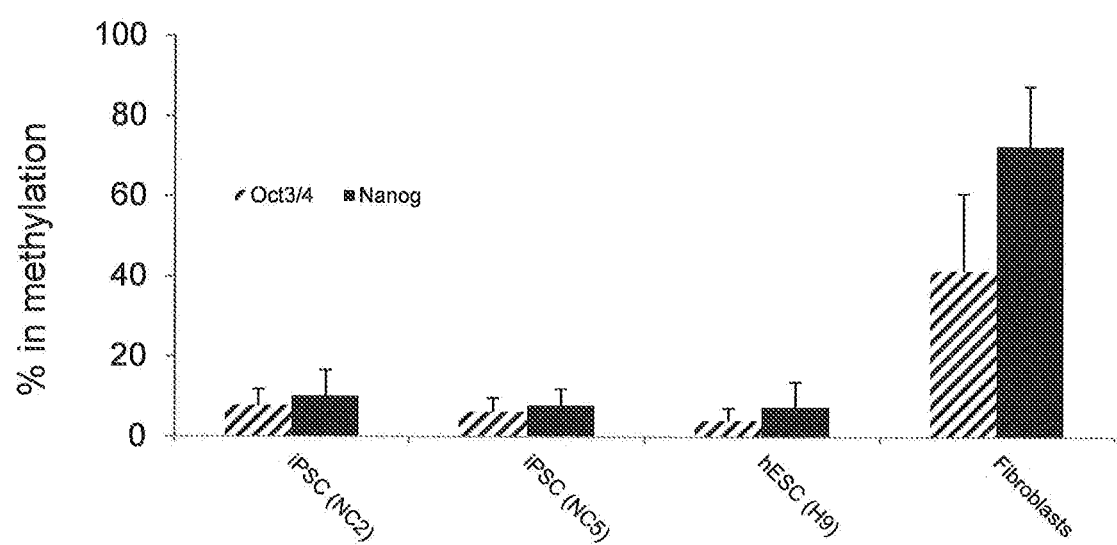
Figure 1K:
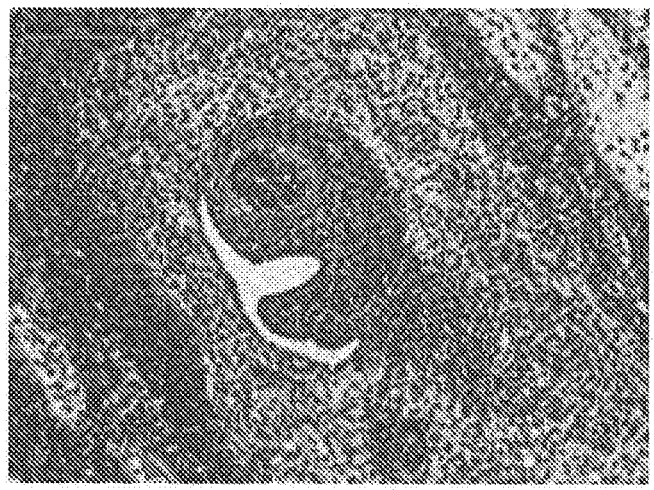
Figure 1L:
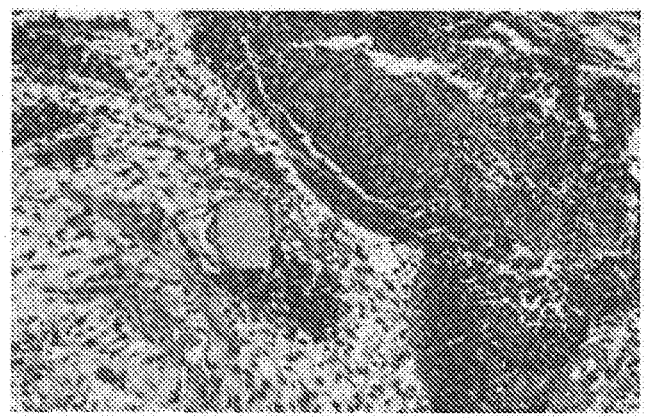
Figure 1M:
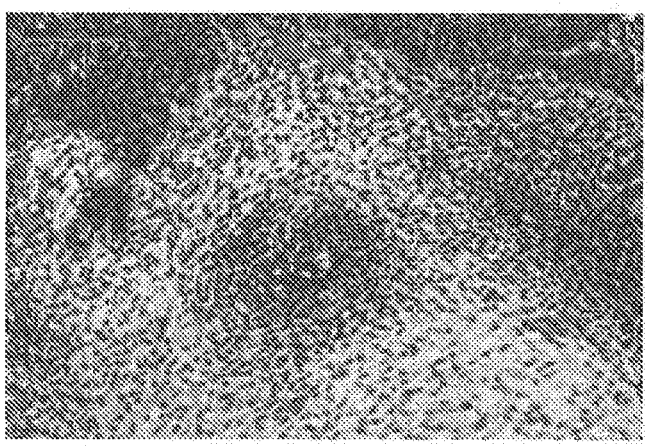

Described herein are cells, cell culture methods, and cell culture media compositions useful for producing and maintaining iPSC-derived cell lines that are of higher purity and maintain cell type integrity better than current iPSC-derived cell lines. Also disclosed are methods of using the described cells and media.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

The terms "treating," "treatment," and "therapy" refer to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The terms "induced pluripotent stem cell," "iPSC," and variants thereof (e.g., hiPSC) refer to pluripotent stem cells made recombinantly from a somatic cell by expressing certain transcription factors in the somatic cell, such that it becomes pluripotent. The transcription factors expressed in the somatic cell to induce this change are well known in the art; therefore, these terms are not limited to the particular embodiments of such cells described herein. Nor is the scope of these terms limited by the method used to overexpress these factors, be it transduction, transformation, or another means of exogenous gene expression.

The terms "MDM2" and "MDM+" are used interchangeably through this and previous applications.

Cell Culture Media

Provided herein are various cell culture media for culturing cells described herein and, in some cases, for promoting or allowing for cell differentiation. One type of medium described herein is basic mesoderm differentiation medium (MDM). In some embodiments MDM can serve as a cell culture medium. In other embodiments MDM can be used as a cell differentiation medium. In still further embodiments MDM may be both a culture medium and a cell differentiation medium. As those skilled in the art will understand, MDM can have many embodiments depending on the concentration of the components used in a given formulation. The primary components of MDM are provided in Table 1, while Table 2 provides a particular embodiment of the medium.

TABLE 1

Primary components of MDM

| Ingredient | Amount |
| --- | --- |
| Iscove's Modified Dulbecco's Medium (IMDM) mixed with Ham's F-12 Nutrient Mix, with L-alanyl-L-glutamine (GlutaMax ™) additive | About a 1:1 mixture |
| albumin | about 5 mg/ml |
| α-monothioglycerol | 350-450 µM |
| protein-free hybridoma mixture II | 5% |
| L-ascorbic acid 2-phosphate | about 50 µg/ml |
| (GlutaMax ™) | |
| L-alanyl-L-glutamine | about 1 mM to about 2 mM |
| Antibiotic (penicillin/streptomycin mix) | 50 units pen. 50 mg strep. |
| cholesterol lipids | about 1 µg/ml to about 4 µg/ml |

TABLE 1-continued

Primary components of MDM

| Ingredient | Amount |
| --- | --- |
| insulin-transferrin-selenium-ethanolamine supplement (Table 3) | about 0.5% to about 3% of total mixture |
| bone morphogenic protein 4 | about 10 ng/ml |
| vascular endothelial growth factor | about 10 ng/ml |
| basic fibroblast growth factor | About 10 to about 25 ng/ml |

TABLE 2

A single embodiment of MDM media, as exemplified in the Examples, below.

| Ingredient | Amount |
| --- | --- |
| Iscove's Modified Dulbecco's Medium (IMDM, Invitrogen, Catalog #: 21056-023) mixed with Ham's F-12 Nutrient Mix, with L-alanyl-L-glutamine (GlutaMax ™) additive (Invitrogen, Catalog #, 31765-035) | 1:1 mixture |
| Albucult ™ | 5 mg/ml |
| α-monothioglycerol (Sigma-Aldrich, Catalog #: M6145) | 3.9 µl per 100 ml |
| protein-free hybridoma mixture II (Invitrogen Catalog #: 12040-077) | 5% of total volume |
| L-ascorbic acid 2-phosphate (Sigma-Aldrich, Catalog #: A 8960) | 50 µg/ml |
| L-alanyl-L-glutamine (GlutaMax ™) (2 mM, Invitrogen, Catalog #: 35050061) | 2 mM |
| Antibiotic (Invitrogen, Catalog #: 15140122) | 50 units pen. 50 mg strep. |
| cholesterol lipids (Invitrogen, Catalog #: 12531018) | 2.2 µg/ml |
| insulin-transferrin-selenium-ethanolamine supplement (Invitrogen, Catalog #: 515000560) | 1% of total volume |
| bone morphogenic protein 4 (R & D systems, Catalog #: 314-BP-050) | 10 ng/ml |
| vascular endothelial growth factor (Invitrogen, Catalog #: PHC9394) | 10 ng/ml |
| basic fibroblast growth factor (Pepro Tech, Catalog #: 100-18B) | 10 ng/ml |

TABLE 3

Insulin-Transferrin-Selenium-Ethanolamine media supplement (ITS-X) (100X)

| Component | Molecular Weight (kD) | Concentration (mg/L) | mM |
| --- | --- | --- | --- |
| Insulin | 5.8 | 1,000 | 172.41379 |
| Transferrin | 80 | 550 | 6.875 |
| Sodium Selenite | 173 | 0.67 | 0.003873 |
| Ethanolamine | 61 | 200 | 3.278688 |

Also provided herein are various cell culture media for culturing cells described herein and, in some cases, for promoting or allowing for cell differentiation. Another type of medium described herein is basic mesoderm differentiation medium 1 (MDM1). In some embodiments MDM1 can serve as a cell culture medium. In other embodiments MDM1 can be used as a cell differentiation medium. In still further embodiments MDM1 may be both a culture medium and a cell differentiation medium. As those skilled in the art will understand, MDM1 can have many embodiments depending on the concentration of the components used in a given formulation. The primary components of MDM1 are provided in Table 4, while Table 5 provides a particular embodiment of the medium.

TABLE 4

Primary components of MDM1

| Ingredient | Amount |
| --- | --- |
| Iscove's Modified Dulbecco's Medium (IMDM) mixed with Ham's F-12 Nutrient Mix, with L-alanyl-L-glutamine (GlutaMax ™) additive | About a 1:1 mixture |
| Albumin | About 5 mg/ml |
| α-monothioglycerol | 350-450 μM |
| Protein-free hybridoma mixture II | 5% |
| L-ascorbic acid 2-phosphate (GlutaMax ™) | About 50 μg/ml |
| L-alanyl-L-glutamine | About 1 mM to 2 mM |
| Antibiotic (penicillin/streptomycin mix) | 50 units pen/ 50 mg strep |
| Insulin-transferrin-selenium-ethanolamine supplement | About 0.5% to 3% |
| Bone morphogenic protein 4 | About 10 ng/ml |
| Vascular endothelial growth factor | About 10 ng/ml |
| Basic fibroblast growth factor | About 10 to 25 ng/ml |

Those skilled in the art will understand that the MDM and MDM1 media described herein can be varied in a variety of ways. For example, one could perhaps add the individual components of IMDM to Ham's F-12 Nutrient Mix, with L-alanyl-L-glutamine additive to arrive at the first ingredient of the medium. Such variations are contemplated by the inventors and would only be available to the skilled artisan in view of the detailed description and data provided by the present application.

A variety of sources of the ingredients listed for MDM and MDM1 may also be used. In some embodiments albumin may be naturally produced human albumin. In another embodiment the listed albumin may be recombinant human albumin, such as Albucult®. In some embodiments albumin may be naturally produced bovine albumin. In another embodiment the listed albumin may be recombinant bovine albumin. In other embodiments the albumin used in MDM and MDM1 may be derived from another biological source. For example, the albumin used in MDM and MDM1 may be natural or recombinant albumin from a rodent, reptile, avian, canine, feline, primate, lagamorphs, didelphimorphs, insectivores, carnivores, and the like.

A variety of sources of the cholesterol lipids in MDM may also be used. In some embodiments the cholesterol lipids may be human cholesterol lipids. Alternatively, the cholesterol lipids may be murine cholesterol lipids. In other embodiments the cholesterol lipids used in MDM may be derived from another biological source. For example, the cholesterol lipids may be from a rodent, reptile, avian, canine, feline, primate, lagamorphs, didelphimorphs, insectivores, carnivores, and the like.

The insulin ingredient used for MDM and MDM1 may also be derived from a variety of sources. In some embodiments insulin may be naturally produced human insulin. In another embodiment the listed insulin may be recombinant human insulin. In other embodiments the insulin used in MDM and MDM1 may be derived from another biological source. For example, the insulin may be natural or recombinant insulin from a rodent, reptile, avian, canine, feline, primate, lagamorphs, didelphimorphs, insectivores, carnivores, and the like.

The transferrin ingredient used for MDM and MDM1 may also be derived from a variety of sources. In some embodiments transferrin may be naturally produced human transferrin. In another embodiment the listed transferrin may be recombinant human transferrin. In other embodiments the transferrin used in MDM and MDM1 may be derived from another biological source. For example, the transferrin may be natural or recombinant transferrin from a rodent, reptile, avian, canine, feline, primate, lagamorphs, didelphimorphs, insectivores, carnivores, and the like.

The bone morphogenic protein 4 (BMP4) ingredient used for MDM and MDM1 may also be derived from a variety of sources. In some embodiments BMP4 may be naturally produced human BMP4. In another embodiment the listed BMP4 may be recombinant human BMP4. In other embodiments the BMP4 used in MDM and MDM1 may be derived from another biological source. For example, the BMP4 may be natural or recombinant BMP4 from a rodent, reptile, avian, canine, feline, primate, lagamorphs, didelphimorphs, insectivores, carnivores, and the like. Other BMPs may be used in place of, or in conjunction with BMP4. For example, BMP1, BMP2, BMP3, BMP5, BMP7, BMP8a, and BMP15 are all known to be involved in various aspects of tissue development or differentiation. Thus, those skilled in the art will understand, in view of the present disclosure, that the MDM and MDM1 described herein could also be supplemented with these proteins, depending on the cells being cultured or the differentiation path desired. As described above, these BMPs could also be naturally produced human BMP, recombinant human BMP, or a natural or recombinant BMP from a rodent, reptile, avian, canine, feline, primate, lagamorphs, didelphimorphs, insectivores, carnivores, or other such animal.

The vascular endothelial growth factor (VEGF) ingredient used for MDM and MDM1 may also be derived from a variety of sources. In some embodiments VEGF may be naturally produced human VEGF. In another embodiment the listed VEGF may be recombinant human VEGF. In other embodiments the VEGF used in MDM and MDM1 may be derived from another biological source. For example, the VEGF may be natural or recombinant VEGF from a rodent, reptile, avian, canine, feline, primate, lagamorphs, didelphimorphs, insectivores, carnivores, and the like.

The basic fibroblast growth factor (bFGF) ingredient used for MDM and MDM1 may also be derived from a variety of sources. In some embodiments bFGF may be naturally produced human bFGF. In another embodiment the listed bFGF may be recombinant human bFGF. In other embodiments the bFGF used in MDM and MDM1 may be derived from another biological source. For example, the bFGF may be natural or recombinant bFGF from a rodent, reptile, avian, canine, feline, primate, lagamorphs, didelphimorphs, insectivores, carnivores, and the like.

The MDM and MDM1 described herein can also be supplemented with additional ingredients to alter or enhance the function of the media. For example, in other embodiments the MDM and MDM1 can be modified to hematopoietic differentiation medium (MDM+ and MDM1+, respectively) by adding stem cell factor (SCF), Flt-3 ligand, and thrombopoietin to the medium. In other embodiments the MDM and MDM1 can be modified by adding SCF and thrombopoietin to the medium. In other embodiments the MDM and MDM1 can be modified by adding SCF and Flt-3 ligand to the medium. In other embodiments, the MDM and MDM1 can be modified by adding thrombopoietin and Flt-3 ligand to the medium. Alternatively, the MDM and MDM1 can be modified by adding only SCF to the medium. In other embodiments, the MDM and MDM1 can be modified by adding only Flt-3 ligand to the medium. In other embodiments, the MDM and MDM1 can be modified by adding only thrombopoietin to the medium. In particular embodiments, MDM and MDM1 can be supplemented with recombinant human SCF (Stemcell Technologies Inc.) at 100 ng/ml, recombinant human Flt-3 ligand (Stemcell Technologies Inc.) at 100 ng/ml, and recombinant human thrombopoietin (Stemcell Technologies Inc.) at 100 ng/ml. The MDM+medium referred to in the examples section provided herein is formulated by supplementing the MDM from Table 2 with recombinant human SCF (Stemcell Technologies Inc.) at 100 ng/ml, recombinant human Flt-3 ligand (Stemcell Technologies Inc.) at 100 ng/ml, and recombinant human thrombopoietin (Stemcell Technologies Inc.) at 100 ng/ml. The MDM1+ medium referred to in the examples section provided herein is formulated by supplementing the MDM1 from Table 4 with recombinant human SCF (Stemcell Technologies Inc.) at 50 ng/ml, recombinant human Flt-3 ligand (Stemcell Technologies Inc.) at 50 ng/ml, and recombinant human thrombopoietin (Stemcell Technologies Inc.) at 50 ng/ml.

The SCF ingredient used herein may be derived from a variety of sources. In some embodiments SCF may be naturally produced human SCF. In another embodiment the listed SCF may be recombinant human SCF. In some embodiments SCF may be naturally produced murine SCF. In another embodiment the listed SCF may be recombinant murine SCF. In other embodiments the SCF used in MDM and MDM1 may be derived from another biological source. For example, the SCF may be natural or recombinant SCF from a rodent, reptile, avian, canine, feline, primate, lagamorphs, didelphimorphs, insectivores, carnivores, and the like.

The thrombopoietin ingredient described herein may be derived from a variety of sources. In some embodiments thrombopoietin may be naturally produced human thrombopoietin. In another embodiment the listed thrombopoietin may be recombinant human thrombopoietin. In some embodiments thrombopoietin may be naturally produced murine thrombopoietin. In another embodiment the listed thrombopoietin may be recombinant murine thrombopoietin. In other embodiments the thrombopoietin used in MDM and MDM1 may be derived from another biological source. For example, the thrombopoietin may be natural or recombinant thrombopoietin from a rodent, reptile, avian, canine, feline, primate, lagamorphs, didelphimorphs, insectivores, carnivores, and the like.

The Flt-3 ligand ingredient used herein may be derived from a variety of sources. In some embodiments Flt-3 ligand may be naturally produced human Flt-3 ligand. In another embodiment the listed Flt-3 ligand may be recombinant human Flt-3 ligand. In some embodiments Flt-3 ligand may be naturally produced murine Flt-3 ligand. In another embodiment the listed Flt-3 ligand may be recombinant murine Flt-3 ligand. In other embodiments the Flt-3 ligand used in MDM and MDM1 may be derived from another biological source. For example, the Flt-3 ligand may be natural or recombinant Flt-3 ligand from a rodent, reptile, avian, canine, feline, primate, lagamorphs, didelphimorphs, insectivores, carnivores, and the like.

Despite the possibilities for having various sources for the ingredients listed for MDM and MDM1 and MDM- and MDM1-derived media, there is no requirement that all of the MDM MDM1 protein components, for example, be derived from the same source. Thus, one MDM or MDM1 formulation might have transferrin that is obtained from a natural human source, recombinant human insulin, murine BMP4, and canine VEGF. This is not to say, however, that all of these ingredients could not be from the same source in a different MDM or MDM1 formulation.

One ingredient that may be used in the media described herein is Protein Free Hybridoma Medium II (PFHM II), which is a serum-free, protein-free medium that contains no polypeptide growth or attachment factors, or mediators that may complicate downstream processing and final product purification.

The media described herein can be supplemented with an antibiotic to prevent contamination by bacteria. Suitable antibiotics for tissue culture applications are known in the art. For example, penicillin and streptomycin, or a combination thereof (pen/strep) are commonly used. Anti-fungal agents may also be used to prevent fungal contamination. Suitable anti-fungal agents for tissue culture applications are known in the art.

The media ingredients listed herein may be used within a range of concentrations described herein without negatively affecting the performance of the media. The mixture of Iscove's Modified Dulbecco's Medium (IMDM) mixed with Ham's F-12 Nutrient Mix with GlutaMax™ additive is listed above as being combined in about a 1:1 ratio (i.e., about a 50% to 50% mixture); however, these ingredients can be mixed in other ratios as well. In some embodiments, the mixture of Iscove's Modified Dulbecco's Medium (IMDM) mixed with Ham's F-12 Nutrient Mix with GlutaMax™ additive is about 30% to 70% mixture. In some embodiments, the mixture of Iscove's Modified Dulbecco's Medium (IMDM) mixed with Ham's F-12 Nutrient Mix with GlutaMax™ additive is about 35% to 65% mixture. In some embodiments, the mixture of Iscove's Modified Dulbecco's Medium (IMDM) mixed with Ham's F-12 Nutrient Mix with GlutaMax™ additive is about 40% to 60% mixture. In some embodiments, the mixture of Iscove's Modified Dulbecco's Medium (IMDM) mixed with Ham's F-12 Nutrient Mix with GlutaMax™ additive is about 45% to 55% mixture. In some embodiments, the mixture of Iscove's Modified Dulbecco's Medium (IMDM) mixed with Ham's F-12 Nutrient Mix with GlutaMax™ additive is about 70% to 30% mixture. In some embodiments, the mixture of Iscove's Modified Dulbecco's Medium (IMDM) mixed with Ham's F-12 Nutrient Mix with GlutaMax™ additive is about 65% to 35% mixture. In some embodiments, the mixture of Iscove's Modified Dulbecco's Medium (IMDM) mixed with Ham's F-12 Nutrient Mix with GlutaMax™ additive is about 60% to 40% mixture. In some embodiments, the mixture of Iscove's Modified Dulbecco's Medium (IMDM) mixed with Ham's F-12 Nutrient Mix with GlutaMax™ additive is about 55% to 45% mixture. Any of these concentrations may be combined with the other ingredients provided herein at any of their listed concentrations as well and may be used in any MDM, or MDM+, MDM1, or MDM1+ media described herein or any medium derived therefrom.

The concentration of albumin listed Table 1 and 4 is about 5 mg/ml; however, this ingredient may be used at other concentrations without negatively affecting the performance of the medium. In one embodiment the concentration of albumin in MDM, MDM+, MDM1, or MDM1+ is about 5 mg/ml. In one embodiment the concentration of albumin in MDM, MDM+, MDM1, or MDM1+ is about 1 mg/ml. In one embodiment the concentration of albumin in MDM, MDM+, MDM1, or MDM1+ is about 2 mg/ml. In one embodiment the concentration of albumin in MDM, MDM+, MDM1, or MDM1+ is about 3 mg/ml. In one embodiment the concentration of albumin in MDM, MDM+, MDM1, or MDM1+ is about 4 mg/ml. In one embodiment the concentration of albumin in MDM, MDM+, MDM1, or MDM1+ is about 6 mg/ml. In one embodiment the concentration of albumin in MDM, MDM+, MDM1, or MDM1+ is about 7 mg/ml. In one embodiment the concentration of albumin in MDM, MDM+, MDM1, or MDM1+ is about 8 mg/ml. In one embodiment the concentration of albumin in MDM, MDM+, MDM1, or MDM1+ is about 9 mg/ml. In one embodiment the concentration of albumin in MDM, MDM+, MDM1, or MDM1+ is about 10 mg/ml. Any of these concentrations may be combined with the other ingredients provided herein at any of their listed concentrations as well and may be used in any MDM, MDM+, MDM1, or MDM1+ media described herein or any medium derived therefrom.

The concentration of α-monothioglycerol listed Table 1 and Table 4 is from about 350 µM to about 450 µM; however, this ingredient may be used at other concentrations without negatively affecting the performance of the medium. In one embodiment the concentration of α-monothioglycerol in MDM, MDM+, MDM1, or MDM1+ is about 350 µM. In one embodiment the concentration of α-monothioglycerol in MDM, MDM+, MDM1, or MDM1+ is about 360 µM. In one embodiment the concentration of α-monothioglycerol in MDM, MDM+, MDM1, or MDM1+ is about 370 µM. In one embodiment the concentration of α-monothioglycerol in MDM, MDM+, MDM1, or MDM1+ is about 380 µM. In one embodiment the concentration of α-monothioglycerol MDM, MDM+, MDM1, or MDM1+ is about 390 µM. In one embodiment the concentration of α-monothioglycerol in MDM, MDM+, MDM1, or MDM1+ is about 400 µM. In one embodiment the concentration of α-monothioglycerol in MDM, MDM+, MDM1, or MDM1+ is about 410 µM. In one embodiment the concentration of α-monothioglycerol in MDM, or MDM+, MDM1, or MDM1+ is about 420 µM. In one embodiment the concentration of α-monothioglycerol in MDM, or MDM+, MDM1, or MDM1+ is about 430 µM. In one embodiment the concentration of α-monothioglycerol in MDM, or MDM+, MDM1, or MDM1+ is about 440 µM. In one embodiment the concentration of α-monothioglycerol in MDM, or MDM+, MDM1, or MDM1+ is about 450 µM. Any of these concentrations may be combined with the other ingredients provide herein at any of their listed concentrations as well and may be used in any MDM, or MDM+, MDM1, or MDM1+ media described herein or any medium derived therefrom.

The concentration of L-alanyl-L-glutamine listed Table 1 and Table 4 is from about 1 mM to about 2 mM; however, this ingredient may be used at other concentrations without negatively affecting the performance of the medium. In one embodiment the concentration of L-alanyl-L-glutamine in MDM, or MDM+, MDM1, or MDM1+ is about 0.3 mM. In one embodiment the concentration of L-alanyl-L-glutamine in MDM, or MDM+, MDM1, or MDM1+ is about 0.6 mM. In one embodiment the concentration of L-alanyl-L-glutamine in MDM, or MDM+, MDM1, or MDM1+ is about 1 mM. In one embodiment the concentration of L-alanyl-L-glutamine in MDM, or MDM+, MDM1, or MDM1+ is about 1.3 mM. In one embodiment the concentration of L-alanyl-L-glutamine MDM, or MDM+, MDM1, or MDM1+ is about 1.6 mM. In one embodiment the concentration of L-alanyl-L-glutamine MDM, or MDM+, MDM1, or MDM1+ is about 2 mM. Any of these concentrations may be combined with the other ingredients provided herein at any of their listed concentrations as well and may be used in any MDM, or MDM+, MDM1, or MDM1+ media described herein or any medium derived therefrom.

The concentration of cholesterol lipids listed Table 1 is from about 1 µg/ml to about 4 µg/ml; however, this ingredient may be used at other concentrations without negatively affecting the performance of the medium. In one embodiment the concentration of cholesterol lipids in MDM, or MDM+ is about 1 µg/ml. In one embodiment the concentration of cholesterol lipids in MDM, or MDM+ is about 2 µg/ml. In one embodiment the concentration of cholesterol lipids in MDM, or MDM+, is about 3 µg/ml. In one embodiment the concentration of cholesterol lipids in MDM, or MDM+ is about 4 µg/ml. In one embodiment the concentration of cholesterol lipids MDM, or MDM+, MDM1, or MDM1+ is about 2.2 µg/ml. Any of these concentrations may be combined with the other ingredients provided herein at any of their listed concentrations as well and may be used in any MDM, or MDM+, MDM1, or MDM1+ media described herein or any medium derived therefrom.

The concentration of L-ascorbic acid 2-phosphate listed Table 1 or Table 4 is about 50 µg/ml; however, this ingredient may be used at other concentrations without negatively affecting the performance of the medium. In one embodiment the concentration of L-ascorbic acid 2-phosphate in MDM, or MDM+, MDM1, or MDM1+ is about 30 µg/ml. In one embodiment the concentration of L-ascorbic acid 2-phosphate in MDM, or MDM+, MDM1, or MDM1+ is about 40 µg/ml. In one embodiment the concentration of L-ascorbic acid 2-phosphate in MDM, or MDM+, MDM1, or MDM1+ is about 45 µg/ml. In one embodiment the concentration of L-ascorbic acid 2-phosphate in MDM, or MDM+, MDM1, or MDM1+ is about 50 µg/ml. In one embodiment the concentration of L-ascorbic acid 2-phosphate MDM, or MDM+, MDM1, or MDM1+ is about 55 µg/ml. In one embodiment the concentration of L-ascorbic acid 2-phosphate MDM, or MDM+, MDM1, or MDM1+ is about 60 µg/ml. In one embodiment the concentration of L-ascorbic acid 2-phosphate MDM, or MDM+, MDM1, or MDM1+ is about 65 µg/ml. In one embodiment the concentration of L-ascorbic acid 2-phosphate MDM, or MDM+, MDM1, or MDM1+ is about 70 µg/ml. Any of these concentrations may be combined with the other ingredients provided herein at any of their listed concentrations as well and may be used in any MDM, or MDM+, MDM1, or MDM1+ media described herein or any medium derived therefrom.

The concentration of BMP4 listed Table 1 or Table 4 is about 10 ng/ml; however, this ingredient may be used at other concentrations without negatively affecting the performance of the medium. In one embodiment the concentration of BMP4 in MDM, or MDM+, MDM1, or MDM1+ is about 3 ng/ml. In one embodiment the concentration of BMP4 in MDM, or MDM+, MDM1, or MDM1+ is about 6 ng/ml. In one embodiment the concentration of BMP4 in MDM, or MDM+, MDM1, or MDM1+ is about 10 ng/ml. In one embodiment the concentration of BMP4 in MDM, or MDM+, MDM1, or MDM1+ is about 13 ng/ml. In one embodiment the concentration of BMP4 MDM, or MDM+, MDM1, or MDM1+ is about 16 ng/ml. In one embodiment the concentration of BMP4 MDM, or MDM+, MDM1, or MDM1+ is about 20 ng/ml. Any of these concentrations may be combined with the other ingredients provided herein at any of their listed concentrations as well and may be used in any MDM, or MDM+, MDM1, or MDM1+ media described herein or any medium derived therefrom.

The concentration of VEGF listed Table 1 or Table 4 is about 10 ng/ml; however, this ingredient may be used at other concentrations without negatively affecting the performance of the medium. In one embodiment the concentration of VEGF in MDM, or MDM+, MDM1, or MDM1+ is about 3 ng/ml. In one embodiment the concentration of VEGF in MDM, or MDM+, MDM1, or MDM1+ is about 6 ng/ml. In one embodiment the concentration of VEGF in MDM, or MDM+, MDM1, or MDM1+ is about 10 ng/ml. In one embodiment the concentration of VEGF in MDM, or MDM+, MDM1, or MDM1+ is about 13 ng/ml. In one embodiment the concentration of VEGF MDM, or MDM+, MDM1, or MDM1+ is about 16 ng/ml. In one embodiment the concentration of VEGF MDM, or MDM+, MDM1, or MDM1+ is about 20 ng/ml. Any of these concentrations may be combined with the other ingredients provided herein at any of their listed concentrations as well and may be used in any MDM, or MDM+, MDM1, or MDM1+ media described herein or any medium derived therefrom.

The concentration of bFGF listed Table 1 or Table 4 is from about 10 ng/ml to about 25 ng/ml; however, this ingredient may be used at other concentrations without negatively affecting the performance of the medium. In one embodiment the concentration of bFGF in MDM, or MDM+, MDM1, or MDM1+ is about 3 ng/ml. In one embodiment the concentration of bFGF in MDM, or MDM+, MDM1, or MDM1+ is about 6 ng/ml. In one embodiment the concentration of bFGF in MDM, or MDM+, MDM1, or MDM1+ is about 7 ng/ml. In one embodiment the concentration of bFGF in MDM, or MDM+, MDM1, or MDM1+ is about 10 ng/ml. In one embodiment the concentration of bFGF MDM, or MDM+, MDM1, or MDM1+ is about 15 ng/ml. In one embodiment the concentration of bFGF MDM, or MDM+, MDM1, or MDM1+ is about 20 ng/ml. In one embodiment the concentration of bFGF MDM, or MDM+, MDM1, or MDM1+ is about 25 ng/ml. In one embodiment the concentration of bFGF MDM, or MDM+, MDM1, or MDM1+ is about 30 ng/ml. In one embodiment the concentration of bFGF MDM, or MDM+, MDM1, or MDM1+ is about 35 ng/ml. Any of these concentrations may be combined with the other ingredients provided herein at any of their listed concentrations as well and may be used in any MDM, or MDM+, MDM1, or MDM1+ media described herein or any medium derived therefrom.

The concentration of SCF used in MDM+ is about 100 ng/ml. The concentration of SCF used in MDM1+ is about 50 ng/ml. However, this ingredient may be used at other concentrations without negatively affecting the performance of the medium. In addition, SCF may be used to supplement MDM and MDM1, alone or in combination with other additives, as discussed herein. In one embodiment the concentration of SCF in MDM, or MDM+, MDM1, or MDM1+ is about 75 ng/ml. In one embodiment the concentration of SCF in MDM, or MDM+, MDM1, or MDM1+ is about 80 ng/ml. In one embodiment the concentration of SCF in MDM, or MDM+, MDM1, or MDM1+ is about 85 ng/ml. In one embodiment the concentration of SCF in MDM, or MDM+, MDM1, or MDM1+ is about 90 ng/ml. In one embodiment the concentration of SCF MDM, or MDM+, MDM1, or MDM1+ is about 95 ng/ml. In one embodiment the concentration of SCF MDM, or MDM+, MDM1, or MDM1+ is about 100 ng/ml. In one embodiment the concentration of SCF MDM, or MDM+, MDM1, or MDM1+ is about 105 ng/ml. In one embodiment the concentration of SCF MDM, or MDM+, MDM1, or MDM1+ is about 110 ng/ml. In one embodiment the concentration of SCF MDM, or MDM+, MDM1, or MDM1+ is about 115 ng/ml. In one embodiment the concentration of SCF MDM, or MDM+, MDM1, or MDM1+ is about 120 ng/ml. In one embodiment the concentration of SCF MDM, or MDM+, MDM1, or MDM1+ is about 125 ng/ml. Any of these concentrations may be combined with the other ingredients provided herein at any of their listed concentrations as well and may be used in any MDM, or MDM+, MDM1, or MDM1+ media described herein or any medium derived therefrom.

The concentration of Flt-3 ligand used in MDM+ is about 100 ng/ml. The concentration of Flt-3 ligand used in MDM1+ is about 50 ng/ml however, this ingredient may be used at other concentrations without negatively affecting the performance of the medium. In addition, Flt-3 ligand may be used to supplement MDM and MDM1, alone or in combination with other additives, as discussed herein. In one embodiment the concentration of Flt-3 ligand in MDM, or MDM+, MDM1, or MDM1+ is about 75 ng/ml. In one embodiment the concentration of Flt-3 ligand in MDM, or MDM+, MDM1, or MDM1+ is about 80 ng/ml. In one embodiment the concentration of Flt-3 ligand in MDM, or MDM+, MDM1, or MDM1+ is about 85 ng/ml. In one embodiment the concentration of Flt-3 ligand in MDM, or MDM+, MDM1, or MDM1+ is about 90 ng/ml. In one embodiment the concentration of Flt-3 ligand MDM, or MDM+, MDM1, or MDM1+ is about 95 ng/ml. In one embodiment the concentration of Flt-3 ligand MDM, or MDM+, MDM1, or MDM1+ is about 100 ng/ml. In one embodiment the concentration of Flt-3 ligand MDM, or MDM+, MDM1, or MDM1+ is about 105 ng/ml. In one embodiment the concentration of Flt-3 ligand MDM, or MDM+, MDM1, or MDM1+ is about 110 ng/ml. In one embodiment the concentration of Flt-3 ligand MDM, or MDM+, MDM1, or MDM1+ is about 115 ng/ml. In one embodiment the concentration of Flt-3 ligand MDM, or MDM+, MDM1, or MDM1+ is about 120 ng/ml. In one embodiment the concentration of Flt-3 ligand MDM, or MDM+, MDM1, or MDM1+ is about 125 ng/ml. Any of these concentrations may be combined with the other ingredients provide herein at any of their listed concentrations as well and may be used in any MDM, or MDM+, MDM1, or MDM1+ media described herein or any medium derived therefrom.

The concentration of thrombopoietin in MDM+ is about 100 ng/ml. The concentration of thrombopoietin in MDM1+ is about 50 ng/ml. However, this ingredient may be used at other concentrations without negatively affecting the performance of the medium. In addition, thrombopoietin may be used to supplement MDM, and MDM1, alone or in combination with other additives, as discussed herein. In one embodiment the concentration of thrombopoietin in MDM, or MDM+, MDM1, or MDM1+ is about 75 ng/ml. In one embodiment the concentration of thrombopoietin in MDM, or MDM+, MDM1, or MDM1+ is about 80 ng/ml. In one embodiment the concentration of thrombopoietin in MDM, or MDM+, MDM1, or MDM1+ is about 85 ng/ml. In one embodiment the concentration of thrombopoietin in MDM, or MDM+, MDM1, or MDM1+ is about 90 ng/ml. In one embodiment the concentration of thrombopoietin MDM, or MDM+, MDM1, or MDM1+ is about 95 ng/ml. In one embodiment the concentration of thrombopoietin MDM, or MDM+, MDM1, or MDM1+ is about 100 ng/ml. In one embodiment the concentration of thrombopoietin MDM, or MDM+, MDM1, or MDM1+ is about 105 ng/ml. In one embodiment the concentration of thrombopoietin MDM, or MDM+, MDM1, or MDM1+ is about 110 ng/ml. In one embodiment the concentration of thrombopoietin MDM, or MDM+, MDM1, or MDM1+ is about 115 ng/ml. In one embodiment the concentration of thrombopoietin MDM, or MDM+, MDM1, or MDM1+ is about 120 ng/ml. In one embodiment the concentration of thrombopoietin MDM, or MDM+, MDM1, or MDM1+ is about 125 ng/ml. Any of these concentrations may be combined with the other ingredients provided herein at any of their listed concentrations as well and may be used in any MDM, or MDM+, MDM1, or MDM1+ media described herein or any medium derived therefrom.

The media described herein may have an amount of protein-free hybridoma mixture II. For example, the final MDM, or MDM+, MDM1, or MDM1+ medium, or a derivative medium, may have protein-free hybridoma mixture II is about 5% of the total medium formulation. Other concentrations may be used without negatively affecting the performance of the medium. In one embodiment protein-free hybridoma mixture II is about 2% of the total medium formulation. In one embodiment protein-free hybridoma mixture II is about 3% of the total medium formulation. In another embodiment protein-free hybridoma mixture II is about 4% of the total medium formulation. In one embodiment protein-free hybridoma mixture II is about 5% of the total medium formulation. In another embodiment protein-free hybridoma mixture II is about 6% of the total medium. In one embodiment protein-free hybridoma mixture II is about 7% of the total medium formulation. In one embodiment protein-free hybridoma mixture II is about 8% of the total medium formulation. In one embodiment protein-free hybridoma mixture II is about 9% of the total medium formulation. In another embodiment protein-free hybridoma mixture II is about 10% of the total medium formulation. Any of these concentrations may be combined with the other ingredients provided herein at any of their listed concentrations as well and may be used in any MDM, or MDM+, MDM1, or MDM1+ media described herein or any medium derived therefrom.

Methods of Culturing Cells and Promoting Cell Differentiation

The media compositions and formulations described herein may be used for culturing cells. In some embodiments the described media compositions and formulations may be used to maintain or expand cells in culture. In other embodiments the described media compositions and formulations may be used to culture cells in a manner that promotes their differentiation into a different cell type. In another embodiment the described media compositions and formulations may be used to culture cells in a manner that promotes their differentiation into a different cell type and then the same medium, or a similar medium derivative, may be used to culture the differentiated cell. Furthermore, the described media compositions and formulations may be used to culture cells in a manner that promotes their differentiation into a different cell type and then the same medium, or a similar medium derivative, may be used to culture the differentiated cell in a manner that allows the cell to differentiate further. Methods for carrying out these culture techniques are described herein. In view of the description of these culture methods, certain modifications, based on existing culture techniques, will be readily apparent to those skilled in the art, such variations of the described methods are considered to be within the scope of this disclosure.

Provided herein are methods for producing a mesodermal precursor cell from an iPSC. In one embodiment the mesodermal precursor cell is produced by culturing an iPSC in the MDM or MDM1 medium described herein for a period of at least 5 days, in the absence of feeder cells. In one embodiment the mesodermal precursor cell is produced by culturing an iPSC in the MDM or MDM1 medium described herein for a period of at least 5 days, in the presence of feeder cells. In one embodiment the mesodermal precursor cell is produced by culturing an iPSC in the MDM or MDM1 medium described herein for a period of at least 5 days, in the presence of a basement membrane matrix, in the absence of feeder cells. In one embodiment the mesodermal precursor cell is produced by culturing an iPSC in the MDM or MDM1 medium described herein for a period of at least 5 days, in the presence of a basement membrane matrix, in the presence of feeder cells. In one embodiment the mesodermal precursor cell is produced by culturing an iPSC in the MDM or MDM1 medium described herein for a period of at least 5 days, in the absence of a basement membrane matrix, in the absence of feeder cells. In one embodiment the mesodermal precursor cell is produced by culturing an iPSC in the MDM or MDM1 medium described herein for a period of at least 5 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 6 days, in the absence of feeder cells. In one embodiment the mesodermal precursor cell is produced by culturing an iPSC in the MDM or MDM1 medium described herein for a period of at least 6 days, in the presence of feeder cells. In one embodiment the mesodermal precursor cell is produced by culturing an iPSC in the MDM or MDM1 medium described herein for a period of at least 6 days, in the presence of a basement membrane matrix, in the absence of feeder cells. In one embodiment the mesodermal precursor cell is produced by culturing an iPSC in the MDM or MDM1 medium described herein for a period of at least 6 days, in the presence of a basement membrane matrix, in the presence of feeder cells. In one embodiment the mesodermal precursor cell is produced by culturing an iPSC in the MDM or MDM1 medium described herein for a period of at least 6 days, in the absence of a basement membrane matrix, in the absence of feeder cells. In one embodiment the mesodermal precursor cell is produced by culturing an iPSC in the MDM or MDM1 medium described herein for a period of at least 6 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 7 days, in the absence of feeder cells. In one embodiment the mesodermal precursor cell is produced by culturing an iPSC in the MDM or MDM1 medium described herein for a period of at least 7 days, in the presence of feeder cells. In one embodiment the mesodermal precursor cell is produced by culturing an iPSC in the MDM or MDM1 medium described herein for a period of at least 7 days, in the presence of a basement membrane matrix, in the absence of feeder cells. In one embodiment the mesodermal precursor cell is produced by culturing an iPSC in the MDM or MDM1 medium described herein for a period of at least 7 days, in the presence of a basement membrane matrix, in the presence of feeder cells. In one embodiment the mesodermal precursor cell is produced by culturing an iPSC in the MDM or MDM1 medium described herein for a period of at least 7 days, in the absence of a basement membrane matrix, in the absence of feeder cells. In one embodiment the mesodermal precursor cell is produced by culturing an iPSC in the MDM or MDM1 medium described herein for a period of at least 7 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 8 days, in the absence of feeder cells. In one embodiment the mesodermal precursor cell is produced by culturing an iPSC in the MDM or MDM1 medium described herein for a period of at least 8 days, in the presence of feeder cells. In one embodiment the mesodermal precursor cell is produced by culturing an iPSC in the MDM or MDM1 medium described herein for a period of at least 8 days, in the presence of a basement membrane matrix, in the absence of feeder cells. In one embodiment the mesodermal precursor cell is produced by culturing an iPSC in the MDM or MDM1 medium described herein for a period of at least 8 days, in the presence of a basement membrane matrix, in the presence of feeder cells. In one embodiment the mesodermal precursor cell is produced by culturing an iPSC in the MDM or MDM1 medium described herein for a period of at least 8 days, in the absence of a basement membrane matrix, in the absence of feeder cells. In one embodiment the mesodermal precursor cell is produced by culturing an iPSC in the MDM or MDM1 medium described herein for a period of at least 8 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 9 days, in the absence of feeder cells. In one embodiment the mesodermal precursor cell is produced by culturing an iPSC in the MDM or MDM1 medium described herein for a period of at least 9 days, in the presence of feeder cells. In one embodiment the mesodermal precursor cell is produced by culturing an iPSC in the MDM or MDM1 medium described herein for a period of at least 9 days, in the presence of a basement membrane matrix, in the absence of feeder cells. In one embodiment the mesodermal precursor cell is produced by culturing an iPSC in the MDM or MDM1 medium described herein for a period of at least 9 days, in the presence of a basement membrane matrix, in the presence of feeder cells. In one embodiment the mesodermal precursor cell is produced by culturing an iPSC in the MDM or MDM1 medium described herein for a period of at least 9 days, in the absence of a basement membrane matrix, in the absence of feeder cells. In one embodiment the mesodermal precursor cell is produced by culturing an iPSC in the MDM or MDM1 medium described herein for a period of at least 9 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 10 days, in the absence of feeder cells. In one embodiment the mesodermal precursor cell is produced by culturing an iPSC in the MDM or MDM1 medium described herein for a period of at least 10 days, in the presence of feeder cells. In one embodiment the mesodermal precursor cell is produced by culturing an iPSC in the MDM or MDM1 medium described herein for a period of at least 10 days, in the presence of a basement membrane matrix, in the absence of feeder cells. In one embodiment the mesodermal precursor cell is produced by culturing an iPSC in the MDM or MDM1 medium described herein for a period of at least 10 days, in the presence of a basement membrane matrix, in the presence of feeder cells. In one embodiment the mesodermal precursor cell is produced by culturing an iPSC in the MDM or MDM1 medium described herein for a period of at least 10 days, in the absence of a basement membrane matrix, in the absence of feeder cells. In one embodiment the mesodermal precursor cell is produced by culturing an iPSC in the MDM or MDM1 medium described herein for a period of at least 10 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 11 days, in the absence of feeder cells. In one embodiment the mesodermal precursor cell is produced by culturing an iPSC in the MDM or MDM1 medium described herein for a period of at least 11 days, in the presence of feeder cells. In one embodiment the mesodermal precursor cell is produced by culturing an iPSC in the MDM or MDM1 medium described herein for a period of at least 11 days, in the presence of a basement membrane matrix, in the absence of feeder cells. In one embodiment the mesodermal precursor cell is produced by culturing an iPSC in the MDM or MDM1 medium described herein for a period of at least 11 days, in the presence of a basement membrane matrix, in the presence of feeder cells. In one embodiment the mesodermal precursor cell is produced by culturing an iPSC in the MDM or MDM1 medium described herein for a period of at least 11 days, in the absence of a basement membrane matrix, in the absence of feeder cells. In one embodiment the mesodermal precursor cell is produced by culturing an iPSC in the MDM or MDM1 medium described herein for a period of at least 11 days, in the absence of a basement membrane matrix, in the presence of feeder cells.

Provided herein are method for producing a mesodermal precursor cell from an iPSC. In one embodiment the mesodermal precursor cell is produced by culturing an iPSC in the MDM or MDM1 medium described herein for a period of at least 12 days, in the absence of feeder cells. In one embodiment the mesodermal precursor cell is produced by culturing an iPSC in the MDM or MDM1 medium described herein for a period of at least 12 days, in the presence of feeder cells. In one embodiment the mesodermal precursor cell is produced by culturing an iPSC in the MDM or MDM1 medium described herein for a period of at least 12 days, in the presence of a basement membrane matrix, in the absence of feeder cells. In one embodiment the mesodermal precursor cell is produced by culturing an iPSC in the MDM or MDM1 medium described herein for a period of at least 12 days, in the presence of a basement membrane matrix, in the presence of feeder cells. In one embodiment the mesodermal precursor cell is produced by culturing an iPSC in the MDM or MDM1 medium described herein for a period of at least 12 days, in the absence of a basement membrane matrix, in the absence of feeder cells. In one embodiment the mesodermal precursor cell is produced by culturing an iPSC in the MDM or MDM1 medium described herein for a period of at least 12 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 13 days, in the absence of feeder cells. In one embodiment the mesodermal precursor cell is produced by culturing an iPSC in the MDM or MDM1 medium described herein for a period of at least 13 days, in the presence of feeder cells. In one embodiment the mesodermal precursor cell is produced by culturing an iPSC in the MDM or MDM1 medium described herein for a period of at least 13 days, in the presence of a basement membrane matrix, in the absence of feeder cells. In one embodiment the mesodermal precursor cell is produced by culturing an iPSC in the MDM or MDM1 medium described herein for a period of at least 13 days, in the presence of a basement membrane matrix, in the presence of feeder cells. In one embodiment the mesodermal precursor cell is produced by culturing an iPSC in the MDM or MDM1 medium described herein for a period of at least 13 days, in the absence of a basement membrane matrix, in the absence of feeder cells. In one embodiment the mesodermal precursor cell is produced by culturing an iPSC in the MDM or MDM1 medium described herein for a period of at least 13 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 14 days, in the absence of feeder cells. In one embodiment the mesodermal precursor cell is produced by culturing an iPSC in the MDM or MDM1 medium described herein for a period of at least 14 days, in the presence of feeder cells. In one embodiment the mesodermal precursor cell is produced by culturing an iPSC in the MDM or MDM1 medium described herein for a period of at least 14 days, in the presence of a basement membrane matrix, in the absence of feeder cells. In one embodiment the mesodermal precursor cell is produced by culturing an iPSC in the MDM or MDM1 medium described herein for a period of at least 14 days, in the presence of a basement membrane matrix, in the presence of feeder cells. In one embodiment the mesodermal precursor cell is produced by culturing an iPSC in the MDM or MDM1 medium described herein for a period of at least 14 days, in the absence of a basement membrane matrix, in the absence of feeder cells. In one embodiment the mesodermal precursor cell is produced by culturing an iPSC in the MDM or MDM1 medium described herein for a period of at least 14 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 15 days, in the absence of feeder cells. In one embodiment the mesodermal precursor cell is produced by culturing an iPSC in the MDM or MDM1 medium described herein for a period of at least 15 days, in the presence of feeder cells. In one embodiment the mesodermal precursor cell is produced by culturing an iPSC in the MDM or MDM1 medium described herein for a period of at least 15 days, in the presence of a basement membrane matrix, in the absence of feeder cells. In one embodiment the mesodermal precursor cell is produced by culturing an iPSC in the MDM or MDM1 medium described herein for a period of at least 15 days, in the presence of a basement membrane matrix, in the presence of feeder cells. In one embodiment the mesodermal precursor cell is produced by culturing an iPSC in the MDM or MDM1 medium described herein for a period of at least 15 days, in the absence of a basement membrane matrix, in the absence of feeder cells. In one embodiment the mesodermal precursor cell is produced by culturing an iPSC in the MDM or MDM1 medium described herein for a period of at least 15 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 16 days, in the absence of feeder cells. In one embodiment the mesodermal precursor cell is produced by culturing an iPSC in the MDM or MDM1 medium described herein for a period of at least 16 days, in the presence of feeder cells. In one embodiment the mesodermal precursor cell is produced by culturing an iPSC in the MDM or MDM1 medium described herein for a period of at least 16 days, in the presence of a basement membrane matrix, in the absence of feeder cells. In one embodiment the mesodermal precursor cell is produced by culturing an iPSC in the MDM or MDM1 medium described herein for a period of at least 16 days, in the presence of a basement membrane matrix, in the presence of feeder cells. In one embodiment the mesodermal precursor cell is produced by culturing an iPSC in the MDM or MDM1 medium described herein for a period of at least 16 days, in the absence of a basement membrane matrix, in the absence of feeder cells. In one embodiment the mesodermal precursor cell is produced by culturing an iPSC in the MDM or MDM1 medium described herein for a period of at least 16 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 17 days, in the absence of feeder cells. In one embodiment the mesodermal precursor cell is produced by culturing an iPSC in the MDM or MDM1 medium described herein for a period of at least 17 days, in the presence of feeder cells. In one embodiment the mesodermal precursor cell is produced by culturing an iPSC in the MDM or MDM1 medium described herein for a period of at least 17 days, in the presence of a basement membrane matrix, in the absence of feeder cells. In one embodiment the mesodermal precursor cell is produced by culturing an iPSC in the MDM or MDM1 medium described herein for a period of at least 17 days, in the presence of a basement membrane matrix, in the presence of feeder cells. In one embodiment the mesodermal precursor cell is produced by culturing an iPSC in the MDM or MDM1 medium described herein for a period of at least 17 days, in the absence of a basement membrane matrix, in the absence of feeder cells. In one embodiment the mesodermal precursor cell is produced by culturing an iPSC in the MDM or MDM1 medium described herein for a period of at least 17 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 18 days, in the absence of feeder cells. In one embodiment the mesodermal precursor cell is produced by culturing an iPSC in the MDM or MDM1 medium described herein for a period of at least 18 days, in the presence of feeder cells. In one embodiment the mesodermal precursor cell is produced by culturing an iPSC in the MDM or MDM1 medium described herein for a period of at least 18 days, in the presence of a basement membrane matrix, in the absence of feeder cells. In one embodiment the mesodermal precursor cell is produced by culturing an iPSC in the MDM or MDM1 medium described herein for a period of at least 18 days, in the presence of a basement membrane matrix, in the presence of feeder cells. In one embodiment the mesodermal precursor cell is produced by culturing an iPSC in the MDM or MDM1 medium described herein for a period of at least 18 days, in the absence of a basement membrane matrix, in the absence of feeder cells. In one embodiment the mesodermal precursor cell is produced by culturing an iPSC in the MDM or MDM1 medium described herein for a period of at least 18 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 19 days, in the absence of feeder cells. In one embodiment the mesodermal precursor cell is produced by culturing an iPSC in the MDM or MDM1 medium described herein for a period of at least 19 days, in the presence of feeder cells. In one embodiment the mesodermal precursor cell is produced by culturing an iPSC in the MDM or MDM1 medium described herein for a period of at least 19 days, in the presence of a basement membrane matrix, in the absence of feeder cells. In one embodiment the mesodermal precursor cell is produced by culturing an iPSC in the MDM or MDM1 medium described herein for a period of at least 19 days, in the presence of a basement membrane matrix, in the presence of feeder cells. In one embodiment the mesodermal precursor cell is produced by culturing an iPSC in the MDM or MDM1 medium described herein for a period of at least 19 days, in the absence of a basement membrane matrix, in the absence of feeder cells. In one embodiment the mesodermal precursor cell is produced by culturing an iPSC in the MDM or MDM1 medium described herein for a period of at least 19 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 20 days, in the absence of feeder cells. In one embodiment the mesodermal precursor cell is produced by culturing an iPSC in the MDM or MDM1 medium described herein for a period of at least 20 days, in the presence of feeder cells. In one embodiment the mesodermal precursor cell is produced by culturing an iPSC in the MDM or MDM1 medium described herein for a period of at least 20 days, in the presence of a basement membrane matrix, in the absence of feeder cells. In one embodiment the mesodermal precursor cell is produced by culturing an iPSC in the MDM or MDM1 medium described herein for a period of at least 20 days, in the presence of a basement membrane matrix, in the presence of feeder cells. In one embodiment the mesodermal precursor cell is produced by culturing an iPSC in the MDM or MDM1 medium described herein for a period of at least 20 days, in the absence of a basement membrane matrix, in the absence of feeder cells. In one embodiment the mesodermal precursor cell is produced by culturing an iPSC in the MDM or MDM1 medium described herein for a period of at least 20 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for at least 2 passages, in the absence of feeder cells. In one embodiment the mesodermal precursor cell is produced by culturing an iPSC in the MDM or MDM1 medium described herein for at least 2 passages, in the presence of feeder cells. In one embodiment the mesodermal precursor cell is produced by culturing an iPSC in the MDM or MDM1 medium described herein for at least 2 passages, in the presence of a basement membrane matrix, in the absence of feeder cells. In one embodiment the mesodermal precursor cell is produced by culturing an iPSC in the MDM or MDM1 medium described herein for at least 2 passages, in the presence of a basement membrane matrix, in the presence of feeder cells. In one embodiment the mesodermal precursor cell is produced by culturing an iPSC in the MDM or MDM1 medium described herein for at least 2 passages, in the absence of a basement membrane matrix, in the absence of feeder cells. In one embodiment the mesodermal precursor cell is produced by culturing an iPSC in the MDM or MDM1 medium described herein for at least 2 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for at least 3 passages, in the absence of feeder cells. In one embodiment the mesodermal precursor cell is produced by culturing an iPSC in the MDM or MDM1 medium described herein for at least 3 passages, in the presence of feeder cells. In one embodiment the mesodermal precursor cell is produced by culturing an iPSC in the MDM or MDM1 medium described herein for at least 3 passages, in the presence of a basement membrane matrix, in the absence of feeder cells. In one embodiment the mesodermal precursor cell is produced by culturing an iPSC in the MDM or MDM1 medium described herein for at least 3 passages, in the presence of a basement membrane matrix, in the presence of feeder cells. In one embodiment the mesodermal precursor cell is produced by culturing an iPSC in the MDM or MDM1 medium described herein for at least 3 passages, in the absence of a basement membrane matrix, in the absence of feeder cells. In one embodiment the mesodermal precursor cell is produced by culturing an iPSC in the MDM or MDM1 medium described herein for at least 3 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for at least 4 passages, in the absence of feeder cells. In one embodiment the mesodermal precursor cell is produced by culturing an iPSC in the MDM or MDM1 medium described herein for at least 4 passages, in the presence of feeder cells. In one embodiment the mesodermal precursor cell is produced by culturing an iPSC in the MDM or MDM1 medium described herein for at least 4 passages, in the presence of a basement membrane matrix, in the absence of feeder cells. In one embodiment the mesodermal precursor cell is produced by culturing an iPSC in the MDM or MDM1 medium described herein for at least 4 passages, in the presence of a basement membrane matrix, in the presence of feeder cells. In one embodiment the mesodermal precursor cell is produced by culturing an iPSC in the MDM or MDM1 medium described herein for at least 4 passages, in the absence of a basement membrane matrix, in the absence of feeder cells. In one embodiment the mesodermal precursor cell is produced by culturing an iPSC in the MDM or MDM1 medium described herein for at least 4 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for at least 5 passages, in the absence of feeder cells. In one embodiment the mesodermal precursor cell is produced by culturing an iPSC in the MDM or MDM1 medium described herein for at least 5 passages, in the presence of feeder cells. In one embodiment the mesodermal precursor cell is produced by culturing an iPSC in the MDM or MDM1 medium described herein for at least 5 passages, in the presence of a basement membrane matrix, in the absence of feeder cells. In one embodiment the mesodermal precursor cell is produced by culturing an iPSC in the MDM or MDM1 medium described herein for at least 5 passages, in the presence of a basement membrane matrix, in the presence of feeder cells. In one embodiment the mesodermal precursor cell is produced by culturing an iPSC in the MDM or MDM1 medium described herein for at least 5 passages, in the absence of a basement membrane matrix, in the absence of feeder cells. In one embodiment the mesodermal precursor cell is produced by culturing an iPSC in the MDM or MDM1 medium described herein for at least 5 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for at least 6 passages, in the absence of feeder cells. In one embodiment the mesodermal precursor cell is produced by culturing an iPSC in the MDM or MDM1 medium described herein for at least 6 passages, in the presence of feeder cells. In one embodiment the mesodermal precursor cell is produced by culturing an iPSC in the MDM or MDM1 medium described herein for at least 6 passages, in the presence of a basement membrane matrix, in the absence of feeder cells. In one embodiment the mesodermal precursor cell is produced by culturing an iPSC in the MDM or MDM1 medium described herein for at least 6 passages, in the presence of a basement membrane matrix, in the presence of feeder cells. In one embodiment the mesodermal precursor cell is produced by culturing an iPSC in the MDM or MDM1 medium described herein for at least 6 passages, in the absence of a basement membrane matrix, in the absence of feeder cells. In one embodiment the mesodermal precursor cell is produced by culturing an iPSC in the MDM or MDM1 medium described herein for at least 6 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for at least 7 passages, in the absence of feeder cells. In one embodiment the mesodermal precursor cell is produced by culturing an iPSC in the MDM or MDM1 medium described herein for at least 7 passages, in the presence of feeder cells. In one embodiment the mesodermal precursor cell is produced by culturing an iPSC in the MDM or MDM1 medium described herein for at least 7 passages, in the presence of a basement membrane matrix, in the absence of feeder cells. In one embodiment the mesodermal precursor cell is produced by culturing an iPSC in the MDM or MDM1 medium described herein for at least 7 passages, in the presence of a basement membrane matrix, in the presence of feeder cells. In one embodiment the mesodermal precursor cell is produced by culturing an iPSC in the MDM or MDM1 medium described herein for at least 7 passages, in the absence of a basement membrane matrix, in the absence of feeder cells. In one embodiment the mesodermal precursor cell is produced by culturing an iPSC in the MDM or MDM1 medium described herein for at least 7 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of at least 5 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 5 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 5 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 5 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 5 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 5 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 6 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 6 days, in the presence of feeder cells, such that the differentiated mesodermal precursor cells express CD31 and CD34, but not CD45, but not CD45. In one embodiment the mesodermal precursor cell is produced by culturing an iPSC in the MDM or MDM1 medium described herein for a period of at least 6 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 6 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 6 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 6 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 7 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 7 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 7 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 7 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 7 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 7 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 8 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 8 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 8 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 8 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 8 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 8 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 9 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 9 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 9 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 9 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 9 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 9 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 10 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 10 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 10 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 10 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 10 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 10 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 11 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 11 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 11 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 11 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 11 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 11 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 12 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 12 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 12 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 12 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 12 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 12 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 13 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 13 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 13 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 13 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 13 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 13 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 14 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 14 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 14 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 14 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 14 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 14 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 15 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 15 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 15 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 15 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 15 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 15 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 16 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 16 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 16 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 16 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 16 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 16 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 17 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 17 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 17 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 17 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 17 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 17 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 18 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 18 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 18 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 18 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 18 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 18 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 19 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 19 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 19 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 19 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 19 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 19 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of at least 20 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 20 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 20 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 20 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 20 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of at least 20 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for at least 2 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 2 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 2 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 2 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 2 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 2 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for at least 3 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 3 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 3 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 3 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 3 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 3 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for at least 4 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 4 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 4 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 4 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 4 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 4 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for at least 5 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 5 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 5 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 5 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 5 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 5 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for at least 6 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 6 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 6 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 6 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 6 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 6 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for at least 7 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 7 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 7 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 7 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 7 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for at least 7 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 5 days, in the absence of feeder cells. In one embodiment the mesodermal precursor cell is produced by culturing an iPSC in the MDM or MDM1 medium described herein for a period of 5 days, in the presence of feeder cells. In one embodiment the mesodermal precursor cell is produced by culturing an iPSC in the MDM or MDM1 medium described herein for a period of 5 days, in the presence of a basement membrane matrix, in the absence of feeder cells. In one embodiment the mesodermal precursor cell is produced by culturing an iPSC in the MDM or MDM1 medium described herein for a period of 5 days, in the presence of a basement membrane matrix, in the presence of feeder cells. In one embodiment the mesodermal precursor cell is produced by culturing an iPSC in the MDM or MDM1 medium described herein for a period of 5 days, in the absence of a basement membrane matrix, in the absence of feeder cells. In one embodiment the mesodermal precursor cell is produced by culturing an iPSC in the MDM or MDM1 medium described herein for a period of 5 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 6 days, in the absence of feeder cells. In one embodiment the mesodermal precursor cell is produced by culturing an iPSC in the MDM or MDM1 medium described herein for a period of 6 days, in the presence of feeder cells. In one embodiment the mesodermal precursor cell is produced by culturing an iPSC in the MDM or MDM1 medium described herein for a period of 6 days, in the presence of a basement membrane matrix, in the absence of feeder cells. In one embodiment the mesodermal precursor cell is produced by culturing an iPSC in the MDM or MDM1 medium described herein for a period of 6 days, in the presence of a basement membrane matrix, in the presence of feeder cells. In one embodiment the mesodermal precursor cell is produced by culturing an iPSC in the MDM or MDM1 medium described herein for a period of 6 days, in the absence of a basement membrane matrix, in the absence of feeder cells. In one embodiment the mesodermal precursor cell is produced by culturing an iPSC in the MDM or MDM1 medium described herein for a period of 6 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 7 days, in the absence of feeder cells. In one embodiment the mesodermal precursor cell is produced by culturing an iPSC in the MDM or MDM1 medium described herein for a period of 7 days, in the presence of feeder cells. In one embodiment the mesodermal precursor cell is produced by culturing an iPSC in the MDM or MDM1 medium described herein for a period of 7 days, in the presence of a basement membrane matrix, in the absence of feeder cells. In one embodiment the mesodermal precursor cell is produced by culturing an iPSC in the MDM or MDM1 medium described herein for a period of 7 days, in the presence of a basement membrane matrix, in the presence of feeder cells. In one embodiment the mesodermal precursor cell is produced by culturing an iPSC in the MDM or MDM1 medium described herein for a period of 7 days, in the absence of a basement membrane matrix, in the absence of feeder cells. In one embodiment the mesodermal precursor cell is produced by culturing an iPSC in the MDM or MDM1 medium described herein for a period of 7 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 8 days, in the absence of feeder cells. In one embodiment the mesodermal precursor cell is produced by culturing an iPSC in the MDM or MDM1 medium described herein for a period of 8 days, in the presence of feeder cells. In one embodiment the mesodermal precursor cell is produced by culturing an iPSC in the MDM or MDM1 medium described herein for a period of 8 days, in the presence of a basement membrane matrix, in the absence of feeder cells. In one embodiment the mesodermal precursor cell is produced by culturing an iPSC in the MDM or MDM1 medium described herein for a period of 8 days, in the presence of a basement membrane matrix, in the presence of feeder cells. In one embodiment the mesodermal precursor cell is produced by culturing an iPSC in the MDM or MDM1 medium described herein for a period of 8 days, in the absence of a basement membrane matrix, in the absence of feeder cells. In one embodiment the mesodermal precursor cell is produced by culturing an iPSC in the MDM or MDM1 medium described herein for a period of 8 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 9 days, in the absence of feeder cells. In one embodiment the mesodermal precursor cell is produced by culturing an iPSC in the MDM or MDM1 medium described herein for a period of 9 days, in the presence of feeder cells. In one embodiment the mesodermal precursor cell is produced by culturing an iPSC in the MDM or MDM1 medium described herein for a period of 9 days, in the presence of a basement membrane matrix, in the absence of feeder cells. In one embodiment the mesodermal precursor cell is produced by culturing an iPSC in the MDM or MDM1 medium described herein for a period of 9 days, in the presence of a basement membrane matrix, in the presence of feeder cells. In one embodiment the mesodermal precursor cell is produced by culturing an iPSC in the MDM or MDM1 medium described herein for a period of 9 days, in the absence of a basement membrane matrix, in the absence of feeder cells. In one embodiment the mesodermal precursor cell is produced by culturing an iPSC in the MDM or MDM1 medium described herein for a period of 9 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 10 days, in the absence of feeder cells. In one embodiment the mesodermal precursor cell is produced by culturing an iPSC in the MDM or MDM1 medium described herein for a period of 10 days, in the presence of feeder cells. In one embodiment the mesodermal precursor cell is produced by culturing an iPSC in the MDM or MDM1 medium described herein for a period of 10 days, in the presence of a basement membrane matrix, in the absence of feeder cells. In one embodiment the mesodermal precursor cell is produced by culturing an iPSC in the MDM or MDM1 medium described herein for a period of 10 days, in the presence of a basement membrane matrix, in the presence of feeder cells. In one embodiment the mesodermal precursor cell is produced by culturing an iPSC in the MDM or MDM1 medium described herein for a period of 10 days, in the absence of a basement membrane matrix, in the absence of feeder cells. In one embodiment the mesodermal precursor cell is produced by culturing an iPSC in the MDM or MDM1 medium described herein for a period of 10 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 11 days, in the absence of feeder cells. In one embodiment the mesodermal precursor cell is produced by culturing an iPSC in the MDM or MDM1 medium described herein for a period of 11 days, in the presence of feeder cells. In one embodiment the mesodermal precursor cell is produced by culturing an iPSC in the MDM or MDM1 medium described herein for a period of 11 days, in the presence of a basement membrane matrix, in the absence of feeder cells. In one embodiment the mesodermal precursor cell is produced by culturing an iPSC in the MDM or MDM1 medium described herein for a period of 11 days, in the presence of a basement membrane matrix, in the presence of feeder cells. In one embodiment the mesodermal precursor cell is produced by culturing an iPSC in the MDM or MDM1 medium described herein for a period of 11 days, in the absence of a basement membrane matrix, in the absence of feeder cells. In one embodiment the mesodermal precursor cell is produced by culturing an iPSC in the MDM or MDM1 medium described herein for a period of 11 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 12 days, in the absence of feeder cells. In one embodiment the mesodermal precursor cell is produced by culturing an iPSC in the MDM or MDM1 medium described herein for a period of 12 days, in the presence of feeder cells. In one embodiment the mesodermal precursor cell is produced by culturing an iPSC in the MDM or MDM1 medium described herein for a period of 12 days, in the absence of a basement membrane matrix, in the absence of feeder cells. In one embodiment the mesodermal precursor cell is produced by culturing an iPSC in the MDM or MDM1 medium described herein for a period of 12 days, in the presence of a basement membrane matrix, in the presence of feeder cells. In one embodiment the mesodermal precursor cell is produced by culturing an iPSC in the MDM or MDM1 medium described herein for a period of 12 days, in the absence of a basement membrane matrix, in the absence of feeder cells. In one embodiment the mesodermal precursor cell is produced by culturing an iPSC in the MDM or MDM1 medium described herein for a period of 12 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 13 days, in the absence of feeder cells. In one embodiment the mesodermal precursor cell is produced by culturing an iPSC in the MDM or MDM1 medium described herein for a period of 13 days, in the presence of feeder cells. In one embodiment the mesodermal precursor cell is produced by culturing an iPSC in the MDM or MDM1 medium described herein for a period of 13 days, in the presence of a basement membrane matrix, in the absence of feeder cells. In one embodiment the mesodermal precursor cell is produced by culturing an iPSC in the MDM or MDM1 medium described herein for a period of 13 days, in the presence of a basement membrane matrix, in the presence of feeder cells. In one embodiment the mesodermal precursor cell is produced by culturing an iPSC in the MDM or MDM1 medium described herein for a period of 13 days, in the absence of a basement membrane matrix, in the absence of feeder cells. In one embodiment the mesodermal precursor cell is produced by culturing an iPSC in the MDM or MDM1 medium described herein for a period of 13 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 14 days, in the absence of feeder cells. In one embodiment the mesodermal precursor cell is produced by culturing an iPSC in the MDM or MDM1 medium described herein for a period of 14 days, in the presence of feeder cells. In one embodiment the mesodermal precursor cell is produced by culturing an iPSC in the MDM or MDM1 medium described herein for a period of 14 days, in the presence of a basement membrane matrix, in the absence of feeder cells. In one embodiment the mesodermal precursor cell is produced by culturing an iPSC in the MDM or MDM1 medium described herein for a period of 14 days, in the presence of a basement membrane matrix, in the presence of feeder cells. In one embodiment the mesodermal precursor cell is produced by culturing an iPSC in the MDM or MDM1 medium described herein for a period of 14 days, in the absence of a basement membrane matrix, in the absence of feeder cells. In one embodiment the mesodermal precursor cell is produced by culturing an iPSC in the MDM or MDM1 medium described herein for a period of 14 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 15 days, in the absence of feeder cells. In one embodiment the mesodermal precursor cell is produced by culturing an iPSC in the MDM or MDM1 medium described herein for a period of 15 days, in the presence of feeder cells. In one embodiment the mesodermal precursor cell is produced by culturing an iPSC in the MDM or MDM1 medium described herein for a period of 15 days, in the presence of a basement membrane matrix, in the absence of feeder cells. In one embodiment the mesodermal precursor cell is produced by culturing an iPSC in the MDM or MDM1 medium described herein for a period of 15 days, in the presence of a basement membrane matrix, in the presence of feeder cells. In one embodiment the mesodermal precursor cell is produced by culturing an iPSC in the MDM or MDM1 medium described herein for a period of 15 days, in the absence of a basement membrane matrix, in the absence of feeder cells. In one embodiment the mesodermal precursor cell is produced by culturing an iPSC in the MDM or MDM1 medium described herein for a period of 15 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 16 days, in the absence of feeder cells. In one embodiment the mesodermal precursor cell is produced by culturing an iPSC in the MDM or MDM1 medium described herein for a period of 16 days, in the presence of feeder cells. In one embodiment the mesodermal precursor cell is produced by culturing an iPSC in the MDM or MDM1 medium described herein for a period of 16 days, in the presence of a basement membrane matrix, in the absence of feeder cells. In one embodiment the mesodermal precursor cell is produced by culturing an iPSC in the MDM or MDM1 medium described herein for a period of 16 days, in the presence of a basement membrane matrix, in the presence of feeder cells. In one embodiment the mesodermal precursor cell is produced by culturing an iPSC in the MDM or MDM1 medium described herein for a period of 16 days, in the absence of a basement membrane matrix, in the absence of feeder cells. In one embodiment the mesodermal precursor cell is produced by culturing an iPSC in the MDM or MDM1 medium described herein for a period of 16 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 17 days, in the absence of feeder cells. In one embodiment the mesodermal precursor cell is produced by culturing an iPSC in the MDM or MDM1 medium described herein for a period of 17 days, in the presence of feeder cells. In one embodiment the mesodermal precursor cell is produced by culturing an iPSC in the MDM or MDM1 medium described herein for a period of 17 days, in the presence of a basement membrane matrix, in the absence of feeder cells. In one embodiment the mesodermal precursor cell is produced by culturing an iPSC in the MDM or MDM1 medium described herein for a period of 17 days, in the presence of a basement membrane matrix, in the presence of feeder cells. In one embodiment the mesodermal precursor cell is produced by culturing an iPSC in the MDM or MDM1 medium described herein for a period of 17 days, in the absence of a basement membrane matrix, in the absence of feeder cells. In one embodiment the mesodermal precursor cell is produced by culturing an iPSC in the MDM or MDM1 medium described herein for a period of 17 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 18 days, in the absence of feeder cells. In one embodiment the mesodermal precursor cell is produced by culturing an iPSC in the MDM or MDM1 medium described herein for a period of 18 days, in the presence of feeder cells. In one embodiment the mesodermal precursor cell is produced by culturing an iPSC in the MDM or MDM1 medium described herein for a period of 18 days, in the presence of a basement membrane matrix, in the absence of feeder cells. In one embodiment the mesodermal precursor cell is produced by culturing an iPSC in the MDM or MDM1 medium described herein for a period of 18 days, in the presence of a basement membrane matrix, in the presence of feeder cells. In one embodiment the mesodermal precursor cell is produced by culturing an iPSC in the MDM or MDM1 medium described herein for a period of 18 days, in the absence of a basement membrane matrix, in the absence of feeder cells. In one embodiment the mesodermal precursor cell is produced by culturing an iPSC in the MDM or MDM1 medium described herein for a period of 18 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 19 days, in the absence of feeder cells. In one embodiment the mesodermal precursor cell is produced by culturing an iPSC in the MDM or MDM1 medium described herein for a period of 19 days, in the presence of feeder cells. In one embodiment the mesodermal precursor cell is produced by culturing an iPSC in the MDM or MDM1 medium described herein for a period of 19 days, in the presence of a basement membrane matrix, in the absence of feeder cells. In one embodiment the mesodermal precursor cell is produced by culturing an iPSC in the MDM or MDM1 medium described herein for a period of 19 days, in the presence of a basement membrane matrix, in the presence of feeder cells. In one embodiment the mesodermal precursor cell is produced by culturing an iPSC in the MDM or MDM1 medium described herein for a period of 19 days, in the absence of a basement membrane matrix, in the absence of feeder cells. In one embodiment the mesodermal precursor cell is produced by culturing an iPSC in the MDM or MDM1 medium described herein for a period of 19 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 20 days, in the absence of feeder cells. In one embodiment the mesodermal precursor cell is produced by culturing an iPSC in the MDM or MDM1 medium described herein for a period of 20 days, in the presence of feeder cells. In one embodiment the mesodermal precursor cell is produced by culturing an iPSC in the MDM or MDM1 medium described herein for a period of 20 days, in the presence of a basement membrane matrix, in the absence of feeder cells. In one embodiment the mesodermal precursor cell is produced by culturing an iPSC in the MDM or MDM1 medium described herein for a period of 20 days, in the presence of a basement membrane matrix, in the presence of feeder cells. In one embodiment the mesodermal precursor cell is produced by culturing an iPSC in the MDM or MDM1 medium described herein for a period of 20 days, in the absence of a basement membrane matrix, in the absence of feeder cells. In one embodiment the mesodermal precursor cell is produced by culturing an iPSC in the MDM or MDM1 medium described herein for a period of 20 days, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for 2 passages, in the absence of feeder cells. In one embodiment the mesodermal precursor cell is produced by culturing an iPSC in the MDM or MDM1 medium described herein for 2 passages, in the presence of feeder cells. In one embodiment the mesodermal precursor cell is produced by culturing an iPSC in the MDM or MDM1 medium described herein for 2 passages, in the presence of a basement membrane matrix, in the absence of feeder cells. In one embodiment the mesodermal precursor cell is produced by culturing an iPSC in the MDM or MDM1 medium described herein for 2 passages, in the presence of a basement membrane matrix, in the presence of feeder cells. In one embodiment the mesodermal precursor cell is produced by culturing an iPSC in the MDM or MDM1 medium described herein for 2 passages, in the absence of a basement membrane matrix, in the absence of feeder cells. In one embodiment the mesodermal precursor cell is produced by culturing an iPSC in the MDM or MDM1 medium described herein for 2 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for 3 passages, in the absence of feeder cells. In one embodiment the mesodermal precursor cell is produced by culturing an iPSC in the MDM or MDM1 medium described herein for 3 passages, in the presence of feeder cells. In one embodiment the mesodermal precursor cell is produced by culturing an iPSC in the MDM or MDM1 medium described herein for 3 passages, in the presence of a basement membrane matrix, in the absence of feeder cells. In one embodiment the mesodermal precursor cell is produced by culturing an iPSC in the MDM or MDM1 medium described herein for 3 passages, in the presence of a basement membrane matrix, in the presence of feeder cells. In one embodiment the mesodermal precursor cell is produced by culturing an iPSC in the MDM or MDM1 medium described herein for 3 passages, in the absence of a basement membrane matrix, in the absence of feeder cells. In one embodiment the mesodermal precursor cell is produced by culturing an iPSC in the MDM or MDM1 medium described herein for 3 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for 4 passages, in the absence of feeder cells. In one embodiment the mesodermal precursor cell is produced by culturing an iPSC in the MDM or MDM1 medium described herein for 4 passages, in the presence of feeder cells. In one embodiment the mesodermal precursor cell is produced by culturing an iPSC in the MDM or MDM1 medium described herein for 4 passages, in the presence of a basement membrane matrix, in the absence of feeder cells. In one embodiment the mesodermal precursor cell is produced by culturing an iPSC in the MDM or MDM1 medium described herein for 4 passages, in the presence of a basement membrane matrix, in the presence of feeder cells. In one embodiment the mesodermal precursor cell is produced by culturing an iPSC in the MDM or MDM1 medium described herein for 4 passages, in the absence of a basement membrane matrix, in the absence of feeder cells. In one embodiment the mesodermal precursor cell is produced by culturing an iPSC in the MDM or MDM1 medium described herein for 4 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for 5 passages, in the absence of feeder cells. In one embodiment the mesodermal precursor cell is produced by culturing an iPSC in the MDM or MDM1 medium described herein for 5 passages, in the presence of feeder cells. In one embodiment the mesodermal precursor cell is produced by culturing an iPSC in the MDM or MDM1 medium described herein for 5 passages, in the presence of a basement membrane matrix, in the absence of feeder cells. In one embodiment the mesodermal precursor cell is produced by culturing an iPSC in the MDM or MDM1 medium described herein for 5 passages, in the presence of a basement membrane matrix, in the presence of feeder cells. In one embodiment the mesodermal precursor cell is produced by culturing an iPSC in the MDM or MDM1 medium described herein for 5 passages, in the absence of a basement membrane matrix, in the absence of feeder cells. In one embodiment the mesodermal precursor cell is produced by culturing an iPSC in the MDM or MDM1 medium described herein for 5 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for 6 passages, in the absence of feeder cells. In one embodiment the mesodermal precursor cell is produced by culturing an iPSC in the MDM or MDM1 medium described herein for 6 passages, in the presence of feeder cells. In one embodiment the mesodermal precursor cell is produced by culturing an iPSC in the MDM or MDM1 medium described herein for 6 passages, in the presence of a basement membrane matrix, in the absence of feeder cells. In one embodiment the mesodermal precursor cell is produced by culturing an iPSC in the MDM or MDM1 medium described herein for 6 passages, in the presence of a basement membrane matrix, in the presence of feeder cells. In one embodiment the mesodermal precursor cell is produced by culturing an iPSC in the MDM or MDM1 medium described herein for 6 passages, in the absence of a basement membrane matrix, in the absence of feeder cells. In one embodiment the mesodermal precursor cell is produced by culturing an iPSC in the MDM or MDM1 medium described herein for 6 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for 7 passages, in the absence of feeder cells. In one embodiment the mesodermal precursor cell is produced by culturing an iPSC in the MDM or MDM1 medium described herein for 7 passages, in the presence of feeder cells. In one embodiment the mesodermal precursor cell is produced by culturing an iPSC in the MDM or MDM1 medium described herein for 7 passages, in the presence of a basement membrane matrix, in the absence of feeder cells. In one embodiment the mesodermal precursor cell is produced by culturing an iPSC in the MDM or MDM1 medium described herein for 7 passages, in the presence of a basement membrane matrix, in the presence of feeder cells. In one embodiment the mesodermal precursor cell is produced by culturing an iPSC in the MDM or MDM1 medium described herein for 7 passages, in the absence of a basement membrane matrix, in the absence of feeder cells. In one embodiment the mesodermal precursor cell is produced by culturing an iPSC in the MDM or MDM1 medium described herein for 7 passages, in the absence of a basement membrane matrix, in the presence of feeder cells.

Provided herein are methods for producing a mesodermal precursor cell from an iPSC. In one embodiment the mesodermal precursor cell is produced by culturing an iPSC in the MDM or MDM1 medium described herein for a period of 5 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 5 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 5 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 5 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 5 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 5 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 6 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 6 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 6 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 6 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 6 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 6 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 7 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 7 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 7 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 7 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 7 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 7 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 8 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 8 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 8 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 8 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 8 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 8 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 9 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 9 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 9 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 9 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 9 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 9 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 10 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 10 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 10 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 10 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 10 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 10 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 11 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 11 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 11 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 11 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 11 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 11 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 12 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 12 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 12 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 12 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 12 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 12 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 13 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 13 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 13 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 13 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 13 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 13 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 14 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 14 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 14 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 14 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 14 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 14 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 15 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 15 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 15 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 15 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 15 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 15 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 16 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 16 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 16 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 16 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 16 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 16 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 17 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 17 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 17 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 17 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 17 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 17 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 18 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 18 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 18 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 18 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 18 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 18 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 19 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 19 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 19 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 19 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 19 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 19 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for a period of 20 days, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 20 days, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 20 days, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 20 days, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 20 days, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for a period of 20 days, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for 2 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 2 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 2 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 2 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 2 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 2 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for 3 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 3 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 3 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 3 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 3 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 3 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for 4 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 4 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 4 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 4 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 4 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 4 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for 5 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 5 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 5 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 5 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 5 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 5 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for 6 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 6 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 6 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 6 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 6 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 6 passages, in the absence of a basement membrane matrix, in the presence of feeder cells, such that the differentiated mesodermal precursor cells express CD31 and CD34, but not CD45.

Provided herein are methods for producing a mesodermal precursor cell from an iPSC. In one embodiment the mesodermal precursor cell is produced by culturing an iPSC in the MDM or MDM1 medium described herein for 7 passages, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 7 passages, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 7 passages, in the presence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 7 passages, in the presence of a basement membrane matrix, in the presence of feeder cells, such that the differentiated mesodermal precursor cells express CD31 and CD34, but not CD45. In one embodiment the mesodermal precursor cell is produced by culturing an iPSC in the MDM or MDM1 medium described herein for 7 passages, in the absence of a basement membrane matrix, in the absence of feeder cells, such that the differentiated mesodermal precursor cells express CD31 and CD34, but not CD45. In one embodiment the mesodermal precursor cell is produced by culturing an iPSC in the MDM or MDM1 medium described herein for 7 passages, in the absence of a basement membrane matrix, in the presence of feeder cells, such that the differentiated mesodermal precursor cells express CD31 and CD34, but not CD45.

Figure 2:
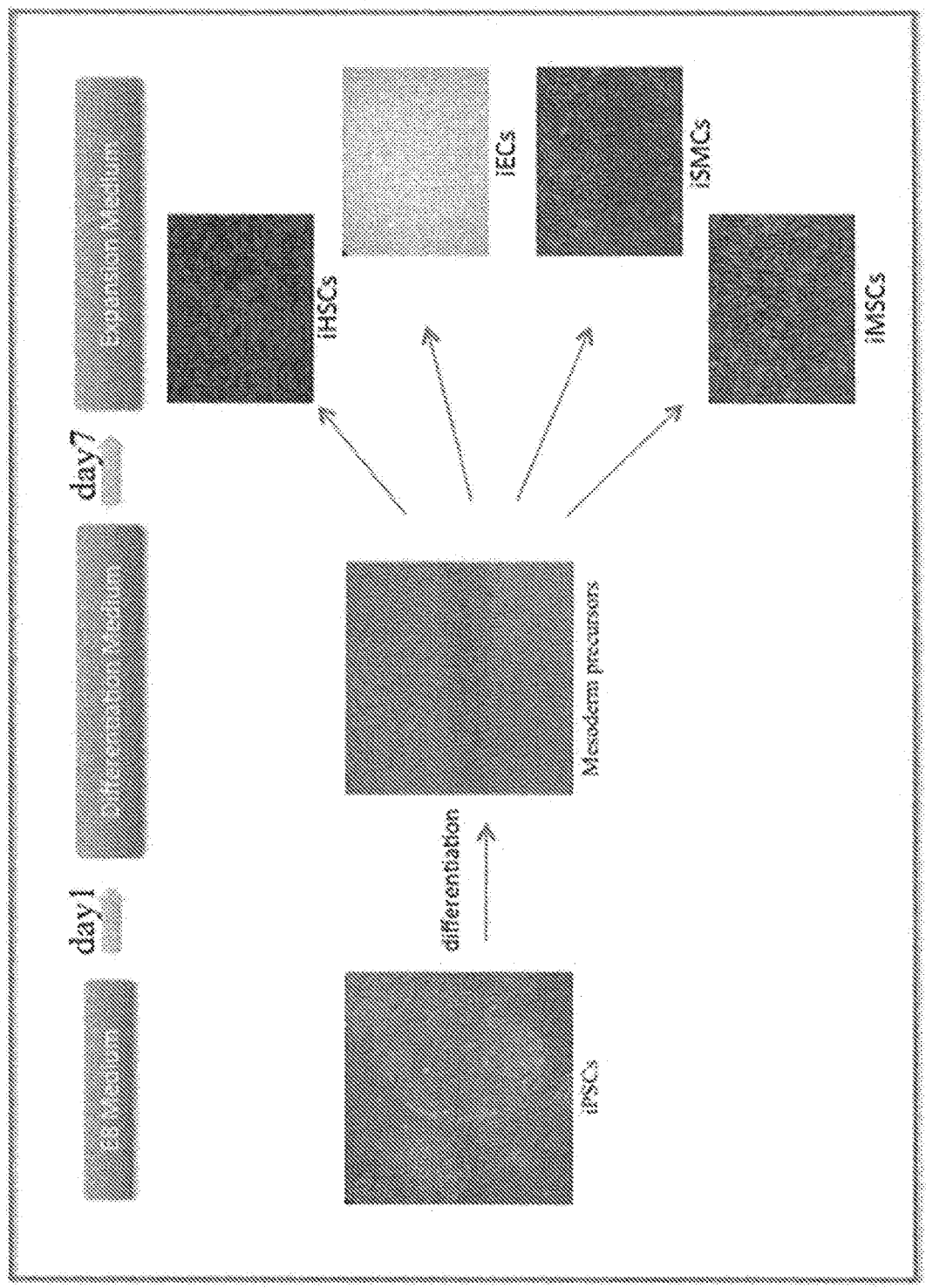
FIG. 2. Depiction of a step-wise protocol to drive hiPSCs into mesoderm precursor cells using feeder-free and chemically defined cell culture media, following by specifically lineage commitment and maturation.
Figure 3A:
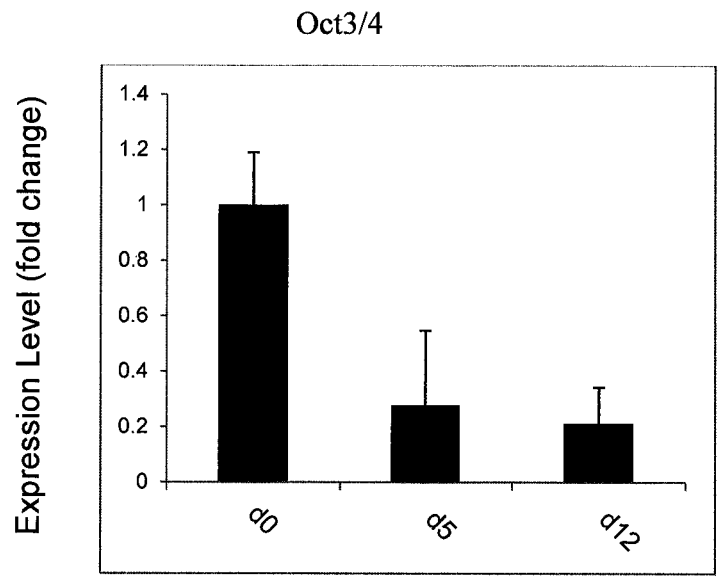
FIGS. 3A-3F. Analysis of gene expression level in cells of undifferentiated and differentiated cells by RT-PCR.
Figure 3B:
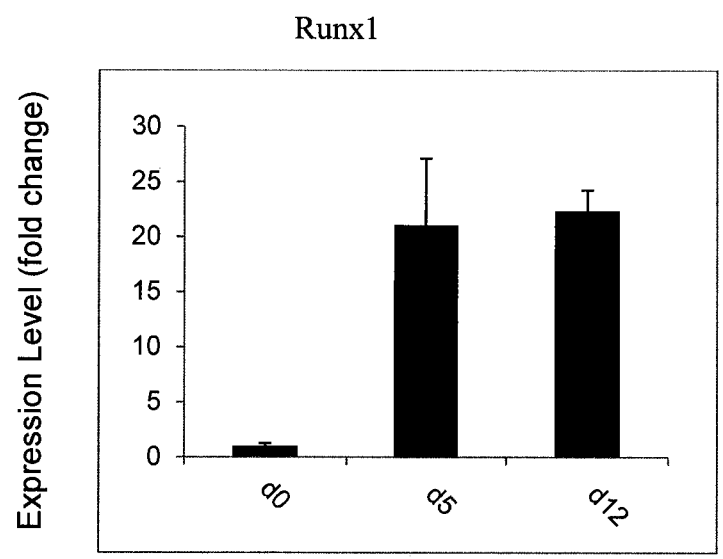
Figure 3C:
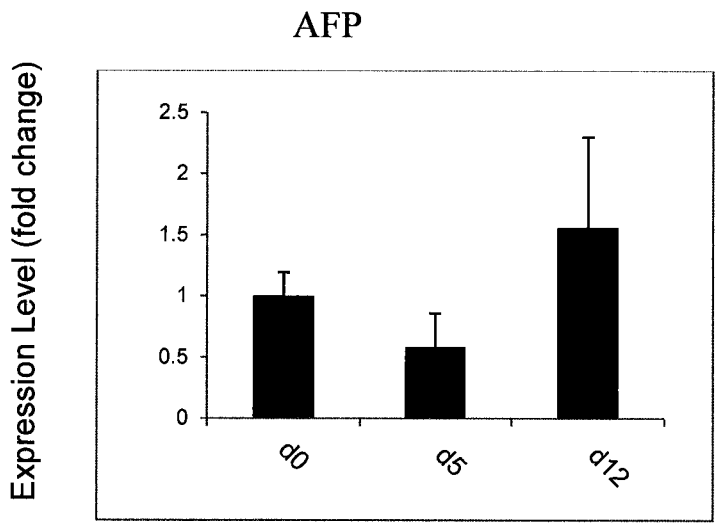
Figure 3D:
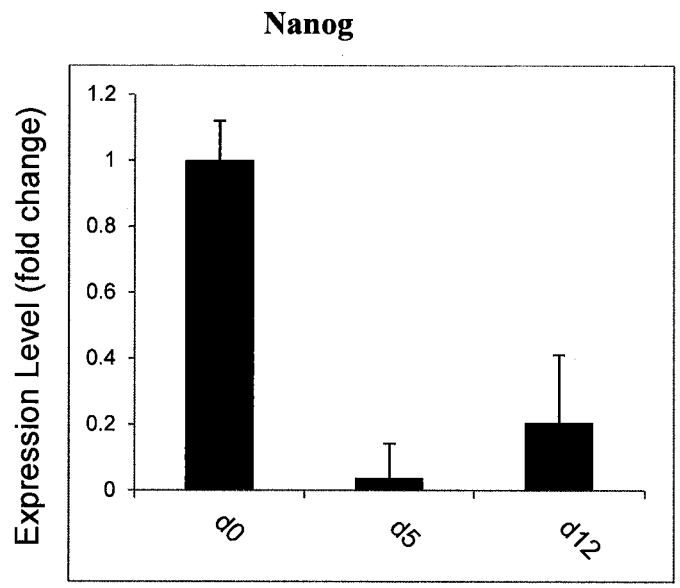
Figure 3E:
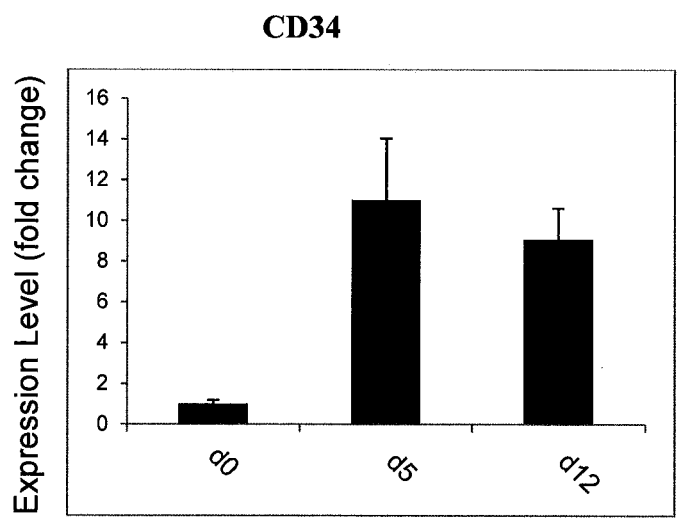
Figure 3F:
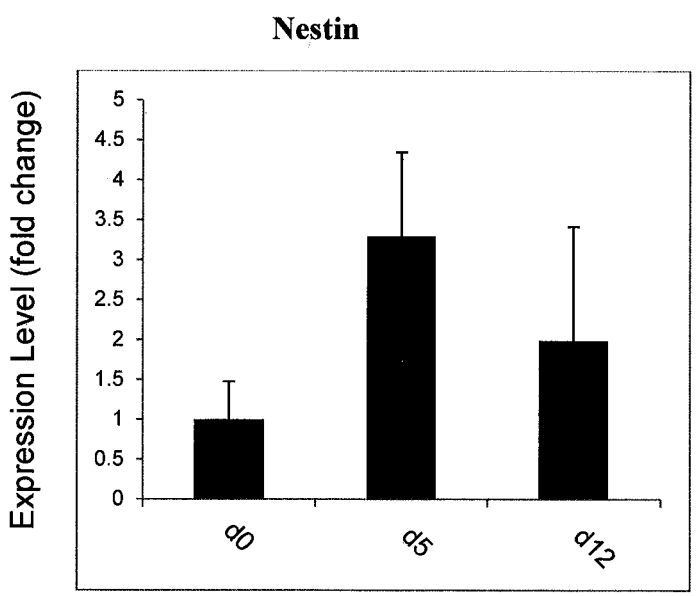
Figures 4A, 4B, 4C:
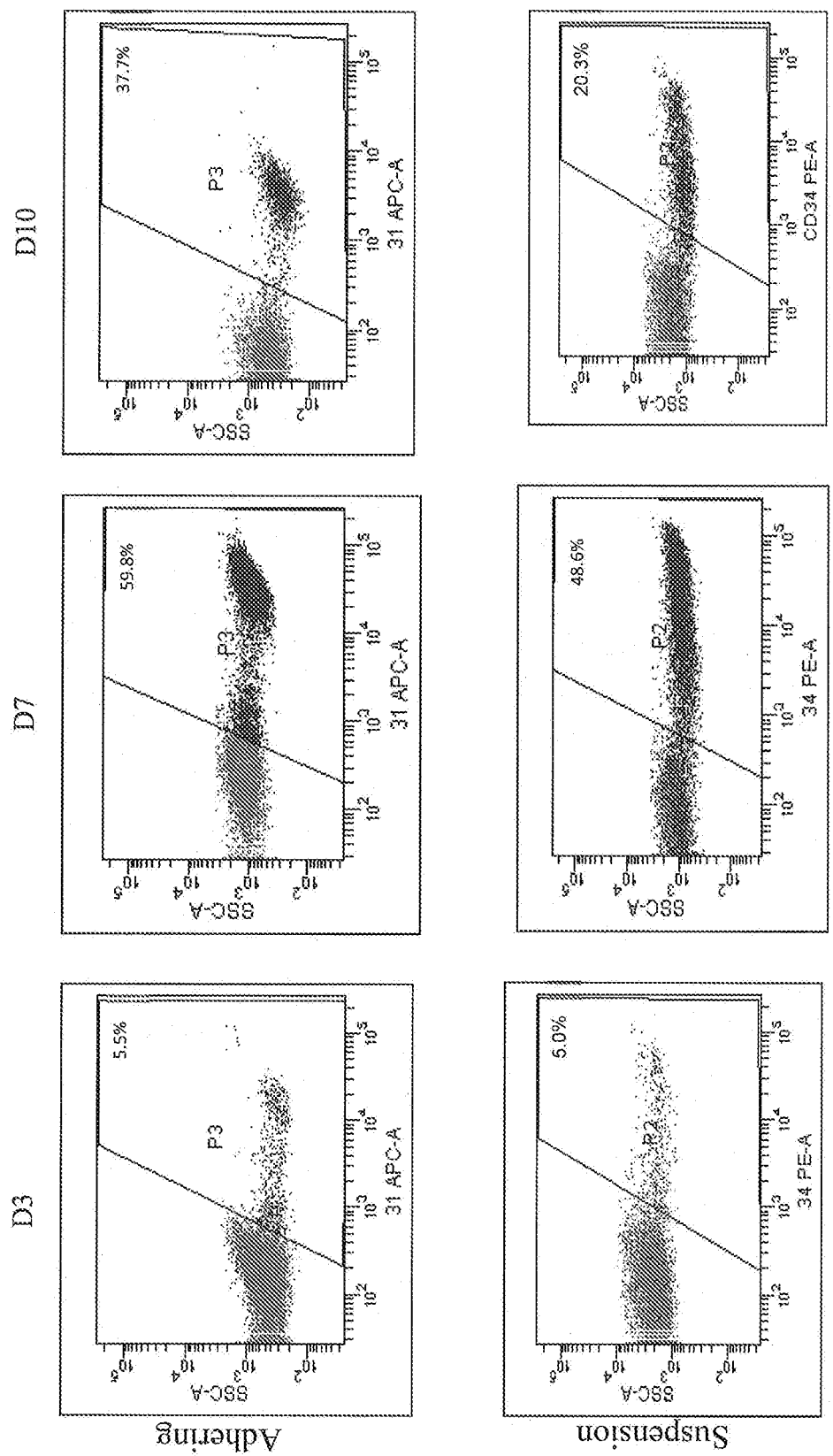
FIGS. 4A-4E. Kinetic analysis of mesoderm precursor cells from pluripotent stem cells by FACS, using CD31 and CD34 as markers.
Figure 4D:
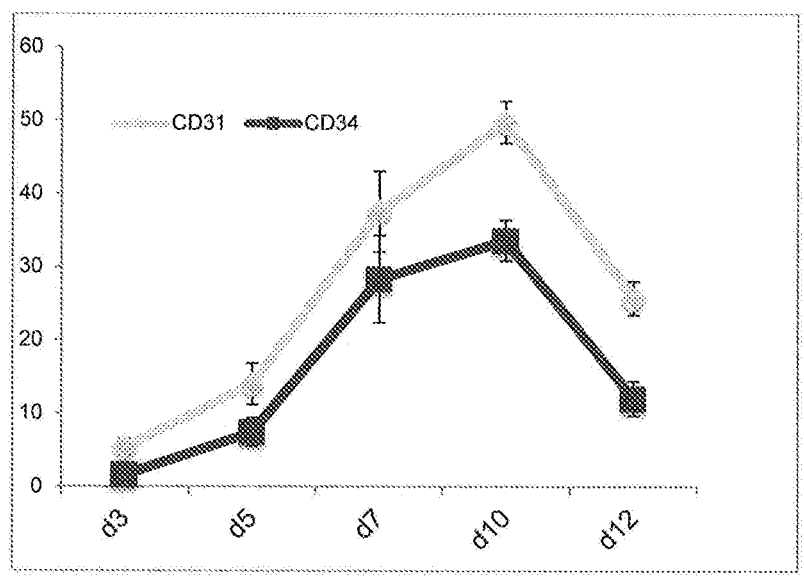
Figure 4E:
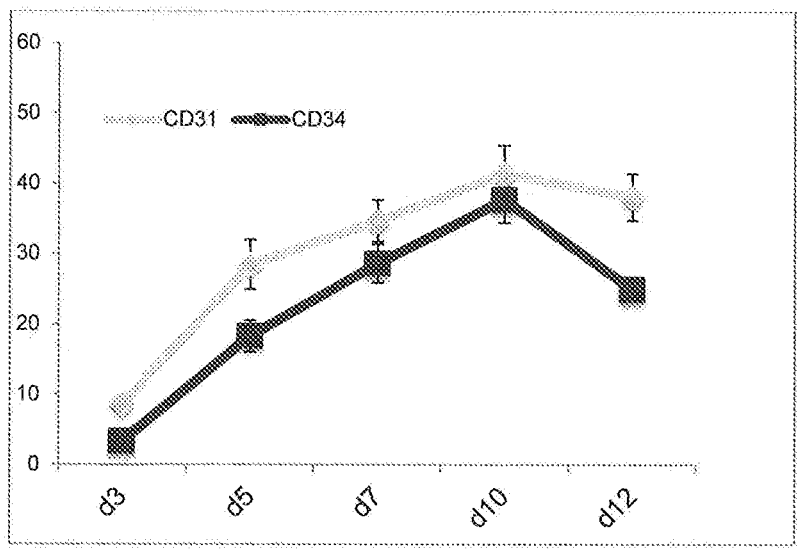

Once produced from iPSCs, the mesodermal precursor cells may be cultured to differentiate into one of at least four different lineages: hematopoietic stem cells (HSC), mesenchymal stem cells (MSC), smooth muscle cells (SMC), or unlimited functional endothelial cells (UFEC) (FIG. 2). All of these cell types are "induced" cell types because they are not produced naturally by the processes described herein; therefore, these cells may also be referred to as induced hematopoietic stem cells (iHSC), induced mesenchymal stem cells (iMSC), induced smooth muscle cells (iSMC), or induced unlimited functional endothelial cells (iUFEC). Despite the possible nomenclature variation, the cells, as discussed herein are the same.

Hematopoietic Stem Cells (HSC)

Provided herein is a method for producing a hematopoietic stem cell from a mesodermal precursor cell, where the method involves first producing a mesodermal precursor cell from an iPSC and then incubating the mesodermal precursor cell in the MDM+ or MDM1+ medium described herein. In some embodiments, the mesodermal precursor cells can be incubated in MDM or MDM1 medium to allow for the production of hematopoietic stem cells. The produced hematopoietic stem cells can be characterized as expressing CD31, CD34, and CD45, but not CD38 (CD31$^+$, CD34$^+$, CD45$^+$, CD38$^-$). In some embodiments of the method, the mesodermal precursor cells cultured to give rise to the hematopoietic stem cells are purified, for example by flow cytometry, prior to being further cultured to differentiate into hematopoietic stem cells. Alternatively, in some embodiments of the method, the mesodermal precursor cells cultured to give rise to the hematopoietic stem cells are not purified from other cells in the initial iPSC culture prior to being further cultured to differentiate into hematopoietic stem cells.

In one embodiment the hematopoietic stem cell is produced by culturing a mesodermal precursor cell in the MDM+ or MDM1+ medium described herein for a period of at least 3 days, in the absence of feeder cells. In one embodiment the hematopoietic stem cell is produced by culturing a mesodermal precursor cell in the MDM+ or MDM+ medium described herein for a period of at least 3 days, in the presence of feeder cells. In one embodiment the hematopoietic stem cell is produced by culturing a mesodermal precursor cell in the MDM+ or MDM1+ medium described herein for a period of at least 3 days, in the presence of a basement membrane matrix, in the absence of feeder cells. In one embodiment the hematopoietic stem cell is produced by culturing a mesodermal precursor cell in the MDM+ or MDM1+ medium described herein for a period of at least 3 days, in the presence of a basement membrane matrix, in the presence of feeder cells. In one embodiment the hematopoietic stem cell is produced by culturing a mesodermal precursor cell in the MDM+ or MDM1+ medium described herein for a period of at least 3 days, in the absence of a basement membrane matrix, in the absence of feeder cells. In one embodiment the hematopoietic stem cell is produced by culturing a mesodermal precursor cell in the MDM+ or MDM1+ medium described herein for a period of at least 3 days, in the absence of a basement membrane matrix, in the presence of feeder cells.

In one embodiment the hematopoietic stem cell is produced by culturing a mesodermal precursor cell in the MDM+ or MDM1+ medium described herein for a period of at least 4 days, in the absence of feeder cells. In one embodiment the hematopoietic stem cell is produced by culturing a mesodermal precursor cell in the MDM+ or MDM1+ medium described herein for a period of at least 4 days, in the presence of feeder cells. In one embodiment the hematopoietic stem cell is produced by culturing a mesodermal precursor cell in the MDM+ or MDM1+ medium described herein for a period of at least 4 days, in the presence of a basement membrane matrix, in the absence of feeder cells. In one embodiment the hematopoietic stem cell is produced by culturing a mesodermal precursor cell in the MDM+ or MDM1+ medium described herein for a period of at least 4 days, in the presence of a basement membrane matrix, in the presence of feeder cells. In one embodiment the hematopoietic stem cell is produced by culturing a mesodermal precursor cell in the MDM+ or MDM1+ medium described herein for a period of at least 4 days, in the absence of a basement membrane matrix, in the absence of feeder cells. In one embodiment the hematopoietic stem cell is produced by culturing a mesodermal precursor cell in the MDM+ or MDM1+ medium described herein for a period of at least 4 days, in the absence of a basement membrane matrix, in the presence of feeder cells.

In one embodiment the hematopoietic stem cell is produced by culturing a mesodermal precursor cell in the MDM+ or MDM1+ medium described herein for a period of at least 5 days, in the absence of feeder cells. In one embodiment the hematopoietic stem cell is produced by culturing a mesodermal precursor cell in the MDM+ or MDM1+ medium described herein for a period of at least 5 days, in the presence of feeder cells. In one embodiment the hematopoietic stem cell is produced by culturing a mesodermal precursor cell in the MDM+ or MDM1+ medium described herein for a period of at least 5 days, in the presence of a basement membrane matrix, in the absence of feeder cells. In one embodiment the hematopoietic stem cell is produced by culturing a mesodermal precursor cell in the MDM+ or MDM1+ medium described herein for a period of at least 5 days, in the presence of a basement membrane matrix, in the presence of feeder cells. In one embodiment the hematopoietic stem cell is produced by culturing a mesodermal precursor cell in the MDM+ or MDM1+ medium described herein for a period of at least 5 days, in the absence of a basement membrane matrix, in the absence of feeder cells. In one embodiment the hematopoietic stem cell is produced by culturing a mesodermal precursor cell in the MDM+ or MDM1+ medium described herein for a period of at least 5 days, in the absence of a basement membrane matrix, in the presence of feeder cells.

In one embodiment the hematopoietic stem cell is produced by culturing a mesodermal precursor cell in the MDM+ or MDM1+ medium described herein for a period of at least 6 days, in the absence of feeder cells. In one embodiment the hematopoietic stem cell is produced by culturing a mesodermal precursor cell in the MDM+ or MDM1+ medium described herein for a period of at least 6 days, in the presence of feeder cells. In one embodiment the hematopoietic stem cell is produced by culturing a mesodermal precursor cell in the MDM+ or MDM1+ medium described herein for a period of at least 6 days, in the presence of a basement membrane matrix, in the absence of feeder cells. In one embodiment the hematopoietic stem cell is produced by culturing a mesodermal precursor cell in the MDM+ or MDM1+ medium described herein for a period of at least 6 days, in the presence of a basement membrane matrix, in the presence of feeder cells. In one embodiment the hematopoietic stem cell is produced by culturing a mesodermal precursor cell in the MDM+ or MDM1+ medium described herein for a period of at least 6 days, in the absence of a basement membrane matrix, in the absence of feeder cells. In one embodiment the hematopoietic stem cell is produced by culturing a mesodermal precursor cell in the MDM+ or MDM1+ medium described herein for a period of at least 6 days, in the absence of a basement membrane matrix, in the presence of feeder cells.

In one embodiment the hematopoietic stem cell is produced by culturing a mesodermal precursor cell in the MDM+ or MDM1+ medium described herein for a period of at least 7 days, in the absence of feeder cells. In one embodiment the hematopoietic stem cell is produced by culturing a mesodermal precursor cell in the MDM+ or MDM1+ medium described herein for a period of at least 7 days, in the presence of feeder cells. In one embodiment the hematopoietic stem cell is produced by culturing a mesodermal precursor cell in the MDM+ or MDM1+ medium described herein for a period of at least 7 days, in the presence of a basement membrane matrix, in the absence of feeder cells. In one embodiment the hematopoietic stem cell is produced by culturing a mesodermal precursor cell in the MDM+ or MDM1+ medium described herein for a period of at least 7 days, in the presence of a basement membrane matrix, in the presence of feeder cells. In one embodiment the hematopoietic stem cell is produced by culturing a mesodermal precursor cell in the MDM+ or MDM1+ medium described herein for a period of at least 7 days, in the absence of a basement membrane matrix, in the absence of feeder cells. In one embodiment the hematopoietic stem cell is produced by culturing a mesodermal precursor cell in the MDM+ or MDM1+ medium described herein for a period of at least 7 days, in the absence of a basement membrane matrix, in the presence of feeder cells.

In one embodiment the hematopoietic stem cell is produced by culturing a mesodermal precursor cell in the MDM+ or MDM1+ medium described herein for a period of at least 8 days, in the absence of feeder cells. In one embodiment the hematopoietic stem cell is produced by culturing a mesodermal precursor cell in the MDM+ or MDM1+ medium described herein for a period of at least 8 days, in the presence of feeder cells. In one embodiment the hematopoietic stem cell is produced by culturing a mesodermal precursor cell in the MDM+ or MDM1+ medium described herein for a period of at least 8 days, in the presence of a basement membrane matrix, in the absence of feeder cells. In one embodiment the hematopoietic stem cell is produced by culturing a mesodermal precursor cell in the MDM+ or MDM1+ medium described herein for a period of at least 8 days, in the presence of a basement membrane matrix, in the presence of feeder cells. In one embodiment the hematopoietic stem cell is produced by culturing a mesodermal precursor cell in the MDM+ or MDM1+ medium described herein for a period of at least 8 days, in the absence of a basement membrane matrix, in the absence of feeder cells. In one embodiment the hematopoietic stem cell is produced by culturing a mesodermal precursor cell in the MDM+ or MDM1+ medium described herein for a period of at least 8 days, in the absence of a basement membrane matrix, in the presence of feeder cells.

In one embodiment the hematopoietic stem cell is produced by culturing a mesodermal precursor cell in the MDM+ or MDM1+ medium described herein for a period of at least 9 days, in the absence of feeder cells. In one embodiment the hematopoietic stem cell is produced by culturing a mesodermal precursor cell in the MDM+ or MDM1+ medium described herein for a period of at least 9 days, in the presence of feeder cells. In one embodiment the hematopoietic stem cell is produced by culturing a mesodermal precursor cell in the MDM+ or MDM1+ medium described herein for a period of at least 9 days, in the presence of a basement membrane matrix, in the absence of feeder cells. In one embodiment the hematopoietic stem cell is produced by culturing a mesodermal precursor cell in the MDM+ or MDM1+ medium described herein for a period of at least 9 days, in the presence of a basement membrane matrix, in the presence of feeder cells. In one embodiment the hematopoietic stem cell is produced by culturing a mesodermal precursor cell in the MDM+ or MDM1+ medium described herein for a period of at least 9 days, in the absence of a basement membrane matrix, in the absence of feeder cells. In one embodiment the hematopoietic stem cell is produced by culturing a mesodermal precursor cell in the MDM+ or MDM1+ medium described herein for a period of at least 9 days, in the absence of a basement membrane matrix, in the presence of feeder cells.

In one embodiment the hematopoietic stem cell is produced by culturing a mesodermal precursor cell in the MDM+ or MDM1+ medium described herein for a period of at least 10 days, in the absence of feeder cells. In one embodiment the hematopoietic stem cell is produced by culturing a mesodermal precursor cell in the MDM+ or MDM1+ medium described herein for a period of at least 10 days, in the presence of feeder cells. In one embodiment the hematopoietic stem cell is produced by culturing a mesodermal precursor cell in the MDM+ or MDM1+ medium described herein for a period of at least 10 days, in the presence of a basement membrane matrix, in the absence of feeder cells. In one embodiment the hematopoietic stem cell is produced by culturing a mesodermal precursor cell in the MDM+ or MDM1+ medium described herein for a period of at least 10 days, in the presence of a basement membrane matrix, in the presence of feeder cells. In one embodiment the hematopoietic stem cell is produced by culturing a mesodermal precursor cell in the MDM+ or MDM1+ medium described herein for a period of at least 10 days, in the absence of a basement membrane matrix, in the absence of feeder cells. In one embodiment the hematopoietic stem cell is produced by culturing a mesodermal precursor cell in the MDM+ or MDM1+ medium described herein for a period of at least 10 days, in the absence of a basement membrane matrix, in the presence of feeder cells.

In one embodiment the hematopoietic stem cell is produced by culturing a mesodermal precursor cell in the MDM+ or MDM1+ medium described herein for a period of at least 3 days, in the absence of feeder cells, such that the differentiated hematopoietic stem cell expresses CD31, CD34, and CD45, but not CD38, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 3 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 3 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 3 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 3 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 3 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of at least 4 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 4 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 4 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 4 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 4 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 4 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of at least 5 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 5 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 5 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 5 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 5 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 5 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of at least 6 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 6 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 6 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 6 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 6 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 6 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of at least 7 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 7 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 7 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 7 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 7 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 7 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of at least 8 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 8 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 8 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 8 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 8 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 8 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of at least 9 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 9 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 9 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 9 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 9 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 9 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of at least 10 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 10 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 10 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 10 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 10 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of at least 10 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of at least 3 days, in the absence of feeder cells. In one embodiment the hematopoietic stem cell is produced by culturing a mesodermal precursor cell in the MDM medium described herein for a period of at least 3 days, in the presence of feeder cells. In one embodiment the hematopoietic stem cell is produced by culturing a mesodermal precursor cell in the MDM medium described herein for a period of at least 3 days, in the presence of a basement membrane matrix, in the absence of feeder cells. In one embodiment the hematopoietic stem cell is produced by culturing a mesodermal precursor cell in the MDM medium described herein for a period of at least 3 days, in the presence of a basement membrane matrix, in the presence of feeder cells. In one embodiment the hematopoietic stem cell is produced by culturing a mesodermal precursor cell in the MDM medium described herein for a period of at least 3 days, in the absence of a basement membrane matrix, in the absence of feeder cells. In one embodiment the hematopoietic stem cell is produced by culturing a mesodermal precursor cell in the MDM medium described herein for a period of at least 3 days, in the absence of a basement membrane matrix, in the presence of feeder cells.

In one embodiment the hematopoietic stem cell is produced by culturing a mesodermal precursor cell in the MDM medium described herein for a period of at least 4 days, in the absence of feeder cells. In one embodiment the hematopoietic stem cell is produced by culturing a mesodermal precursor cell in the MDM medium described herein for a period of at least 4 days, in the presence of feeder cells. In one embodiment the hematopoietic stem cell is produced by culturing a mesodermal precursor cell in the MDM medium described herein for a period of at least 4 days, in the presence of a basement membrane matrix, in the absence of feeder cells. In one embodiment the hematopoietic stem cell is produced by culturing a mesodermal precursor cell in the MDM medium described herein for a period of at least 4 days, in the presence of a basement membrane matrix, in the presence of feeder cells. In one embodiment the hematopoietic stem cell is produced by culturing a mesodermal precursor cell in the MDM medium described herein for a period of at least 4 days, in the absence of a basement membrane matrix, in the absence of feeder cells. In one embodiment the hematopoietic stem cell is produced by culturing a mesodermal precursor cell in the MDM medium described herein for a period of at least 4 days, in the absence of a basement membrane matrix, in the presence of feeder cells.

In one embodiment the hematopoietic stem cell is produced by culturing a mesodermal precursor cell in the MDM medium described herein for a period of at least 5 days, in the absence of feeder cells. In one embodiment the hematopoietic stem cell is produced by culturing a mesodermal precursor cell in the MDM medium described herein for a period of at least 5 days, in the presence of feeder cells. In one embodiment the hematopoietic stem cell is produced by culturing a mesodermal precursor cell in the MDM medium described herein for a period of at least 5 days, in the presence of a basement membrane matrix, in the absence of feeder cells. In one embodiment the hematopoietic stem cell is produced by culturing a mesodermal precursor cell in the MDM medium described herein for a period of at least 5 days, in the presence of a basement membrane matrix, in the presence of feeder cells. In one embodiment the hematopoietic stem cell is produced by culturing a mesodermal precursor cell in the MDM medium described herein for a period of at least 5 days, in the absence of a basement membrane matrix, in the absence of feeder cells. In one embodiment the hematopoietic stem cell is produced by culturing a mesodermal precursor cell in the MDM medium described herein for a period of at least 5 days, in the absence of a basement membrane matrix, in the presence of feeder cells.

In one embodiment the hematopoietic stem cell is produced by culturing a mesodermal precursor cell in the MDM medium described herein for a period of at least 6 days, in the absence of feeder cells. In one embodiment the hematopoietic stem cell is produced by culturing a mesodermal precursor cell in the MDM medium described herein for a period of at least 6 days, in the presence of feeder cells. In one embodiment the hematopoietic stem cell is produced by culturing a mesodermal precursor cell in the MDM medium described herein for a period of at least 6 days, in the presence of a basement membrane matrix, in the absence of feeder cells. In one embodiment the hematopoietic stem cell is produced by culturing a mesodermal precursor cell in the MDM medium described herein for a period of at least 6 days, in the presence of a basement membrane matrix, in the presence of feeder cells. In one embodiment the hematopoietic stem cell is produced by culturing a mesodermal precursor cell in the MDM medium described herein for a period of at least 6 days, in the absence of a basement membrane matrix, in the absence of feeder cells. In one embodiment the hematopoietic stem cell is produced by culturing a mesodermal precursor cell in the MDM medium described herein for a period of at least 6 days, in the absence of a basement membrane matrix, in the presence of feeder cells.

In one embodiment the hematopoietic stem cell is produced by culturing a mesodermal precursor cell in the MDM medium described herein for a period of at least 7 days, in the absence of feeder cells. In one embodiment the hematopoietic stem cell is produced by culturing a mesodermal precursor cell in the MDM medium described herein for a period of at least 7 days, in the presence of feeder cells. In one embodiment the hematopoietic stem cell is produced by culturing a mesodermal precursor cell in the MDM medium described herein for a period of at least 7 days, in the presence of a basement membrane matrix, in the absence of feeder cells. In one embodiment the hematopoietic stem cell is produced by culturing a mesodermal precursor cell in the MDM medium described herein for a period of at least 7 days, in the presence of a basement membrane matrix, in the presence of feeder cells. In one embodiment the hematopoietic stem cell is produced by culturing a mesodermal precursor cell in the MDM medium described herein for a period of at least 7 days, in the absence of a basement membrane matrix, in the absence of feeder cells. In one embodiment the hematopoietic stem cell is produced by culturing a mesodermal precursor cell in the MDM medium described herein for a period of at least 7 days, in the absence of a basement membrane matrix, in the presence of feeder cells.

In one embodiment the hematopoietic stem cell is produced by culturing a mesodermal precursor cell in the MDM medium described herein for a period of at least 8 days, in the absence of feeder cells. In one embodiment the hematopoietic stem cell is produced by culturing a mesodermal precursor cell in the MDM medium described herein for a period of at least 8 days, in the presence of feeder cells. In one embodiment the hematopoietic stem cell is produced by culturing a mesodermal precursor cell in the MDM medium described herein for a period of at least 8 days, in the presence of a basement membrane matrix, in the absence of feeder cells. In one embodiment the hematopoietic stem cell is produced by culturing a mesodermal precursor cell in the MDM medium described herein for a period of at least 8 days, in the presence of a basement membrane matrix, in the presence of feeder cells. In one embodiment the hematopoietic stem cell is produced by culturing a mesodermal precursor cell in the MDM medium described herein for a period of at least 8 days, in the absence of a basement membrane matrix, in the absence of feeder cells. In one embodiment the hematopoietic stem cell is produced by culturing a mesodermal precursor cell in the MDM medium described herein for a period of at least 8 days, in the absence of a basement membrane matrix, in the presence of feeder cells.

In one embodiment the hematopoietic stem cell is produced by culturing a mesodermal precursor cell in the MDM medium described herein for a period of at least 9 days, in the absence of feeder cells. In one embodiment the hematopoietic stem cell is produced by culturing a mesodermal precursor cell in the MDM medium described herein for a period of at least 9 days, in the presence of feeder cells. In one embodiment the hematopoietic stem cell is produced by culturing a mesodermal precursor cell in the MDM medium described herein for a period of at least 9 days, in the presence of a basement membrane matrix, in the absence of feeder cells. In one embodiment the hematopoietic stem cell is produced by culturing a mesodermal precursor cell in the MDM medium described herein for a period of at least 9 days, in the presence of a basement membrane matrix, in the presence of feeder cells. In one embodiment the hematopoietic stem cell is produced by culturing a mesodermal precursor cell in the MDM medium described herein for a period of at least 9 days, in the absence of a basement membrane matrix, in the absence of feeder cells. In one embodiment the hematopoietic stem cell is produced by culturing a mesodermal precursor cell in the MDM medium described herein for a period of at least 9 days, in the absence of a basement membrane matrix, in the presence of feeder cells.

In one embodiment the hematopoietic stem cell is produced by culturing a mesodermal precursor cell in the MDM medium described herein for a period of at least 10 days, in the absence of feeder cells. In one embodiment the hematopoietic stem cell is produced by culturing a mesodermal precursor cell in the MDM medium described herein for a period of at least 10 days, in the presence of feeder cells. In one embodiment the hematopoietic stem cell is produced by culturing a mesodermal precursor cell in the MDM medium described herein for a period of at least 10 days, in the presence of a basement membrane matrix, in the absence of feeder cells. In one embodiment the hematopoietic stem cell is produced by culturing a mesodermal precursor cell in the MDM medium described herein for a period of at least 10 days, in the presence of a basement membrane matrix, in the presence of feeder cells. In one embodiment the hematopoietic stem cell is produced by culturing a mesodermal precursor cell in the MDM medium described herein for a period of at least 10 days, in the absence of a basement membrane matrix, in the absence of feeder cells. In one embodiment the hematopoietic stem cell is produced by culturing a mesodermal precursor cell in the MDM medium described herein for a period of at least 10 days, in the absence of a basement membrane matrix, in the presence of feeder cells.

In one embodiment the hematopoietic stem cell is produced by culturing a mesodermal precursor cell in the MDM medium described herein for a period of at least 3 days, in the absence of feeder cells, such that the differentiated hematopoietic stem cell expresses CD31, CD34, and CD45, but not CD38, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 3 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 3 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 3 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 3 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 3 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of at least 4 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 4 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 4 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 4 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 4 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 4 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of at least 5 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 5 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 5 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 5 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 5 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 5 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of at least 6 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 6 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 6 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 6 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 6 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 6 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of at least 7 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 7 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 7 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 7 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 7 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 7 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of at least 8 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 8 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 8 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 8 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 8 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 8 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of at least 9 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 9 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 9 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 9 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 9 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 9 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of at least 10 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 10 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 10 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 10 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 10 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of at least 10 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of 3 days, in the absence of feeder cells. In one embodiment the hematopoietic stem cell is produced by culturing a mesodermal precursor cell in the MDM+ or MDM1+ medium described herein for a period of 3 days, in the presence of feeder cells. In one embodiment the hematopoietic stem cell is produced by culturing a mesodermal precursor cell in the MDM+ or MDM1+ medium described herein for a period of 3 days, in the presence of a basement membrane matrix, in the absence of feeder cells. In one embodiment the hematopoietic stem cell is produced by culturing a mesodermal precursor cell in the MDM+ or MDM1+ medium described herein for a period of 3 days, in the presence of a basement membrane matrix, in the presence of feeder cells. In one embodiment the hematopoietic stem cell is produced by culturing a mesodermal precursor cell in the MDM+ or MDM1+ medium described herein for a period of 3 days, in the absence of a basement membrane matrix, in the absence of feeder cells. In one embodiment the hematopoietic stem cell is produced by culturing a mesodermal precursor cell in the MDM+ or MDM1+ medium described herein for a period of 3 days, in the absence of a basement membrane matrix, in the presence of feeder cells.

In one embodiment the hematopoietic stem cell is produced by culturing a mesodermal precursor cell in the MDM+ or MDM1+ medium described herein for a period of 4 days, in the absence of feeder cells. In one embodiment the hematopoietic stem cell is produced by culturing a mesodermal precursor cell in the MDM+ or MDM1+ medium described herein for a period of 4 days, in the presence of feeder cells. In one embodiment the hematopoietic stem cell is produced by culturing a mesodermal precursor cell in the MDM+ or MDM1+ medium described herein for a period of 4 days, in the presence of a basement membrane matrix, in the absence of feeder cells. In one embodiment the hematopoietic stem cell is produced by culturing a mesodermal precursor cell in the MDM+ or MDM1+ medium described herein for a period of 4 days, in the presence of a basement membrane matrix, in the presence of feeder cells. In one embodiment the hematopoietic stem cell is produced by culturing a mesodermal precursor cell in the MDM+ or MDM1+ medium described herein for a period of 4 days, in the absence of a basement membrane matrix, in the absence of feeder cells. In one embodiment the hematopoietic stem cell is produced by culturing a mesodermal precursor cell in the MDM+ or MDM1+ medium described herein for a period of 4 days, in the absence of a basement membrane matrix, in the presence of feeder cells.

In one embodiment the hematopoietic stem cell is produced by culturing a mesodermal precursor cell in the MDM+ or MDM1+ medium described herein for a period of 5 days, in the absence of feeder cells. In one embodiment the hematopoietic stem cell is produced by culturing a mesodermal precursor cell in the MDM+ or MDM1+ medium described herein for a period of 5 days, in the presence of feeder cells. In one embodiment the hematopoietic stem cell is produced by culturing a mesodermal precursor cell in the MDM+ or MDM1+ medium described herein for a period of 5 days, in the presence of a basement membrane matrix, in the absence of feeder cells. In one embodiment the hematopoietic stem cell is produced by culturing a mesodermal precursor cell in the MDM+ or MDM1+ medium described herein for a period of 5 days, in the presence of a basement membrane matrix, in the presence of feeder cells. In one embodiment the hematopoietic stem cell is produced by culturing a mesodermal precursor cell in the MDM+ or MDM1+ medium described herein for a period of 5 days, in the absence of a basement membrane matrix, in the absence of feeder cells. In one embodiment the hematopoietic stem cell is produced by culturing a mesodermal precursor cell in the MDM+ or MDM1+ medium described herein for a period of 5 days, in the absence of a basement membrane matrix, in the presence of feeder cells.

In one embodiment the hematopoietic stem cell is produced by culturing a mesodermal precursor cell in the MDM+ or MDM1+ medium described herein for a period of 6 days, in the absence of feeder cells. In one embodiment the hematopoietic stem cell is produced by culturing a mesodermal precursor cell in the MDM+ or MDM1+ medium described herein for a period of 6 days, in the presence of feeder cells. In one embodiment the hematopoietic stem cell is produced by culturing a mesodermal precursor cell in the MDM+ or MDM1+ medium described herein for a period of 6 days, in the presence of a basement membrane matrix, in the absence of feeder cells. In one embodiment the hematopoietic stem cell is produced by culturing a mesodermal precursor cell in the MDM+ or MDM1+ medium described herein for a period of 6 days, in the presence of a basement membrane matrix, in the presence of feeder cells. In one embodiment the hematopoietic stem cell is produced by culturing a mesodermal precursor cell in the MDM+ or MDM1+ medium described herein for a period of 6 days, in the absence of a basement membrane matrix, in the absence of feeder cells. In one embodiment the hematopoietic stem cell is produced by culturing a mesodermal precursor cell in the MDM+ or MDM1+ medium described herein for a period of 6 days, in the absence of a basement membrane matrix, in the presence of feeder cells.

In one embodiment the hematopoietic stem cell is produced by culturing a mesodermal precursor cell in the MDM+ or MDM1+ medium described herein for a period of 7 days, in the absence of feeder cells. In one embodiment the hematopoietic stem cell is produced by culturing a mesodermal precursor cell in the MDM+ or MDM1+ medium described herein for a period of 7 days, in the presence of feeder cells. In one embodiment the hematopoietic stem cell is produced by culturing a mesodermal precursor cell in the MDM+ or MDM1+ medium described herein for a period of 7 days, in the presence of a basement membrane matrix, in the absence of feeder cells. In one embodiment the hematopoietic stem cell is produced by culturing a mesodermal precursor cell in the MDM+ or MDM1+ medium described herein for a period of 7 days, in the presence of a basement membrane matrix, in the presence of feeder cells. In one embodiment the hematopoietic stem cell is produced by culturing a mesodermal precursor cell in the MDM+ or MDM1+ medium described herein for a period of 7 days, in the absence of a basement membrane matrix, in the absence of feeder cells. In one embodiment the hematopoietic stem cell is produced by culturing a mesodermal precursor cell in the MDM+ or MDM1+ medium described herein for a period of 7 days, in the absence of a basement membrane matrix, in the presence of feeder cells.

In one embodiment the hematopoietic stem cell is produced by culturing a mesodermal precursor cell in the MDM+ or MDM1+ medium described herein for a period of 8 days, in the absence of feeder cells. In one embodiment the hematopoietic stem cell is produced by culturing a mesodermal precursor cell in the MDM+ or MDM1+ medium described herein for a period of 8 days, in the presence of feeder cells. In one embodiment the hematopoietic stem cell is produced by culturing a mesodermal precursor cell in the MDM+ or MDM1+ medium described herein for a period of 8 days, in the presence of a basement membrane matrix, in the absence of feeder cells. In one embodiment the hematopoietic stem cell is produced by culturing a mesodermal precursor cell in the MDM+ or MDM1+ medium described herein for a period of 8 days, in the presence of a basement membrane matrix, in the presence of feeder cells. In one embodiment the hematopoietic stem cell is produced by culturing a mesodermal precursor cell in the MDM+ or MDM1+ medium described herein for a period of 8 days, in the absence of a basement membrane matrix, in the absence of feeder cells. In one embodiment the hematopoietic stem cell is produced by culturing a mesodermal precursor cell in the MDM+ or MDM1+ medium described herein for a period of 8 days, in the absence of a basement membrane matrix, in the presence of feeder cells.

In one embodiment the hematopoietic stem cell is produced by culturing a mesodermal precursor cell in the MDM+ or MDM1+ medium described herein for a period of 9 days, in the absence of feeder cells. In one embodiment the hematopoietic stem cell is produced by culturing a mesodermal precursor cell in the MDM+ or MDM1+ medium described herein for a period of 9 days, in the presence of feeder cells. In one embodiment the hematopoietic stem cell is produced by culturing a mesodermal precursor cell in the MDM+ or MDM1+ medium described herein for a period of 9 days, in the presence of a basement membrane matrix, in the absence of feeder cells. In one embodiment the hematopoietic stem cell is produced by culturing a mesodermal precursor cell in the MDM+ or MDM1+ medium described herein for a period of 9 days, in the presence of a basement membrane matrix, in the presence of feeder cells. In one embodiment the hematopoietic stem cell is produced by culturing a mesodermal precursor cell in the MDM+ or MDM1+ medium described herein for a period of 9 days, in the absence of a basement membrane matrix, in the absence of feeder cells. In one embodiment the hematopoietic stem cell is produced by culturing a mesodermal precursor cell in the MDM+ or MDM1+ medium described herein for a period of 9 days, in the absence of a basement membrane matrix, in the presence of feeder cells.

In one embodiment the hematopoietic stem cell is produced by culturing a mesodermal precursor cell in the MDM+ or MDM1+ medium described herein for a period of 10 days, in the absence of feeder cells. In one embodiment the hematopoietic stem cell is produced by culturing a mesodermal precursor cell in the MDM+ or MDM1+ medium described herein for a period of 10 days, in the presence of feeder cells. In one embodiment the hematopoietic stem cell is produced by culturing a mesodermal precursor cell in the MDM+ or MDM1+ medium described herein for a period of 10 days, in the presence of a basement membrane matrix, in the absence of feeder cells. In one embodiment the hematopoietic stem cell is produced by culturing a mesodermal precursor cell in the MDM+ or MDM1+ medium described herein for a period of 10 days, in the presence of a basement membrane matrix, in the presence of feeder cells. In one embodiment the hematopoietic stem cell is produced by culturing a mesodermal precursor cell in the MDM+ or MDM1+ medium described herein for a period of 10 days, in the absence of a basement membrane matrix, in the absence of feeder cells. In one embodiment the hematopoietic stem cell is produced by culturing a mesodermal precursor cell in the MDM+ or MDM1+ medium described herein for a period of 10 days, in the absence of a basement membrane matrix, in the presence of feeder cells.

In one embodiment the hematopoietic stem cell is produced by culturing a mesodermal precursor cell in the MDM+ or MDM1+ medium described herein for a period of 3 days, in the absence of feeder cells, such that the differentiated hematopoietic stem cell expresses CD31, CD34, and CD45, but not CD38, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 3 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 3 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 3 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 3 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 3 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of 4 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 4 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 4 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 4 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 4 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 4 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of 5 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 5 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 5 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 5 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 5 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 5 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of 6 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 6 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 6 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 6 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 6 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 6 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of 7 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 7 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 7 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 7 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 7 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 7 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of 8 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 8 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 8 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 8 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 8 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 8 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of 9 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 9 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 9 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 9 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 9 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 9 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM+ or MDM1+ medium described herein for a period of 10 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 10 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 10 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 10 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 10 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM+ or MDM1+ medium described herein for a period of 10 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of 3 days, in the absence of feeder cells. In one embodiment the hematopoietic stem cell is produced by culturing a mesodermal precursor cell in the MDM medium described herein for a period of 3 days, in the presence of feeder cells. In one embodiment the hematopoietic stem cell is produced by culturing a mesodermal precursor cell in the MDM medium described herein for a period of 3 days, in the presence of a basement membrane matrix, in the absence of feeder cells. In one embodiment the hematopoietic stem cell is produced by culturing a mesodermal precursor cell in the MDM medium described herein for a period of 3 days, in the presence of a basement membrane matrix, in the presence of feeder cells. In one embodiment the hematopoietic stem cell is produced by culturing a mesodermal precursor cell in the MDM medium described herein for a period of 3 days, in the absence of a basement membrane matrix, in the absence of feeder cells. In one embodiment the hematopoietic stem cell is produced by culturing a mesodermal precursor cell in the MDM medium described herein for a period of 3 days, in the absence of a basement membrane matrix, in the presence of feeder cells.

In one embodiment the hematopoietic stem cell is produced by culturing a mesodermal precursor cell in the MDM medium described herein for a period of 4 days, in the absence of feeder cells. In one embodiment the hematopoietic stem cell is produced by culturing a mesodermal precursor cell in the MDM medium described herein for a period of 4 days, in the presence of feeder cells. In one embodiment the hematopoietic stem cell is produced by culturing a mesodermal precursor cell in the MDM medium described herein for a period of 4 days, in the presence of a basement membrane matrix, in the absence of feeder cells. In one embodiment the hematopoietic stem cell is produced by culturing a mesodermal precursor cell in the MDM medium described herein for a period of 4 days, in the presence of a basement membrane matrix, in the presence of feeder cells. In one embodiment the hematopoietic stem cell is produced by culturing a mesodermal precursor cell in the MDM medium described herein for a period of 4 days, in the absence of a basement membrane matrix, in the absence of feeder cells. In one embodiment the hematopoietic stem cell is produced by culturing a mesodermal precursor cell in the MDM medium described herein for a period of 4 days, in the absence of a basement membrane matrix, in the presence of feeder cells.

In one embodiment the hematopoietic stem cell is produced by culturing a mesodermal precursor cell in the MDM medium described herein for a period of 5 days, in the absence of feeder cells. In one embodiment the hematopoietic stem cell is produced by culturing a mesodermal precursor cell in the MDM medium described herein for a period of 5 days, in the presence of feeder cells. In one embodiment the hematopoietic stem cell is produced by culturing a mesodermal precursor cell in the MDM medium described herein for a period of 5 days, in the presence of a basement membrane matrix, in the absence of feeder cells. In one embodiment the hematopoietic stem cell is produced by culturing a mesodermal precursor cell in the MDM medium described herein for a period of 5 days, in the presence of a basement membrane matrix, in the presence of feeder cells. In one embodiment the hematopoietic stem cell is produced by culturing a mesodermal precursor cell in the MDM medium described herein for a period of 5 days, in the absence of a basement membrane matrix, in the absence of feeder cells. In one embodiment the hematopoietic stem cell is produced by culturing a mesodermal precursor cell in the MDM medium described herein for a period of 5 days, in the absence of a basement membrane matrix, in the presence of feeder cells.

In one embodiment the hematopoietic stem cell is produced by culturing a mesodermal precursor cell in the MDM medium described herein for a period of 6 days, in the absence of feeder cells. In one embodiment the hematopoietic stem cell is produced by culturing a mesodermal precursor cell in the MDM medium described herein for a period of 6 days, in the presence of feeder cells. In one embodiment the hematopoietic stem cell is produced by culturing a mesodermal precursor cell in the MDM medium described herein for a period of 6 days, in the presence of a basement membrane matrix, in the absence of feeder cells. In one embodiment the hematopoietic stem cell is produced by culturing a mesodermal precursor cell in the MDM medium described herein for a period of 6 days, in the presence of a basement membrane matrix, in the presence of feeder cells. In one embodiment the hematopoietic stem cell is produced by culturing a mesodermal precursor cell in the MDM medium described herein for a period of 6 days, in the absence of a basement membrane matrix, in the absence of feeder cells. In one embodiment the hematopoietic stem cell is produced by culturing a mesodermal precursor cell in the MDM medium described herein for a period of 6 days, in the absence of a basement membrane matrix, in the presence of feeder cells.

In one embodiment the hematopoietic stem cell is produced by culturing a mesodermal precursor cell in the MDM medium described herein for a period of 7 days, in the absence of feeder cells. In one embodiment the hematopoietic stem cell is produced by culturing a mesodermal precursor cell in the MDM medium described herein for a period of 7 days, in the presence of feeder cells. In one embodiment the hematopoietic stem cell is produced by culturing a mesodermal precursor cell in the MDM medium described herein for a period of 7 days, in the presence of a basement membrane matrix, in the absence of feeder cells. In one embodiment the hematopoietic stem cell is produced by culturing a mesodermal precursor cell in the MDM medium described herein for a period of 7 days, in the presence of a basement membrane matrix, in the presence of feeder cells. In one embodiment the hematopoietic stem cell is produced by culturing a mesodermal precursor cell in the MDM medium described herein for a period of 7 days, in the absence of a basement membrane matrix, in the absence of feeder cells. In one embodiment the hematopoietic stem cell is produced by culturing a mesodermal precursor cell in the MDM medium described herein for a period of 7 days, in the absence of a basement membrane matrix, in the presence of feeder cells.

In one embodiment the hematopoietic stem cell is produced by culturing a mesodermal precursor cell in the MDM medium described herein for a period of 8 days, in the absence of feeder cells. In one embodiment the hematopoietic stem cell is produced by culturing a mesodermal precursor cell in the MDM medium described herein for a period of 8 days, in the presence of feeder cells. In one embodiment the hematopoietic stem cell is produced by culturing a mesodermal precursor cell in the MDM medium described herein for a period of 8 days, in the presence of a basement membrane matrix, in the absence of feeder cells. In one embodiment the hematopoietic stem cell is produced by culturing a mesodermal precursor cell in the MDM medium described herein for a period of 8 days, in the presence of a basement membrane matrix, in the presence of feeder cells. In one embodiment the hematopoietic stem cell is produced by culturing a mesodermal precursor cell in the MDM medium described herein for a period of 8 days, in the absence of a basement membrane matrix, in the absence of feeder cells. In one embodiment the hematopoietic stem cell is produced by culturing a mesodermal precursor cell in the MDM medium described herein for a period of 8 days, in the absence of a basement membrane matrix, in the presence of feeder cells.

In one embodiment the hematopoietic stem cell is produced by culturing a mesodermal precursor cell in the MDM medium described herein for a period of 9 days, in the absence of feeder cells. In one embodiment the hematopoietic stem cell is produced by culturing a mesodermal precursor cell in the MDM medium described herein for a period of 9 days, in the presence of feeder cells. In one embodiment the hematopoietic stem cell is produced by culturing a mesodermal precursor cell in the MDM medium described herein for a period of 9 days, in the presence of a basement membrane matrix, in the absence of feeder cells. In one embodiment the hematopoietic stem cell is produced by culturing a mesodermal precursor cell in the MDM medium described herein for a period of 9 days, in the presence of a basement membrane matrix, in the presence of feeder cells. In one embodiment the hematopoietic stem cell is produced by culturing a mesodermal precursor cell in the MDM medium described herein for a period of 9 days, in the absence of a basement membrane matrix, in the absence of feeder cells. In one embodiment the hematopoietic stem cell is produced by culturing a mesodermal precursor cell in the MDM medium described herein for a period of 9 days, in the absence of a basement membrane matrix, in the presence of feeder cells.

In one embodiment the hematopoietic stem cell is produced by culturing a mesodermal precursor cell in the MDM medium described herein for a period of 10 days, in the absence of feeder cells. In one embodiment the hematopoietic stem cell is produced by culturing a mesodermal precursor cell in the MDM medium described herein for a period of 10 days, in the presence of feeder cells. In one embodiment the hematopoietic stem cell is produced by culturing a mesodermal precursor cell in the MDM medium described herein for a period of 10 days, in the presence of a basement membrane matrix, in the absence of feeder cells. In one embodiment the hematopoietic stem cell is produced by culturing a mesodermal precursor cell in the MDM medium described herein for a period of 10 days, in the presence of a basement membrane matrix, in the presence of feeder cells. In one embodiment the hematopoietic stem cell is produced by culturing a mesodermal precursor cell in the MDM medium described herein for a period of 10 days, in the absence of a basement membrane matrix, in the absence of feeder cells. In one embodiment the hematopoietic stem cell is produced by culturing a mesodermal precursor cell in the MDM medium described herein for a period of 10 days, in the absence of a basement membrane matrix, in the presence of feeder cells.

In one embodiment the hematopoietic stem cell is produced by culturing a mesodermal precursor cell in the MDM medium described herein for a period of 3 days, in the absence of feeder cells, such that the differentiated hematopoietic stem cell expresses CD31, CD34, and CD45, but not CD38, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 3 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 3 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 3 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 3 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 3 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of 4 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 4 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 4 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 4 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 4 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 4 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of 5 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 5 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 5 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 5 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 5 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 5 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of 6 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 6 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 6 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 6 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 6 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 6 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of 7 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 7 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 7 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 7 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 7 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 7 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of 8 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 8 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 8 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 8 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 8 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 8 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of 9 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 9 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 9 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 9 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 9 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 9 days, in the absence of a basement membrane matrix, in the presence of feeder cells, such that the differentiated hematopoietic stem cell expresses CD31, CD34, and CD45, but not CD38.

In one embodiment the hematopoietic stem cell is produced by culturing a mesodermal precursor cell in the MDM medium described herein for a period of 10 days, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 10 days, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 10 days, in the presence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 10 days, in the presence of a basement membrane matrix, in the presence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 10 days, in the absence of a basement membrane matrix, in the absence of feeder cells, such that the differentiated hematopoietic stem cell expresses CD31, CD34, and CD45, but not CD38. In one embodiment the hematopoietic stem cell is produced by culturing a mesodermal precursor cell in the MDM medium described herein for a period of 10 days, in the absence of a basement membrane matrix, in the presence of feeder cells, such that the differentiated hematopoietic stem cell expresses CD31, CD34, and CD45, but not CD38.

Mesenchymal Stem Cells (MSC)

Provided herein is a method for producing a mesenchymal stem cell from the mesodermal precursor cell described herein, wherein the method involves first producing a mesodermal precursor cell from an iPSC, as described by the related methods provided herein, and then incubating the mesodermal precursor cell under conditions known to promote differentiation of precursor cells into mesenchymal stem cells. The produced mesenchymal stem cells can be characterized as expressing CD90, CD73, and CD105, but not CD31 and CD45. In some embodiments of the method, the mesodermal precursor cells cultured to give rise to the mesenchymal stem cells are purified, for example by flow cytometry, prior to being further cultured to differentiate into mesenchymal stem cells. Alternatively, in some embodiments of the method, the mesodermal precursor cells cultured to give rise to the mesenchymal stem cells are not purified from other cells in the initial iPSC culture prior to being further cultured to differentiate into mesenchymal stem cells. The described iMSCs may be further characterized by their multipotency. For example the described iMSCs may further differentiate into adipocytes, osteoblasts, myocytes, or chondrocytes in vitro, when cultured under proper conditions known in the art, or in vivo, for example following transplantation.

Smooth Muscle Cells (SMC)

Provided herein is a method for producing smooth muscle cells from the mesodermal precursor cells described herein, wherein the method involves first producing a mesodermal precursor cell from an iPSC, as described by the related methods provided herein, and then incubating the mesodermal precursor cell under conditions known to promote differentiation of precursor cells into smooth muscle cells. The produced smooth muscle cells can be characterized as expressing α-SMA, calponin, and SM22. Furthermore, the iSMCs exhibit the formation of spindles when grown in culture for an amount of time adequate to allow for cell expansion to levels sufficient to allow for spindle formation. In some embodiments of the method, the mesodermal precursor cells cultured to give rise to the smooth muscle cells are purified, for example by flow cytometry, prior to being further cultured to differentiate into smooth muscle cells. Alternatively, in some embodiments of the method, the mesodermal precursor cells cultured to give rise to the smooth muscle cells are not purified from other cells in the initial iPSC culture prior to being further cultured to differentiate into smooth muscle cells.

Unlimited Functional Endothelial Cells (UFEC)

Provided herein is a method for producing unlimited functional endothelial cells (UFECs) (also referred to as "iECs") from the mesodermal precursor cells described herein, wherein the method involves first producing a mesodermal precursor cell from an iPSC, as described by the related methods provided herein, and then incubating the mesodermal precursor cell under conditions known to promote differentiation of precursor cells into unlimited functional endothelial cells. The produced UFECs can be characterized as expressing CD31, vWF and CD144. Other characteristics of these cells include the ability to form vascular-like structures on Matrigel™ and the uptake of acetylated-LDL when cultured. In some embodiments of the method, the mesodermal precursor cells cultured to give rise to the unlimited functional endothelial cells are purified, for example by flow cytometry, prior to being further cultured to differentiate into unlimited functional endothelial cells. Alternatively, in some embodiments of the method, the mesodermal precursor cells cultured to give rise to the unlimited functional endothelial cells are not purified from other cells in the initial iPSC culture prior to being further cultured to differentiate into unlimited functional endothelial cells.

Cells for Carrying Out the Described Cell Production Methods

The cell production methods described herein may be carried out using a variety of cell types to give rise to the initial iPSCs that serve as the starting point for these methods and cells. For example, it may be desirable to obtain cells from a subject in need of a cell transplant, stem cell therapy, of precursor cell therapy, and use the subject's own autologous cells, such as fibroblasts for example, to generate autologous iPSCs that may be cultured to give rise to an autologous form of one or more of the cell types described herein. In other embodiments, heterologous cells may be used for producing the cells described herein, even though these cells may be intended for therapeutic use in a subject. In still another embodiment, the methods described herein can be carried out using iPSCs without regard to origin. For instance, the iPSCs could be human cells, primate cells, or other mammalian cells converted to iPSCs by conventional methods.

Cells Produced by the Described Methods

Described herein are a variety of cells capable of being produced by the methods described herein. These cells include iPSC-derived mesodermal precursor cells (MPC), positive for CD34 and CD31 expression that may be used to produce at least four different cell types. When cultured under appropriate conditions, the MPCs can be used to produce hematopoietic stem cells, mesenchymal stem cells, smooth muscle cells, or unlimited functional endothelial cells. One characteristic that makes the mesodermal precursor cells described herein desirable is that these cells can be maintained in culture for a number of days, or passages, without changing phenotype through differentiation. In some embodiments the described MPCs can maintain their phenotype in culture for at least 3 days. In some embodiments the described MPCs can maintain their phenotype in culture for at least 5 days. In some embodiments the described MPCs can maintain their phenotype in culture for at least 7 days. In some embodiments the described MPCs can maintain their phenotype in culture for at least 9 days. In some embodiments the described MPCs can maintain their phenotype in culture for at least 10 days. In some embodiments the described MPCs can maintain their phenotype in culture for at least 13 days. In some embodiments the described MPCs can maintain their phenotype in culture for at least 16 days. In some embodiments the described MPCs can maintain their phenotype in culture for at least 20 days. In some embodiments the described MPCs can maintain their phenotype in culture for at least 24 days, or more. In some embodiments the described MPCs will have one or more genes encoding Oct4, Sox2, klf4, or c-MYC incorporated into the genome as a consequence of being produced from an iPSC that was made by overexpression of Oct4, Sox2, klf4, and c-MYC. When the iPSC is produced using a retroviral vector to deliver at least one gene encoding Oct4, Sox2, klf4, or c-MYC, that gene can become integrated into the genome of the iPSC and will subsequently be a part of the genome of the resulting MPC.

Hematopoietic stem cells can be produced by culturing the MPCs described herein. The described HSCs may be characterized by the expression of CD34, CD31, and CD45, but not CD38. Another characteristic of the described HSCs is that they have the ability to reconstitute the hematopoietic system of an irradiated subject, such as a mouse. The described HSCs also have the ability to maintain their phenotype for extended periods without differentiating, when maintained under appropriate conditions, such as being cultured using the MDM medium described herein. In another embodiment the described HSCs can maintain their phenotype for extended periods without differentiating, when cultured using the MDM+ or MDM1+ medium described herein. In some embodiments the described HSCs can maintain their phenotype in culture for at least 3 days. In some embodiments the described HSCs can maintain their phenotype in culture for at least 5 days. In some embodiments the described HSCs can maintain their phenotype in culture for at least 7 days. In some embodiments the described HSCs can maintain their phenotype in culture for at least 9 days. In some embodiments the described HSCs can maintain their phenotype in culture for at least 10 days. In some embodiments the described HSCs can maintain their phenotype in culture for at least 13 days. In some embodiments the described HSCs can maintain their phenotype in culture for at least 16 days. In some embodiments the described HSCs can maintain their phenotype in culture for at least 20 days. In some embodiments the described HSCs can maintain their phenotype in culture for at least 24 days, or more. In some embodiments the described HSCs will have one or more genes encoding Oct4, Sox2, klf4, or c-MYC incorporated into the genome as a consequence of being produced from an iPSC that was made by overexpression of Oct4, Sox2, klf4, and c-MYC. When the iPSC is produced using a retroviral vector to deliver at least one gene encoding Oct4, Sox2, klf4, or c-MYC, that gene can become integrated into the genome of the iPSC and will subsequently be a part of the genome of the resulting HSCs.

Another cell type described herein are unlimited functional endothelial cells that may be obtained by differentiating the described MPCs when cultured under conditions known to allow for differentiation into cells of an endothelial lineage. The described UFECs can be characterized by the expression of CD31, vWF, and CD144. In addition, these cells can mediate the uptake of acetylated low density lipoproteins (LDL). Furthermore, the UFECs produced using the methods and cells described herein have the ability to form vascular-like structures when cultured in vitro, a hallmark of endothelia cell progenitors. One characteristic that makes the UFECs described herein desirable is that these cells can be maintained in culture for a number of days, or passages, without changing phenotype through differentiation. In some embodiments the described UFECs can maintain their phenotype in culture for at least 3 days. In some embodiments the described UFECs can maintain their phenotype in culture for at least 5 days. In some embodiments the described UFECs can maintain their phenotype in culture for at least 7 days. In some embodiments the described UFECs can maintain their phenotype in culture for at least 9 days. In some embodiments the described UFECs can maintain their phenotype in culture for at least 10 days. In some embodiments the described UFECs can maintain their phenotype in culture for at least 13 days. In some embodiments the described UFECs can maintain their phenotype in culture for at least 16 days. In some embodiments the described UFECs can maintain their phenotype in culture for at least 20 days. In some embodiments the described UFECs can maintain their phenotype in culture for at least 24 days, or more. In some embodiments the described UFECs will have one or more genes encoding Oct4, Sox2, klf4, or c-MYC incorporated into the genome as a consequence of being produced from an iPSC that was made by overexpression of Oct4, Sox2, klf4, and c-MYC. When the iPSC is produced using a retroviral vector to deliver at least one gene encoding Oct4, Sox2, klf4, or c-MYC, that gene can become integrated into the genome of the iPSC and will subsequently be a part of the genome of the resulting UFECs, which are indirectly derived from the iPSCs.

Also described herein are mesenchymal stem cells (MSCs) that may be obtained by differentiating the described MPCs under conditions known to allow for differentiation into cells of a mesenchymal lineage. The MSCs described herein can be characterized by the expression of CD90, CD73, and CD105 in the absence of CD31 and CD45. These cells can also differentiate in vivo or in vitro into a number of different cell types, including adipocytes, osteoblasts, myocytes, or chondrocytes, when cultured under conditions known to cause progenitor cells to differentiate into one of these cell types. The described MSCs also have the ability to maintain their phenotype for extended periods without differentiating, when maintained under appropriate conditions, such as conditions known to allow for differentiation into cells of an mesenchymal lineage. In some embodiments the described MSCs can maintain their phenotype in culture for at least 3 days. In some embodiments the described MSCs can maintain their phenotype in culture for at least 5 days. In some embodiments the described MSCs can maintain their phenotype in culture for at least 7 days. In some embodiments the described MSCs can maintain their phenotype in culture for at least 9 days. In some embodiments the described MSCs can maintain their phenotype in culture for at least 10 days. In some embodiments the described MSCs can maintain their phenotype in culture for at least 13 days. In some embodiments the described MSCs can maintain their phenotype in culture for at least 16 days. In some embodiments the described MSCs can maintain their phenotype in culture for at least 20 days. In some embodiments the described MSCs can maintain their phenotype in culture for at least 24 days, or more. In some embodiments the described MSCs will have one or more genes encoding Oct4, Sox2, klf4, or c-MYC incorporated into the genome as a consequence of being produced from an iPSC that was made by overexpression of Oct4, Sox2, klf4, and c-MYC. When the iPSC is produced using a retroviral vector to deliver at least one gene encoding Oct4, Sox2, klf4, or c-MYC, that gene can become integrated into the genome of the iPSC and will subsequently be a part of the genome of the resulting MSCs, which are indirectly derived from the iPSCs.

Smooth muscle cells can be produced by culturing the MPCs described herein. For example, the described MPCs can differentiate into smooth muscle cells when cultured under conditions known to cause progenitor cells to differentiate into SMCs. The described SMCs are characterized by the expression of α-SMA, calponin, and SM22. The described SMCs also have the ability to maintain their phenotype for extended periods without differentiating, when maintained under appropriate conditions, such as conditions known to allow for differentiation into smooth muscle cells. In some embodiments the described SMCs can maintain their phenotype in culture for at least 3 days. In some embodiments the described SMCs can maintain their phenotype in culture for at least 5 days. In some embodiments the described SMCs can maintain their phenotype in culture for at least 7 days. In some embodiments the described SMCs can maintain their phenotype in culture for at least 9 days. In some embodiments the described SMCs can maintain their phenotype in culture for at least 10 days. In some embodiments the described SMCs can maintain their phenotype in culture for at least 13 days. In some embodiments the described SMCs can maintain their phenotype in culture for at least 16 days. In some embodiments the described SMCs can maintain their phenotype in culture for at least 20 days. In some embodiments the described SMCs can maintain their phenotype in culture for at least 24 days, or more. In some embodiments the described SMCs will have one or more genes encoding Oct4, Sox2, klf4, or c-MYC incorporated into the genome as a consequence of being produced from an iPSC that was made by overexpression of Oct4, Sox2, klf4, and c-MYC. When the iPSC is produced using a retroviral vector to deliver at least one gene encoding Oct4, Sox2, klf4, or c-MYC, that gene can become integrated into the genome of the iPSC and will subsequently be a part of the genome of the resulting SMCs, which are indirectly derived from the iPSCs.

The cells described herein may be made using a variety of cell types to give rise to the initial iPSCs that serve as the starting point for producing these cells. For example, it may be desirable to obtain cells from a subject in need of a cell transplant, stem cell therapy, of precursor cell therapy, and use the subject's own autologous cells, such as fibroblasts for example, to generate autologous iPSCs that may be cultured to give rise to an autologous form of one or more of the cell types described herein. In other embodiments, heterologous cells may be used for producing the cells described herein, even though these cells may be intended for therapeutic use in a subject. In still another embodiment, the methods described herein can be carried out using iPSCs without regard to origin. For instance, the iPSCs could be human cells, primate cells, or other mammalian cells converted to PSCs by conventional methods.

Methods of Treatment

Stem cells and lineage precursor cells have been shown to have therapeutic applications to a variety of diseases. Accordingly, the stem cells and progenitor cells described herein, whether autologous or heterologous in nature, may also be used of this purpose. For example, the HSCs described herein may be used to treat a subject with a disorder of the hematopoietic system. In some embodiments the HSCs may be administered to a subject having a congenital bone marrow disorder. Examples of such disorders include congenital aplastic anemia (Fanconi anemia), congenital hypoplastic anemia (Diamond-Blackfan anemia), congenital neutropenias (Kostmann syndrome, cyclic neutropenia, Shwachman-Diamond syndrome and others), and congenital thrombocytopenias (TAR syndrome, amegacaryocytic thrombocytopenia). The described HCSs may be administered to an individual to treat any one of these disorders. In some embodiments the described HSCs may be administered to a subject to treat congenital aplastic anemia (Fanconi anemia). In some embodiments the described HSCs may be administered to a subject to treat congenital hypoplastic anemia (Diamond-Blackfan anemia). In some embodiments the described HSCs may be administered to a subject to treat Kostmann syndrome. In some embodiments the described HSCs may be administered to a subject to treat cyclic neutropenia. In some embodiments the described HSCs may be administered to a subject to treat Shwachman-Diamond syndrome. In some embodiments the described HSCs may be administered to a subject to treat TAR syndrome. In some embodiments the described HSCs may be administered to a subject to treat amegacaryocytic thrombocytopenia. In some embodiments the described HSCs administered to a subject to treat ongenital aplastic anemia (Fanconi anemia) are autologous. In some embodiments the described HSCs administered to a subject to treat congenital hypoplastic anemia (Diamond-Blackfan anemia) are autologous. In some embodiments the described HSCs administered to a subject to treat Kostmann syndrome are autologous. In some embodiments the described HSCs administered to a subject to treat cyclic neutropenia are autologous. In some embodiments the described HSCs administered to a subject to treat Shwachman-Diamond syndrome are autologous. In some embodiments the described HSCs administered to a subject to treat TAR syndrome are autologous. In some embodiments the described HSCs administered to a subject to treat amegacaryocytic thrombocytopenia are autologous. In some embodiments the described HSCs administered to a subject to treat congenital aplastic anemia (Fanconi anemia) are heterologous. In some embodiments the described HSCs administered to a subject to treat congenital hypoplastic anemia (Diamond-Blackfan anemia) are heterologous. In some embodiments the described HSCs administered to a subject to treat Kostmann syndrome are heterologous. In some embodiments the described HSCs administered to a subject to treat cyclic neutropenia are heterologous. In some embodiments the described HSCs administered to a subject to treat Shwachman-Diamond syndrome are heterologous. In some embodiments the described HSCs administered to a subject to treat TAR syndrome are heterologous. In some embodiments the described HSCs administered to a subject to treat amegacaryocytic thrombocytopenia are heterologous. Those skilled in the art will understand that the forgoing disclosure provides only a small listing of disorders of the hematopoietic system that may be treated using the described HSCs; therefore, treatment of such disorders known to be susceptible to stem cell therapy should be considered to be within the scope of this disclosure. HSCs may also be used to treat defects in angiogenesis and bone marrow failure. In some embodiments the HSCs described herein can be administered to a subject to treat angiogenesis and bone marrow failure. In some embodiments the described HSCs administered to a subject to treat angiogenesis and bone marrow failure are autologous. In some embodiments the described HSCs administered to a subject to treat angiogenesis and bone marrow failure are heterologous.

The MSCs described herein may be used to treat a subject with a disorder of the hematopoietic system. In some embodiments the MSCs may be administered to a subject having an inflammatory, autoimmune, or degenerative disorder. Examples of such disorders include repair of infarcted myocardium, diabetes, Crohn's disease, multiple sclerosis, graft-versus-host disease, hepatitis, and many bone diseases. In some embodiments the described MSCs may be administered to a subject to repair of infarcted myocardium. In some embodiments the described MSCs may be administered to a subject to treat diabetes. In some embodiments the described MSCs may be administered to a subject to treat Crohn's disease. In some embodiments the described MSCs may be administered to a subject to treat multiple sclerosis. In some embodiments the described MSCs may be administered to a subject to treat graft-versus-host disease. In some embodiments the described MSCs may be administered to a subject to treat hepatitis. In some embodiments the described MSCs may be administered to a subject to treat a bone disease. In some embodiments the described MSCs administered to a subject to repair of infarcted myocardium are autologous. In some embodiments the described MSCs administered to a subject to treat diabetes are autologous. In some embodiments the described MSCs administered to a subject to treat Crohn's disease are autologous. In some embodiments the described MSCs administered to a subject to treat multiple sclerosis are autologous. In some embodiments the described MSCs administered to a subject to treat graft-versus-host disease are autologous. In some embodiments the described MSCs administered to a subject to treat hepatitis are autologous. In some embodiments the described MSCs administered to a subject to treat a bone disease are autologous. In some embodiments the described MSCs administered to a subject to repair of infarcted myocardium are heterologous. In some embodiments the described MSCs administered to a subject to treat diabetes are heterologous. In some embodiments the described MSCs administered to a subject to treat Crohn's disease are heterologous. In some embodiments the described MSCs administered to a subject to treat multiple sclerosis are heterologous. In some embodiments the described MSCs administered to a subject to treat graft-versus-host disease are heterologous. In some embodiments the described MSCs administered to a subject to treat hepatitis are heterologous. In some embodiments the described MSCs administered to a subject to treat a bone disease are heterologous. Those skilled in the art will understand that the forgoing disclosure provides only a small listing of inflammatory, autoimmune, or degenerative disorders that may be treated using the described MSCs; therefore, treatment of such disorders known to be susceptible to stem cell therapy should be considered to be within the scope of this disclosure.

The smooth muscle cells described herein may be used to treat a subject with a disorder of the cardiac or circulatory system. In some embodiments the SMCs may be administered to a subject having myocardial tissue damage, blood vessel damage, arterial disease due to lack of contractility. In some embodiments the described SMCs may be administered to a subject to treat myocardial tissue damage. In some embodiments the described SMCs may be administered to a subject to treat blood vessel damage. In some embodiments the described SMCs may be administered to a subject to treat arterial disease due to lack of contractility. In some embodiments the described SMCs administered to a subject to treat myocardial tissue damage are autologous. In some embodiments the described SMCs administered to a subject to treat blood vessel damage are autologous. In some embodiments the described SMCs administered to a subject to treat arterial disease due to lack of contractility are autologous. In some embodiments the described SMCs administered to a subject to treat myocardial tissue damage are heterologous. In some embodiments the described SMCs administered to a subject to treat blood vessel damage are heterologous. In some embodiments the described SMCs administered to a subject to treat arterial disease due to lack of contractility are heterologous. Those skilled in the art will understand that the forgoing disclosure provides only a small listing of the disorders that may be treated using the described SMCs; therefore, treatment of such disorders known to be susceptible to such therapy should be considered to be within the scope of this disclosure.

The unlimited functional endothelial cells described herein may also be used to treat a subject with a disorder of the cardiac or circulatory system. In some embodiments the UFECs may be administered to a subject to treat circulatory or cardiac damage following heart attack, such as poor contractility. In some embodiments the UFECs may be administered to a subject to treat pulmonary arterial hypertension. In some embodiments the UFECs may be administered to a subject to treat ischemic conditions such as, diabetes, where neovascularization may be beneficial. In administering the treatments described herein the UFECs administered may be autologous. In other embodiments, however, the UFECs administered may be heterologous.

Those skilled in the art will understand that the forgoing disclosure provides only a small listing of the disorders that may be treated using the described UFECs; therefore, treatment of such disorders known to be susceptible to such therapy should be considered to be within the scope of this disclosure.

Methods and compositions for therapeutic administration of the described cells to a subject are commonly known in the art and would be readily apparent to a skilled person in the field. For example, the described cells may be suspended in a pharmaceutically acceptable carrier, buffer, or other solution that is suitable for use with living cells to allow the cells to be administered to a subject. Routes of administration may include injection, catheter-based delivery, infusion, and the like. Other suitable means and routes of administration will be appreciated by those skilled in the related art and are considered to be within the scope of this disclosure.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Example 1—Production of Induced Pluripotent Stem Cells

Multiple human induced pluripotent stem cells (hiPSCs) were successfully generated from human umbilical vein endothelial cells (HUVECs) and fibroblasts by mediated expression of four transcription factors (Oct4, Sox2, klf4, and c-MYC). Those cells were continually cultured and propagated in a feeder free environment under chemically defined conditions. The hiPSCs maintained normal karyotype, and exhibited similar properties to human embryonic stem cells (hESCs) including self-renewing and differentiation into all three embryonic germ layers (FIGS. 1A-1M).

Example 2—Production of Cells of a Mesodermal Lineage by Culturing hiPSCs in MDM Studies were conducted to assess the impact of certain defined media on more than 10 hiPSC lines derived from both human umbilical vein endothelial cells (HUVECs) and fibroblasts. The gene expression profile of differentiation cells was analyzed by FACS and biologic function assays. Over a 12-day period of culturing hiPSCs in MDM (as set forth in Table 2) the cells were observed to be prone to commitment to the mesoderm lineage (FIGS. 3A-3F) and efficiently generated mesoderm precursors (FIGS. 4A-4E). In 10 independent experiments, cultures of $1\times10^5$ hiPSCs generated large numbers of mesoderm precursors peaking at $30\pm7\times10^6$ (CD31$^+$ cells: 51%±4.5, and CD34$^+$ cells: 37.%±3.6%) on day 10, and declining thereafter. The results indicate this culture method produced an approximate 100-fold increase in human CD34/CD31 positive cells compared to previously published protocols (see e.g. Wang et al., Nat. Biotechnol., 25:317 (2007); Goldman et al., Stem Cells 27:1750 (2009); Lancrin et al., Nature, 457:892 (2009); Morishima, et al., J. Cell Physiol., 226:1283 (2011); Rufaihah, et al, Arterioscler. Thromb. Vasc. Biol., 31:e72 (2011); Tolar J et al., Blood, 117:839 (2011); Niwa, et al. PLoS ONE, 6:e22261 (2011); Xu Y, et al. PLoS ONE, 7:e34321 (2012); White, et al., Stem Cells, 31:92 (2013).

Example 3—Mesoderm Precursor Cells are Multipotent

In order to assess the differentiation potential of mesoderm precursors (CD31/CD34+ cells) produced from hiPSCs, the cells were incubated under culture conditions known to induce endothelial cell formation by precursor cells. Various culture conditions induced the MPCs to develop into: unlimited functional endothelium (iUFECs), mesenchymal stem cells (iMSC), smooth muscle cells (iSMCs), and hematopoietic stem cells (iHSCs).

The mesoderm precursors were cultured under conditions promoting endothelial cell propagation and maturation, standard culture conditions (37° C. incubation at 5% CO2) using EGM™ 2 medium (Lanza). The cells expanded rapidly with typical cobblestone-like morphology, and expressed endothelial markers (CD31, vWF, and VE-cadherin (CD144)) as characterized by immunohistochemistry (FIGS. 5A-5D). The induced endothelial cells (iECs) exhibited further functional features of endothelial cells, as confirmed through the formation of vascular-like structures on Matrigel™ and the uptake of acetylated-LDL (FIGS. 5E-5G). Notably, these cells were able to be propagated more than 20 passages while sustaining an endothelial phenotype, based on cobblestone-like morphology, expression of endothelial markers, and biologic functions.

Figures 6I, 6J, 6K:
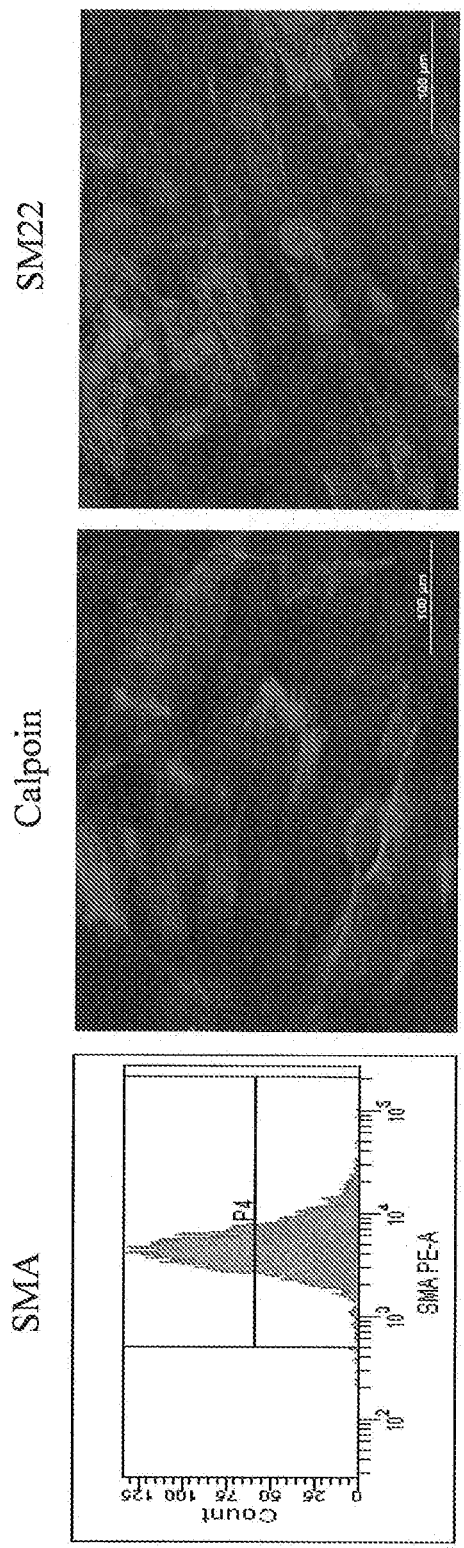

Mesoderm precursor cells were also cultured under conditions suitable for maintaining MSCs in culture (standard culture conditions (37° C. incubator at 5% CO2) with MSC growth medium (15~20% fetal-bovine serum and 1% penicillin-streptomycin in alpha minimal essential medium)), which revealed the mesoderm precursors can be induced to form MSC-like cells. The MSC phenotype of these cells was validated by observing the expression of CD90, CD73, and CD105, but not CD31 or CD45, as detected by FACS analysis (FIGS. 6A-6E). In addition to surface marker analysis, the most common and reliable way to identify a population of MSC is to verify their ability to differentiate into adipocytes, osteoblasts, myocytes, and chondrocytes in vivo and in vitro. To assess this function potential, the iMSCs derived from mesoderm precursors were cultured under conditions known to promote differentiation into osteoblasts (standard culture conditions (37° C. incubator at 5% CO2) with osteoblasts induction medium containing: 0.1 µM dexamethasone, 50 µM ascorbic acid-2-phosphate, 10 mM β-glycerol phosphate, 10% fetal-bovine serum, and 1% penicillin-streptomycin in alpha minimal essential medium) for 21 days, changing media every 4 to 5 days). The resulting cells were histochemically stained to determine their specific marker profile. After a one-week induction period, the cells featured very high phosphatase activity and a vast extracellular calcium deposit confirmed as Alizarin Red S staining followed by additional two weeks induction. These results indicate the iMSCs have the ability to differentiate into osteoblasts and mediate in vitro bone-formation (FIGS. 6F-6H).

The mesoderm precursors were cultured under conditions promoting SMC propagation and maturation (standard culture conditions (37° C. incubator at 5% CO2) with SMC growth medium (SmGM-2™, Lonza)). This caused the mesodermal precursor cells to display SMC-like properties, such as a spindle-like morphology and the strong expression of smooth muscle-specific markers, including α-SMA, calponin, and SM22, as confirmed by FACS analysis and immunohistochemistry (FIG. 6C). These results indicate that mesoderm precursors derived from hiPSCs have great potential to produce SMCs.

Figures 7A, 7B:
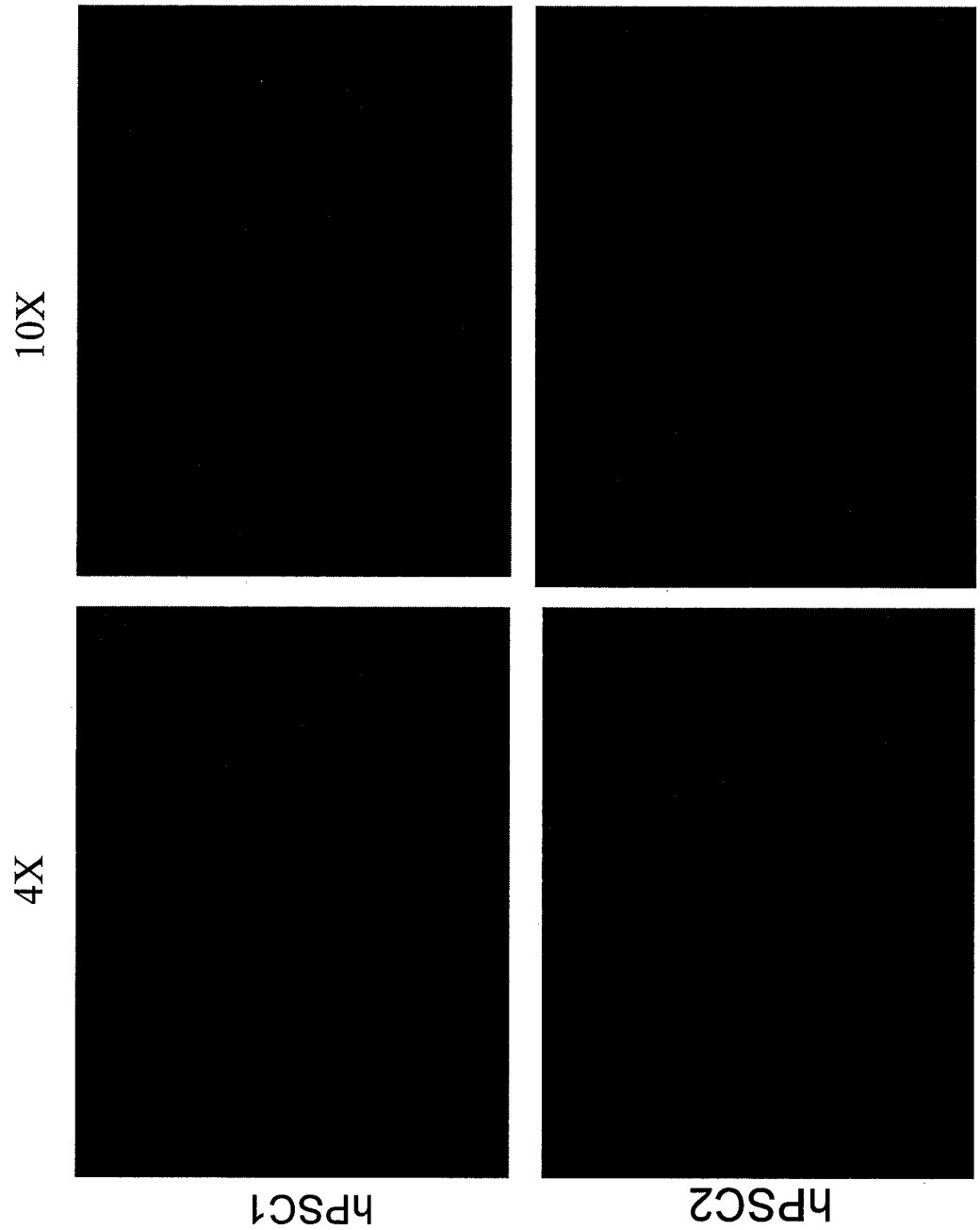
FIGS. 7A and 7B. Generation of hematopoietic lineage cells in suspension from hiPSCs through mesoderm precursor cells.
Figures 8A, 8B:
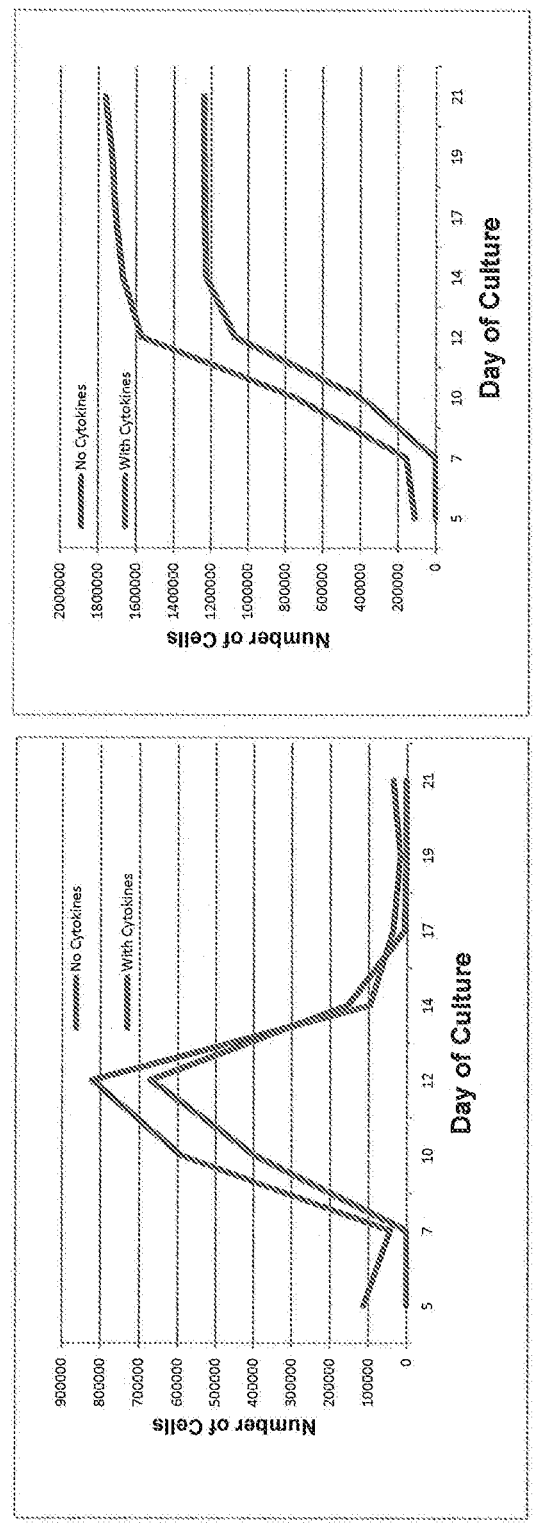
FIGS. 8A-8D. Generation of hematopoietic lineage cells in suspension from normal hiPSCs.
Figure 8C:
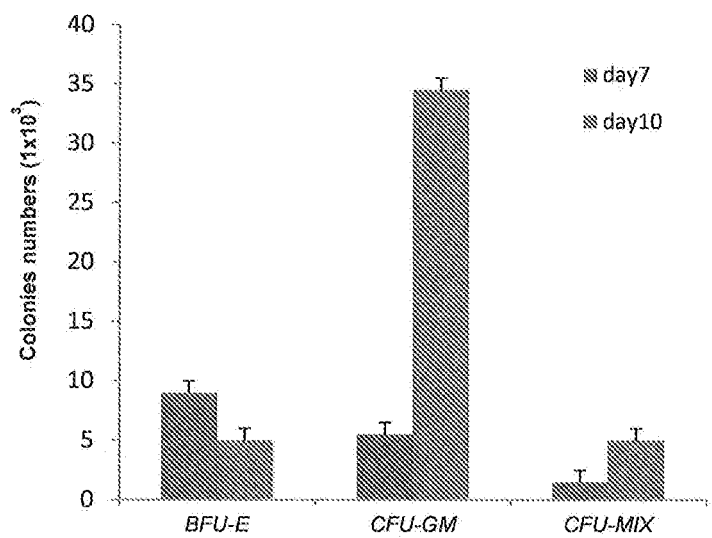
Figure 8D:
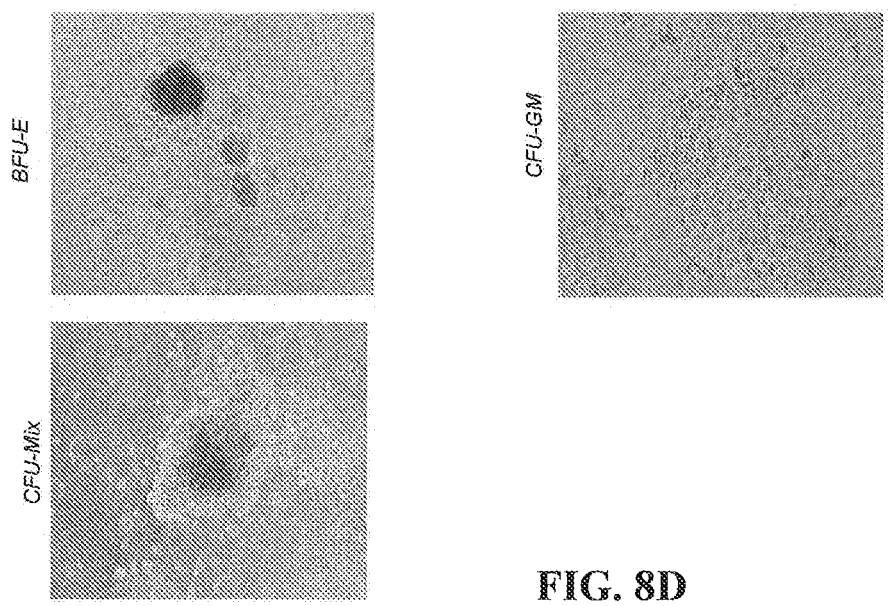

To test the hematopoietic lineage differentiation potential, the hiPSCs were cultured in Matrigel™ coated plates in MDM for up to three weeks. Some of the attached mesoderm precursor cells began to float starting on day 3 in the culture, and the numbers gradually increased with time. The suspension cells exhibited morphology reminiscent of primitive human hematopoietic stem/progenitors (FIGS. 7A and 7B). The suspension cell population expressed hematopoietic stem/progenitors markers CD34, CD31, and CD45 as confirmed by FACS (FIG. 8A). In 10 independent experiments, cultures of $1 \times 10^5$ hiPSCs resulted in remarkably large numbers of suspension cells peaking at $17 \pm 5 \times 10^6$ on day 12, and rapidly declining thereafter, consistent with a precise timing of appearance of hematopoietic cells in the system. The addition of hematopoietic stem/progenitors growth factors (SCF, Flt-3 ligand, and thrombopoietin) (i.e., MDM+ medium) in the culture promoted significant generation of hematopoietic stem/progenitors (FIG. 8A). Thus, up to $4 \sim 6 \times 10^6$ human $CD34^+$ cells were generated at day 12 from an initial culture of $1 \times 10^5$ hiPSCs, representing an about 500-1000 fold increase in human $CD34^+$ cells as compared to previously published protocols based on EB formation or co-culture on stromal cells. Interestingly, the majority of $CD34^+$ cells derived from this procedure hold a CD38 negative phenotype, consistent with an immature hematopoietic stem/progenitor cell population. To further validate their hematopoietic differentiation ability a clonogenic progenitor assay was performed. The suspension cells generated a large number of erythroid (burst-forming unit-erythroid (BFU-E)), myeloid (colony-forming unit-granulocytic, monocytic (CFU-GM)), and mixed (CFU-granulocytic, erythrocytic, monocytic, megakaryocytic (CFU-GEMM)) colonies (FIG. 8C). The erythroid and myeloid nature of BFU-E and CFU-GM colonies was confirmed by expression of the glycophorin and CD33 markers in these colonies, respectively.

Example 4—Modified Composition of Culture Medium

Table 5 shows a particular embodiment of MDM1.

TABLE 5

A particular embodiment of MDM1.

| Ingredient | Amount |
| --- | --- |
| Iscove's Modified Dulbecco's Medium (IMDM, Invitrogen, Catalog #: 21056-023) mixed with Ham's F-12 Nutrient Mix, with L-alanyl-L-glutamine (GlutaMax ™) additive (Invitrogen, Catalog #, 31765-035) | 1:1 mixture |
| Albucult ™ | 5 mg/ml |
| α-monothioglycerol (Sigma-Aldrich, Catalog #: M6145) | 3.9 µl per 100 ml |
| protein-free hybridoma mixture II (Invitrogen Catalog #: 12040-077) | 5% of total volume |
| L-ascorbic acid 2-phosphate (Sigma-Aldrich, Catalog #: A 8960) | 50 µg/ml |
| L-alanyl-L-glutamine (GlutaMax ™) (2 mM, Invitrogen, Catalog #: 35050061) | 2 mM |
| Antibiotic (Invitrogen, Catalog #: 15140122) | 50 units pen. 50 mg strep. |
| insulin-transferrin-selenium-ethanolamine supplement (Invitrogen, Catalog #: 515000560) | 1% of total volume |
| bone morphogenic protein 4 (R & D systems, Catalog #: 314-BP-050) | 10 ng/ml |

TABLE 5-continued

A particular embodiment of MDM1.

| Ingredient | Amount |
| --- | --- |
| vascular endothelial growth factor (Invitrogen, Catalog #: PHC9394) | 10 ng/ml |
| basic fibroblast growth factor (Pepro Tech, Catalog #: 100-18B) | 10 ng/ml |

MDM supplemented with hematopoietic cytokines (SCF, Flt-3 ligand and TPO) is named MDM+. MDM1 supplemented with hematopoietic cytokines (SCF, Flt-3 ligand and TPO) is referred to as MDM1+. Table 6 shows the composition of MDM1+.

TABLE 6

Composition of MDM1 supplemented with hematopoietic cytokines (MDM1+).

| Ingredient | Amount |
| --- | --- |
| MDM1 | See Table 4 |
| Recombinant human Stem Cell Factor (rhSCF) | 50 ng/mL |
| Recombinant human Flt-3 ligand (rhFlt-3L) | 50 ng/mL |
| Recombinant human Thrombopoietin (rhTPO) | 50 ng/mL |

Figure 9:
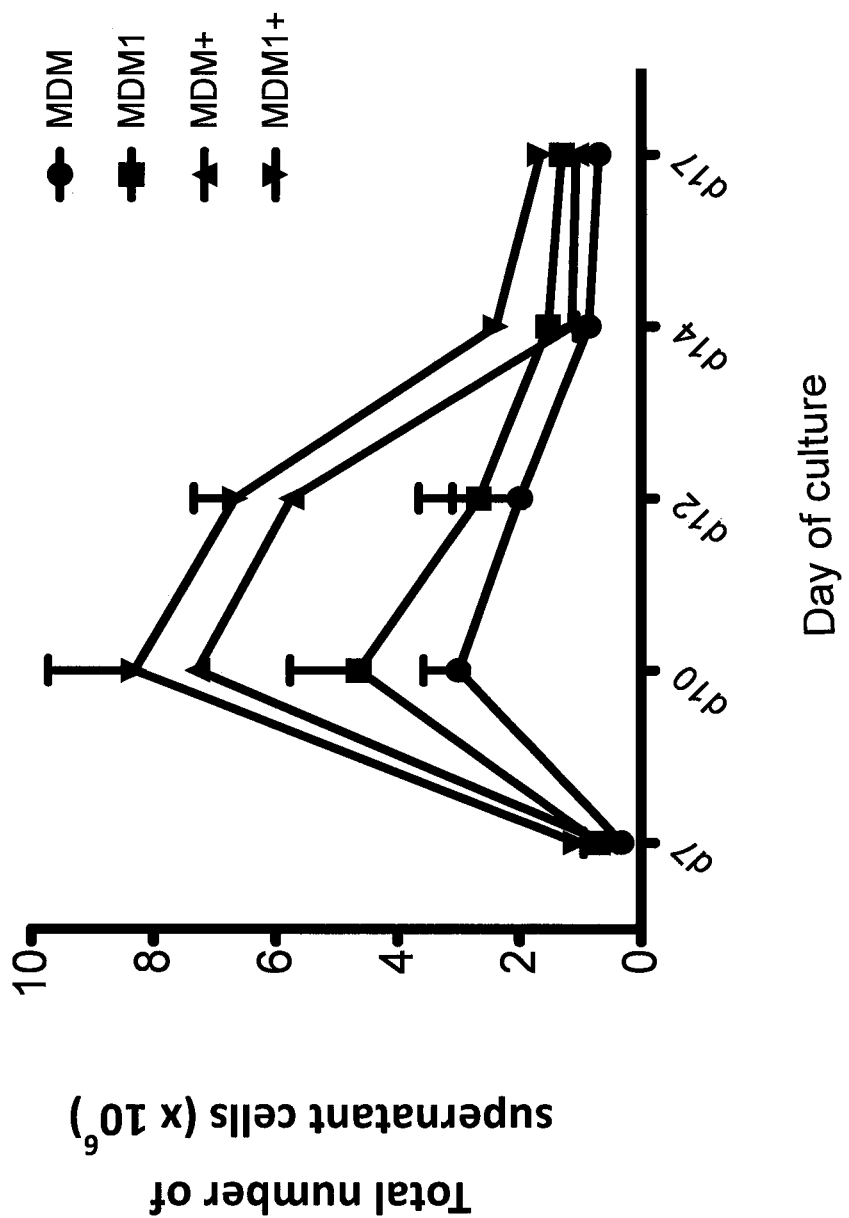
FIG. 9. Comparison of the total number of supernatant cells generated during iPSC differentiation.
Figure 10:
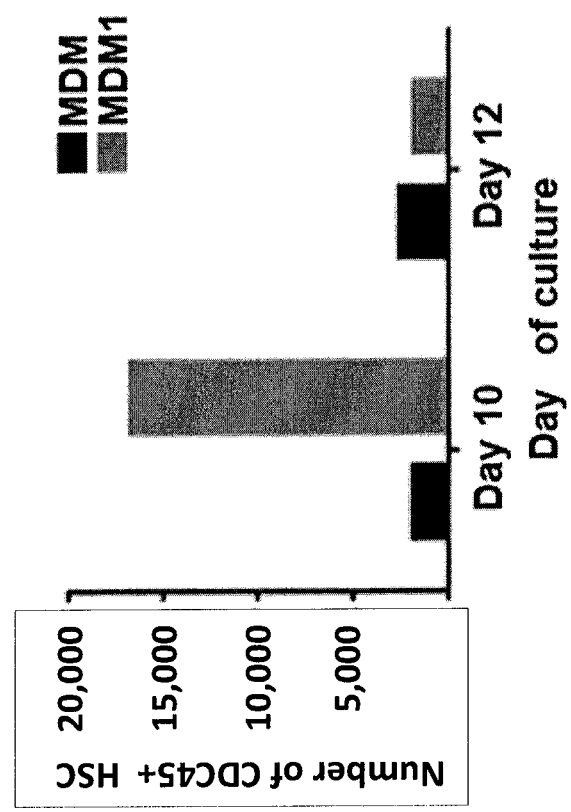
FIG. 10. MDM1 produces more CD45+ HSCs at day 10 of culture compared to MDM.

Compared to MDM or MDM+, iPSC differentiation with MDM1 or MDM1+ increases significantly the total number of supernatant cells (FIG. 9). This increase in the total number of supernatant cells resulted in a 8.7-fold increase in CD45+ cells hematopoietic stem cells (HSCs) at day 10 when MDM1 was employed during the differentiation process compared to MDM (FIG. 10).

Example 5—Modified Differentiation Protocol to Favor Hematopoietic Differentiation Human iPSC-derived supernatant cells were differentiated with MDM1 and MDM1+ using the otherwise unmodified protocol described in Examples 1 to 3. At day 10 of differentiation, the differentiation protocol was modified to further support hematopoietic differentiation. The protocol is unchanged for differentiation of the other 3 cell types described in Examples 1 to 3, namely, mesenchymal stem cells (MSC), smooth muscle cells (SMC), and unlimited functional endothelial cells (UFEC).

Figure 11:
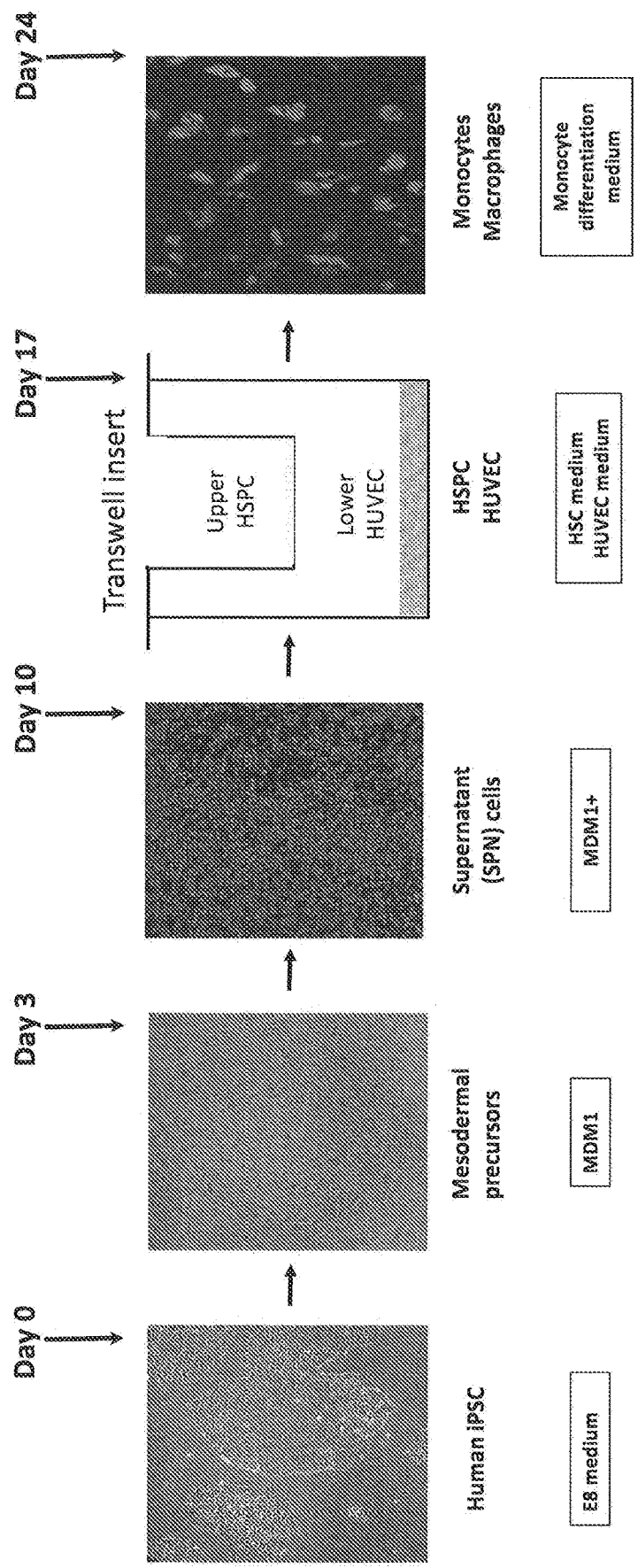
FIG. 11. Modified iPSC differentiation protocol to favor hematopoietic differentiation.

For hematopoietic differentiation, supernatant cells obtained from day 10 of differentiation were cultured in the upper chamber of a Transwell insert (Corning Inc.) in commercially available hematopoietic culture medium containing: 90% RPMI 1640 Medium (Gibco, Cat #11875-119), 10% Fetal Bovine Serum (Atlanta Biologicals, Cat #S10250), recombinant human SCF (Stemcell Technologies Inc.) at 100 ng/ml, recombinant human Flt-3 ligand (Stemcell Technologies Inc.) at 100 ng/ml, and recombinant human thrombopoietin (Stemcell Technologies Inc.) at 100 ng/ml, and recombinant human granulocyte/macrophage colony-stimulating factor at 100 ng/ml (PeproTech, Cat #AF-300-03). The lower chamber of the Transwell insert was occupied by human umbilical vein endothelial cells (HUVEC) cultured in commercially available endothelial cell culture medium EGM™ BulletKit™ (Lonza, Cat #cc-3162). (FIG. 11).

Under these co-culture conditions (in an incubator at 37° C. under 5% $CO_2$), the majority of the cells within the Transwell (85.47%±9.5) gradually matured into hematopoietic stem/progenitor cells (HSPC), displaying the hematopoietic lineage markers CD34 and CD45, as confirmed by flow cytometry. After 7 days of co-culture in a Transwell insert, these cells are further differentiated to the monocytic lineage using a medium containing: 90% RPMI 1640 Medium (Gibco, Cat #11875-119), 10% Fetal Bovine Serum (FBS, Atlanta Biologicals, Cat #S10250), recombinant human SCF (Stemcell Technologies Inc.) at 100 ng/ml, recombinant human Flt-3 ligand (Stemcell Technologies Inc.) at 100 ng/ml, and recombinant human thrombopoietin (Stemcell Technologies Inc.) at 100 ng/ml, recombinant human granulocyte/macrophage colony-stimulating factor at 100 ng/ml (PeproTech, Cat #AF-300-03), and recombinant human macrophage colony-stimulating factor at 100 ng/ml (PeproTech, Cat #AF-300-25). Phenotypic expression of monocytic markers (CD14, CD11b, and CD115) is confirmed by flow cytometry. These monocytes can subsequently be directed to differentiate into functional macrophages by using attachment cell culture conditions followed by RPMI 1640 (Gibco) supplemented with 10% FBS, 2 mmol/L L-glutamine, penicillin/streptomycin, and recombinant human granulocyte/macrophage colony-stimulating factor at 20 ng/ml (PeproTech), as confirmed by the in vitro phagocytosis assay. (Joachim Weischenfeldt and Bo Porse, Bone Marrow-Derived Macrophages (BMM): Isolation and Applications. Cold Spring Harbor Protocol, 2008; 3:1) (FIG. 11).

The invention claimed is:

1. A method of treating a subject for a congenital bone marrow disorder, comprising administering to the subject an iPSC-derived mesodermal precursor cell, comprising a mesodermal precursor cell expressing CD34 and CD31 on its cell surface, wherein the mesodermal precursor cell is capable of differentiating into a hematopoietic stem cell.

2. The method of claim 1, wherein the mesodermal precursor cell is capable of maintaining its phenotype for at least 3 days in a culture and/or of maintaining its phenotype for at least 3 passages in a culture.

3. The method of claim 1, wherein the hematopoietic stem cell expresses CD34, CD31, and CD45 on its surface.

4. The method of claim 1, wherein the hematopoietic stem cell is capable of reconstituting the hematopoietic system of an irradiated mouse.

5. The method of claim 1, wherein the congenital bone marrow disorder comprises a disorder of the hematopoietic system, a congenital aplastic anemia (Fanconi anemia), a congenital hypoplastic anemia (Diamond-Blackfan anemia), a congenital neutropenias (Kostmann syndrome, cyclic neutropenia, Shwachman-Diamond syndrome and others), and a congenital thrombocytopenias (TAR syndrome, amegacaryocytic thrombocytopenia).

* * * * *